US010799698B2

(12) United States Patent
Howard

(10) Patent No.: US 10,799,698 B2
(45) Date of Patent: Oct. 13, 2020

(54) TRANSCUTANEOUS ELECTRICALLY AMPLIFIED COGNITIVE ENHANCEMENT SYSTEM

(71) Applicant: Newton Howard, Providence, RI (US)

(72) Inventor: Newton Howard, Providence, RI (US)

( * ) Notice: Subject to any disclaimer, the term of this patent is extended or adjusted under 35 U.S.C. 154(b) by 0 days.

(21) Appl. No.: 16/443,652

(22) Filed: Jun. 17, 2019

(65) Prior Publication Data

US 2019/0381314 A1     Dec. 19, 2019

Related U.S. Application Data

(60) Provisional application No. 62/685,643, filed on Jun. 15, 2018.

(51) Int. Cl.
*A61N 1/36*     (2006.01)
*A61N 1/04*     (2006.01)
(Continued)

(52) U.S. Cl.
CPC ...... *A61N 1/36025* (2013.01); *A61B 5/04001* (2013.01); *A61N 1/0456* (2013.01);
(Continued)

(58) Field of Classification Search
CPC ............ A61N 1/36025; A61N 1/36031; A61N 1/36036; A61N 1/36053; A61N 1/37223; A61B 5/04001
See application file for complete search history.

(56) References Cited

U.S. PATENT DOCUMENTS 7,177,643 B2    2/2007   Howard
8,380,902 B2    2/2013   Howard
(Continued)

FOREIGN PATENT DOCUMENTS

WO    2017040741 A1    3/2017
WO    2017115368 A1    7/2017
WO    2017190049 A1    11/2017

OTHER PUBLICATIONS

Colzato et al.; Transcutaneous Vagal Nerve Stimulation (tVNS): a new neuromodulation tool in healthy humans?; Frontiers in Psychology; 6:102; Feb. 2015.*
(Continued)

*Primary Examiner* — Paula J Stice
(74) *Attorney, Agent, or Firm* — Smith, Gambrell & Russell, LLP.

(57) ABSTRACT

Embodiments may stimulate nerve activity using transcutaneous nerve stimulation, as well as monitor nerve activity through the skin. Various branches of the nervous system may be accessed at various points on the body. For example, system for monitoring and stimulating human body activity and conditions may comprise at least one transcutaneous nerve stimulation circuitry comprising a circuitry adapted to generate a nerve stimulation signal and at least one electrode or contact adapted to apply the nerve stimulation signal to a nerve of a human through a skin of the human, transcutaneous electrical nerve monitoring circuitry comprising a circuitry adapted to monitor at least one nerve signal received from at least one sensor adapted to obtain the at least one nerve signal from a human through the skin of the human, and control circuitry adapted to control signal generation and signal application of the transcutaneous nerve stimulation circuitry.

20 Claims, 18 Drawing Sheets

(51) Int. Cl.
A61N 1/372 (2006.01)
A61B 5/04 (2006.01)
(52) U.S. Cl.
CPC ..... *A61N 1/36031* (2017.08); *A61N 1/36036* (2017.08); *A61N 1/36053* (2013.01); *A61N 1/37223* (2013.01)

(56) References Cited

U.S. PATENT DOCUMENTS

| | | | |
|---|---|---|---|
| 8,642,332 | B2 | 2/2014 | Goldman et al. |
| 8,924,720 | B2 | 12/2014 | Raghuram et al. |
| 9,399,144 | B2 | 7/2016 | Howard |
| 2007/0225776 | A1* | 9/2007 | Fritsch ................. A61N 1/0541 607/57 |
| 2011/0060377 | A1 | 3/2011 | Howard |
| 2012/0064493 | A1 | 3/2012 | Howard et al. |
| 2012/0221075 | A1 | 8/2012 | Bentwich |
| 2013/0338526 | A1 | 12/2013 | Howard |
| 2017/0027812 | A1 | 2/2017 | Hyde et al. |
| 2018/0168905 | A1* | 6/2018 | Goodall ............... A61N 1/0456 |

OTHER PUBLICATIONS

Rangon et al.; Auricular Neuromodulation: The emerging Concept beyond the Stimulation of the Vagus and Trigeminal Nerves; J Neurol Neuromedicine (2018)3(4):35-38.*

Written Opinion of the International Searching Authority dated Sep. 10, 2019, received in International Application No. PCT/US19/37539; (6 pages).

Notification of Transmittal of the International Search Report dated Sep. 10, 2019, received in International Application No. PCT/US19/37539; (3 pages).

Penhune, V. B., and J. Doyon. "Cerebellum and M1 interaction during early learning of timed motor sequences." Journal Article. (Jul. 2005) 801-812. 26. 3. NeuroImage.

Pincus, David W., Tanvir F. Choudhri, Neil A. Feldstein, Michael B. Sisti, and Bennett M. Stein. "Moyamoya Syndrome Following Stereotactic Radiosurgery for AVM." Journal Article. (Sep. 1997) 731-731. 41. 3. Neurosurgery.

Poldrack, Russell A. "Imaging Brain Plasticity: Conceptual and Methodological Issues—A Theoretical Review." Journal Article. (Jul. 2000) 1-13. 12. 1. NeuroImage.

Porrill, John, and Paul Dean. "Cerebellar Motor Learning: When Is Cortical Plasticity Not Enough?" Journal Article. (2007) e197. 3. 10. PLoS Computational Biology.

Prevedel, Robert, Young-Gyu Yoon, Maximilian Hoffmann, Nikita Pak, Gordon Wetzstein, Saul Kato, Tina Schrödel, Ramesh Raskar, Manuel Zimmer, Edward S. Boyden, and Alipasha Vaziri. "Simultaneous whole-animal 3D imaging of neuronal activity using lightfield microscopy." Journal Article. (Jul. 2014) 727-730. 11. 7. Nature Methods.

Raberger, Thomas, and Heinz Wimmer. "On the automaticity/cerebellar deficit hypothesis of dyslexia: balancing and continuous rapid naming in dyslexic and ADHD children." Journal Article. (Jan. 2003) 1493-1497.41. 11. Neuropsychologia.

Reis, J., H. M. Schambra, L. G. Cohen, E R. Buch, B. Fritsch, E. Zarahn, R A. Celnik, and J. W. Krakauer. "Noninvasive cortical stimulation enhances motor skill acquisition over multiple days through an effect on consolidation." Journal Article. (Feb. 2009) 1590-1595. 106. 5. Proceedings of the National Academy of Sciences.

Resendez, Shanna L., Josh H. Jennings, Randall L. Ung, Vijay Mohan K. Namboodiri, Zhe Charles Zhou, James M. Otis, Hiroshi Nomura, Jenna A. McHenry, Oksana Kosyk, and Garret D. Stuber. "Visualization of cortical, subcortical and deep brain neural circuit dynamics during naturalistic mammalian behavior with headmounted microscopes and chronically implanted lenses." Journal Article. (Mar. 2016) 566-597. 11. 3. Nature Protocols.

Roozendaal, Benno, and James L. McGaugh. "Memory modulation." Journal Article. (Dec. 2011) 797-824. 125. 6. Behavioral Neuroscience.

Roy, Dheeraj S., Autumn Arons, Teryn I. Mitchell, Michele Pignatelli, Tomás J. Ryan, and Susumu Tonegawa. "Memory retrieval by activating engram cells in mouse models of early Alzheimer's disease." Journal Article. (Mar. 2016) 508-512. 531. 7595. Nature.

Roy, Neeta S., Abdellatif Benraiss, Su Wang, Richard A. R. Fraser, Robert Goodman, William T. Couldwell, Maiken Nedergaard, Ayano Kawaguchi, Hideyuki Okano, and Steven A. Goldman. "Promoter-targeted selection and isolation of neural progenitor cells from the adult human ventricular zone." Journal Article. (2000) 321-331. 59. 3. Journal of neuroscience research.

Russell, James T. "Imaging calcium signals in vivo: a powerful tool in physiology and pharmacology: <i>In vivo</i> calcium imaging." Journal Article. (Aug. 2011) 1605-1625. 163. 8. British Journal of Pharmacology.

Sanai, Nader, Anthony D. Tramontin, Alfredo Quinones-Hinojosa, Nicholas M. Barbaro, Nalin Gupta, Sandeep Kunwar, Michael T. Lawton, Michael W. McDermott, Andrew T. Parsa, José Manuel-García Verdugo, Mitchel S. Berger, and Arturo Alvarez-Buylla. "Unique astrocyte ribbon in adult human brain contains neural stem cells but lacks chain migration." Journal Article. (Feb. 2004) 740-744. 427. 6976. Nature.

Schachter, Steven C. "Vagus nerve stimulation: mood and cognitive effects." Journal Article. (Feb. 2004) 56-59. 5. Epilepsy & Behavior.

Scheggia, Diego, Audrey Bebensee, Daniel R. Weinberger, and Francesco Papaleo. "The Ultimate Intra-/Extra-Dimensional Attentional Set-Shifting Task for Mice." Journal Article. (Apr. 2014) 660-670. 75. 8. Biological Psychiatry.

Scheggia, Diego, and Francesco Papaleo. "An Operant Intra-/Extra-dimensional Set-shift Task for Mice." Journal Article. (Jan. 2016) 53503. 107. Journal of Visualized Experiments.

Schmahmann, Jeremy D. "An Emerging Concept: The Cerebellar Contribution to Higher Function." Journal Article. (Nov. 1991) 1178.48. 11. Archives of Neurology.

Schonewille, Martijn, Zhenyu Gao, Henk-Jan Boele, Maria F Vinueza Veloz, Wardell E Amerika, Antonia A M. Šimek, Marcel T De Jeu, Jordan P Steinberg, Kogo Takamiya, Freek E Hoebeek, David J Linden, Richard L Huganir, and Chris I De Zeeuw. "Reevaluating the Role of LTD in Cerebellar Motor Learning." Journal Article. (Apr. 2011) 43-50. 70. 1. Neuron.

Schooler, Eve M., Carl Livadas, Joohwan Kim, Prashant Gandhi, Pablo R. Passera, Jaideep Chandrashekar, Steve Orrin, Martin Koyabe, Fadi El Moussa, and Gogobada Daa Dabibi. "Collaborative defence as a pervasive service: architectural insights and validation methodologies of a trial deployment" Journal Article. (2010) 65. 8. 2. International Journal of Sensor Networks.

Scott, William A. "Cognitive Complexity and Cognitive Flexibility." Journal Article. (Dec. 1962) 405. 25. 4. Sociometry.

Seitz, A. R., N. Yamagishi, B. Werner, N. Goda, M. Kawato, and T. Watanabe. "Task-specific disruption of perceptual learning." Journal Article. (Oct. 2005) 14895-14900. 102. 41. Proceedings of the National Academy of Sciences.

Seymour, B., N. D. Daw, J. P. Roiser, P. Dayan, and R. Dolan. "Serotonin Selectively Modulates Reward Value in Human Decision-Making." Journal Article. (Apr. 2012) 5833-5842. 32. 17. Journal of Neuroscience.

Shackman, Alexander J., Tim V. Salomons, Heleen A. Slagter, Andrew S. Fox, Jameel J. Winter, and Richard J. Davidson. "The integration of negative affect, pain and cognitive control in the cingulate cortex." Journal Article. (Mar. 2011) 154-167. 12. 3. Nature Reviews Neuroscience.

Shibasaki, Hiroshi. "Human brain mapping: Hemodynamic response and electrophysiology." Journal Article. (Apr. 2008) 731-743. 119. 4. Clinical Neurophysiology.

Shiner, Tamara, Ben Seymour, Klaus Wunderlich, Ciaran Hill, Kailash P. Bhatia, Peter Dayan, and Raymond J. Dolan. "Dopamine and performance in a reinforcement learning task: evidence from Parkinson's disease." Journal Article. (Jun. 2012) 1871-1883. 135. 6. Brain.

Shiotsuki, Hiromi, Kenji Yoshimi, Yasushi Shimo, Manabu Funayama, Yukio Takamatsu, Kazutaka Ikeda, Ryosuke Takahashi, Shigeru

(56) References Cited

OTHER PUBLICATIONS

Kitazawa, and Nobutaka Hattori. "A rotarod test for evaluation of motor skill learning." Journal Article. (Jun. 2010) 180-185. 189. 2. Journal of Neuroscience Methods.

Sikström, Sverker, and Göran Söderlund. "Stimulus-dependent dopamine release in attention-deficit/hyperactivity disorder." Journal Article. (2007) 1047-1075. 114. 4. Psychological Review.

Smucny, Jason, Adrienne Visani, and Jason R. Tregellas. "Could Vagus Nerve Stimulation Target Hippocampal Hyperactivity to Improve Cognition in Schizophrenia?" Journal Article. (Mar. 2015) 6. Frontiers in Psychiatry.

Steenbergen, Laura, Roberta Sellaro, Ann-Kathrin Stock, Bart Verkuil, Christian Beste, and Lorenza S. Colzato. "Transcutaneous vagus nerve stimulation (tVNS) enhances response selection during action cascading processes." Journal Article. (Jun. 2015) 773-778. 25. 6. European Neuropsychopharmacology.

Stefan, Hermann, Gernot Kreiselmeyer, Frank Kerling, Katrin Kurzbuch, Christophe Rauch, Marcel Heers, Burkhard S. Kasper, Thilo Hammen, Martina Rzonsa, Elisabeth Pauli, Jens Ellrich, Wolfgang Graf, and Rüdiger Hopfengärtner. "Transcutaneous vagus nerve stimulation (t-VNS) in pharmacoresistant epilepsies: A proof of concept trial: Transcutaneous Vagus Nerve Stimulation." Journal Article. (Jul. 2012) e115-e118. 53. 7. Epilepsia.

Steindler, Dennis A., and David W. Pincus. "Stem cells and neuropoiesis in the adult human brain." Journal Article. (Mar. 2002) 1047-1054. 359. 9311. The Lancet.

Stocco, Andrea, Christian Lebiere, and John Robert Anderson. "Dopamine, learning, and production rules: The basal ganglia and the flexible control of information transfer in the brain." Conference Proceedings. (2009).

Stoodley, Catherine J. "The Cerebellum and Cognition: Evidence from Functional Imaging Studies." Journal Article. (Mar. 2011) 352-365. 11. 2. The Cerebellum.

Stoodley, Catherine J., and Jeremy D. Schmahmann. "Evidence for topographic organization in the cerebellum of motor control versus cognitive and affective processing." Journal Article. (Jul. 2010) 831-844. 46. 7. Cortex.

Su, Lijuan, Min Yao, Nenggan Zheng, and Zhaohui Wu. "Correlation Between Extreme Learning Machine and Entorhinal Hippocampal System." Book Section. (2016) 307-315. Springer International Publishing. Cham.

Su, Lijuan, Nenggan Zhang, Min Yao, and Zhaohui Wu. "A Computational Model of the Hybrid Bio-Machine MPMS for Ratbots Navigation." Journal Article. (Nov. 2014) 5-13. 29. 6. IEEE Intelligent Systems.

Su, Li-Juan, and Min Yao. "Extreme learning machine with multiple kernels." Conference Proceedings. (Jun. 2013) 424-429. 2013 10th IEEE International Conference on Control and Automation (ICCA).

Sultana, Madeena, Padma Polash Paul, and Marina Gavrilova. "A Concept of Social Behavioral Biometrics: Motivation, Current Developments, and Future Trends." Conference Proceedings. (Oct. 2014) 271-278. 2014 International Conference on Cyberworlds (CW).

Sultana, Madeena, Padma Polash Paul, and Marina Gavrilova. "Mining Social Behavioral Biometrics in Twitter." Conference Proceedings. (Oct. 2014) 293-299. 2014 International Conference on Cyberworlds (CW).

Sultana, Madeena, Padma Polash Paul, and Marina Gavrilova. "Social Behavioral Biometrics: An Emerging Trend." Journal Article. (Dec. 2015) 1556013. 29. 08. International Journal of Pattern Recognition and Artificial Intelligence.

Sultana, Madeena, Padma Polash Paul, and Marina Gavrilova. "A Novel Index-Based Rank Fusion Method for Occluded Ear Recognition." Conference Proceedings. (Oct. 2015) 337-344. 2015 International Conference on Cyberworlds (CW).

Sultana, Madeena, Padma Polash Paul, and Marina Gavrilova. "Identifying Users from Online Interactions in Twitter." Book Section. (2016) 111-124. Springer Berlin Heidelberg. Berlin, Heidelberg.

Swapna, Immani, Brian Bondy, and Hitoshi Morikawa. "Differential Dopamine Regulation of Ca 2+ Signaling and Its Timing Dependence in the Nucleus Accumbens." Journal Article. (Apr. 2016) 563-573. 15. 3. Cell Reports.

Uemura, T., S. Kakizawa, M. Yamasaki, K. Sakimura, M. Watanabe, M. Iino, and M. Mishina. "Regulation of Long-Term Depression and Climbing Fiber Territory by Glutamate Receptor 2 at Parallel Fiber Synapses through its C-Terminal Domain in Cerebellar Purkinje Cells." Journal Article. (Oct. 2007) 12096-12108. 27. 44. Journal of Neuroscience.

Van Leusden, Jelle W. R., Roberta Sellaro, and Lorenza S. Colzato. "Transcutaneous Vagal Nerve Stimulation (tVNS): a new neuromodulation tool in healthy humans?" Journal Article. (Feb. 2015) 6. Frontiers in Psychology.

Vauleon, Elodie, Habiba Mesbah, Daniel Gedouin, Isabelle Lecouillard, Guillaume Louvel, Abderrahmane Hamlat, Laurent Riffaud, Béatrice Carsin, Véronique Quillien, Odile Audrain, and Thierry Lesimple. "Retrospective analysis of 24 recurrent glioblastoma after chemoradiation and treated with hitrosoureas or irinotecan and bevacizumab." Journal Article. (Feb. 2012) 121-126. 99. 2. Bulletin du Cancer.

Ventureyra, E. C. G. "Transcutaneous vagus nerve stimulation for partial onset seizure therapy." Journal Article. (Feb. 2000) 101-102. 16.2. Child's Nervous System.

Vera-Portocarrero, Louis P., Toni Cordero, Tina Billstrom, Kim Swearingen, Paul W. Wacnik, and Lisa M. Johanek. "Differential Effects of Subcutaneous Electrical Stimulation (SQS) and Transcutaneous Electrical Nerve Stimulation (TENS) in Rodent Models of Chronic Neuropathic or Inflammatory Pain: Effects of TENS vs. SQS in Rodent Models of Pain." Journal Article. (Jul. 2013) 328-335. 16. 4. Neuromodulation: Technology at the Neural Interface.

Vercher, J. L., and G. M. Gauthier. "Cerebellar involvement in the coordination control of the oculo-manual tracking system: effects of cerebellar dentate nucleus lesion." Journal Article. (1988) 155-166. 73. 1. Experimental Brain Research.

Wiecki, Thomas V., and Michael J. Frank. "A computational model of inhibitory control in frontal cortex and basal ganglia." Journal Article. (2013) 329-355. 120. 2. Psychological Review.

Ahmed, Faisal, Padma Polash Paul, and Marina L. Gavrilova. "Evolutionary fusion of local texture patterns for facial expression recognition." Conference Proceedings. (Sep. 2015) 1031-1035. 2015 IEEE International Conference on Image Processing (ICIP).

Ahmmed, Jafrin, Paul Padma Polash, and Shamim Ahmed. "Substance based automatic image construction from unordered subjective pieces of digital image." Conference Proceedings. (Dec. 2007) 1-5. 2007 10th International Conference on Computer and Information Technology (ICCIT 2007).

Allard, Simon, Varin Gosein, A. Claudio Cuello, and A. Ribeiro-Da-Silva. "Changes with aging in the dopaminergic and noradrenergic innervation of rat neocortex." Journal Article. (Dec. 2011) 2244-2253. 32. 12. Neurobiology of Aging.

Alnaes, D., M. H. Sneve, T. Espeseth, T. Endestad, S. H. P. Van De Pavert, and B. Laeng. "Pupil size signals mental effort deployed during multiple object tracking and predicts brain activity in the dorsal attention network and the locus coeruleus." Journal Article. (Apr. 2014) 1-1. 14. 4. Journal of Vision.

Alvarez, P., and L. R. Squire. "Memory consolidation and the medial temporal lobe: A simple network model." Journal Article. (Jul. 1994) 7041-7045. 91. 15. Proceedings of the National Academy of Sciences.

Amrani, Khalil, Robert W. Dykes, and Yves Lamarre. "Bilateral contributions to motor recovery in the monkey following lesions of the deep cerebellar nuclei." Journal Article. (Nov. 1996) 275-284. 740. 1-2. Brain Research.

Argyropoulos, Georgios P. D. "Experimental use of transcranial direct current stimulation (tdcs) in relation to the cerebellum and language." Book Section. (2016) 377-407. Issue. Journal.

Aston-Jones, Gary, and Jonathan D. Cohen. "Adaptive gain and the role of the locus coeruleus-norepinephrine system in optimal performance." Journal Article. (Dec. 2005) 99-110. 493. 1. The Journal of Comparative Neurology.

Aston-Jones, Gary, Janusz Rajkowski, and Jonathan Cohen. "Role of locus coeruleus in attention and behavioral flexibility." Journal Article. (Nov. 1999) 1309-1320.46. 9. Biological Psychiatry.

(56) References Cited

OTHER PUBLICATIONS

Atallah, Hisham E., Michael J. Frank, and Randall C. O'Reilly. "Hippocampus, cortex, and basal ganglia: Insights from computational models of complementary learning systems." Journal Article. (Nov. 2004) 253-267. 82. 3. Neurobiology of Learning and Memory.
Avril, Tony, Elodie Vauleon, Abderrahmane Hamlat, Stephan Saikali, Amandine Etcheverry, Caroline Delmas, Sylma Diabira, Jean Mosser, and Véronique Quillien. "Human glioblastoma stem-like cells are more sensitive to allogeneic nk and t cell-mediated killing compared with serum-cultured glioblastoma cells: Nk and t cells kill glioma stem-like cells." Journal Article. (Mar. 2012) 159-174. 22. 2. Brain Pathology.
Bäckman, Lars, Lars Nyberg, Ulman Lindenberger, Shu-Chen Li, and Lars Farde. "The correlative triad among aging, dopamine, and cognition: Current status and future prospects." Journal Article. (Jan. 2006) 791-807. 30. 6. Neuroscience & Biobehavioral Reviews.
Badre, David, Sophie Lebrecht, David Pagliaccio, Nicole M. Long, and Jason M. Scimeca. "Ventral Striatum and the Evaluation of Memory Retrieval Strategies." Journal Article. (Sep. 2014) 1928-1948. 26. 9. Journal of Cognitive Neuroscience.
Baillieux, Hanne, Hyo Jung De Smet, Philippe F. Paquier, Peter P. De Deyn, and Peter Mariën. "Cerebellar neurocognition: Insights into the bottom of the brain." Journal Article. (Sep. 2008) 763-773. 110. 8. Clinical Neurology and Neurosurgery.
Baizer, Joan S., Ines Kralj-Hans, and Mitchell Glickstein. "Cerebellar Lesions and Prism Adaptation in Macaque Monkeys." Journal Article. (Apr. 1999) 1960-1965. 81. 4. Journal of Neurophysiology.
Balsters, Joshua H., Christopher D. Whelan, Ian H. Robertson, and Narender Ramnani. "Cerebellum and Cognition: Evidence for the Encoding of Higher Order Rules." Journal Article. (Jun. 2013) 1433-1443. 23. 6. Cerebral Cortex.
Bastian, Amy J. "Learning to predict the future: the cerebellum adapts feedforward movement control." Journal Article. (Dec. 2006) 645-649. 16. 6. Current Opinion in Neurobiology.
Beaudry, Olivia, Ian Neath, Aimée M. Surprenant, and Gerald Tehan. "The focus of attention is similar to other memory systems rather than uniquely different." Journal Article. (2014) 8. Frontiers in Human Neuroscience.
Ben-Menachem, E., D. Revesz, B. J. Simon, and S. Silberstein. "Surgically implanted and non-invasive vagus serve stimulation: a review of efficacy, safety and tolerability." Journal Article. (Sep. 2015) 1260-1268. 22. 9. European Journal of Neurology.
Boon, Paul, Ine Moors, Veerle De Herdt, and Kristl Vonck. "Vagus nerve stimulation and cognition." Journal Article. (Jun. 2006) 259-263 15. 4. Seizure.
Borenstein, Aaron M., and Nathaniel D. Daw. "Dissociating hippocampal and striatal contributions to sequential prediction learning: Sequential predictions in hippocampus and striatum." Journal Article. (Apr. 2012) 1011-1023. 35. 7. European Journal of Neuroscience.
Brashers-Krug, Thomas, Reza Shadmehr, and Emilio Bizzi. "Consolidation in human motor memory." Journal Article. (Jul. 1996) 252-255. 382. 6588. Nature.
Bruinsma, Caroline F., Martijn Schonewille, Zhenyu Gao, Eleonora M. A. Aronica, Matthew C. Judson, Benjamin D. Philpot, Freek E. Hoebeek, Geeske M. Van Woerden, Chris I. De Zeeuw, and Ype Elgersma. "Dissociation of locomotor and cerebellar deficits in a murine Angelman syndrome model." Journal Article. (Oct. 2015) 4305-4315. 125. 11. Journal of Clinical Investigation.
Busch, Volker, Florian Zeman, Andreas Heckel, Felix Menne, Jens Ellrich, and Peter Eichhammer. "The effect of transcutaneous vagus nerve stimulation on pain perception—An experimental study." Journal Article. (Mar. 2013) 202-209. 6. 2. Brain Stimulation.
Cañas, José, José Quesada, Adoración Antolí, and Inmaculada Fajardo. "Cognitive flexibility and adaptability to environmental changes in dynamic complex problem-solving tasks." Journal Article. (Apr. 2003) 482-501. 46. 5. Ergonomics.
Cavanagh, James F., Thomas V. Wiecki, Michael X. Cohen, Christina M. Figueroa, Johan Samanta, Scott J. Sherman, and Michael J. Frank. "Subthalamic nucleus stimulation reverses mediofrontal influence over decision threshold." Journal Article. (Nov. 2011) 1462-1467. 14. 11. Nature Neuroscience.
Chandler, Daniel J. "Evidence for a specialized role of the locus coeruleus noradrenergic system in cortical circuitries and behavioral operations." Journal Article. (Jun. 2016) 197-206. 1641. Brain Research.
Chen, C., and R. F. Thompson. "Temporal specificity of long-term depression in parallel fiber—Purkinje synapses in rat cerebellar slice." Journal Article. (Jan. 1995) 185-198. 2. 3-4. Learning & Memory.
Chen, R., L. G. Cohen, and M. Hallett. "Nervous system reorganization following injury." Journal Article. (Jun. 2002) 761-773. 111. 4. Neuroscience.
Chen, Tsai-Wen, Trevor J. Wardill, Yi Sun, Stefan R. Pulver, Sabine L. Renninger, Amy Baohan, Eric R. Schreiter, Rex A. Kerr, Michael B. Orger, Vivek Jayaraman, Loren L. Looger, Karel Svoboda, and Douglas S. Kim. "Ultrasensitive fluorescent proteins for imaging neuronal activity." Journal Article. (Jul. 2013) 295-300. 499. 7458. Nature.
Clark, Vincent P., Brian A. Coffman, Andy R. Mayer, Michael P. Weisend, Terran D. R. Lane, Vince D. Calhoun, Elaine M. Raybourn, Christopher M. Garcia, and Eric M. Wassermann. "TDCS guided using fMRI significantly accelerates learning to identify concealed objects." Journal Article. (Jan. 2012) 117-128. 59. 1. NeuroImage.
Clark, Vincent P., and Raja Parasuraman. "Neuroenhancement: Enhancing brain and mind in health and in disease." Journal Article. (Jan. 2014) 889-894. 85. NeuroImage.
Coffin, Joan M., Susan Baroody, Kimberly Schneider, and Joshua O'Neill. "Impaired Cerebellar Learning in Children with Prenatal Alcohol Exposure: A Comparative Study of Eyeblink Conditioning in Children with ADHD and Dyslexia." Journal Article. (Jan. 2005) 389-398. 41. 3. Cortex.
Coffman, Brian A., Vincent P. Clark, and Raja Parasuraman. "Battery powered thought: attention, learning, and memory in healthy adults using transcranial direct current stimulation." Journal Article. (Jan. 2014) 895-908. 85. NeuroImage.
Cohen, Daniel A., and Edwin M. Robertson. "Preventing interference between different memory tasks." Journal Article. (Aug. 2001) 953-955. 14. 8. Nature Neuroscience.
Collins, Anne G. E., and Michael J. Frank "Cognitive control over learning: Creating, clustering, and generalizing task-set structure." Journal Article. (2013) 190-229. 120. 1. Psychological Review.
Cools, R., M. J. Frank, S. E. Gibbs, A. Miyakawa, W. Jagust, and M. D'Esposito. "Striatal Dopamine Predicts Outcome-Specific Reversal Learning and Its Sensitivity to Dopaminergic Drug Administration." Journal Article. (Feb. 2009) 1538-1543. 29. 5. Journal of Neuroscience.
Cools, Roshan, Kae Nakamura, and Nathaniel D. Daw. "Serotonin and Dopamine: Unifying Affective, Activational, and Decision Functions." Journal Article. (Jan. 2011) 98-113. 36. 1. Neuropsychopharmacology.
D'Angelo, Egidio, and Stefano Casali. "Seeking a unified framework for cerebellar function and dysfunction: from circuit operations to cognition." Journal Article. (2013) 6. Frontiers in Neural Circuits.
Dalley, J. W., and J. P. Roiser. "Dopamine, serotonin and impulsivity." Journal Article. (Jul. 2012) 42-58. 215. Neuroscience.
De Martino, B. "Frames, Biases, and Rational Decision-Making in the Human Brain." Journal Article. (Aug. 2006) 584-687. 313. 5787. Science.
Delange, J. M., I. Garza, and C. E. Robertson. "Clinical Reasoning: A 50-year-old woman with deep stabbing ear pain." Journal Article. (Oct. 2014) e152-e157. 83. 16. Neurology.
Den Ouden, Hanneke E M., Nathaniel D Daw, Guillén Fernandez, Joris A Elshout, Mark Rijpkema, Martine Hoogman, Barbara Franke, and Roshan Cools. "Dissociable Effects of Dopamine and Serotonin on Reversal Learning." Journal Article. (Dec. 2013) 1572. 80. 6. Neuron.
Desantana, Josimari M., Kathleen A. Sluka, and Gabriela Rocha Lauretti. "High and Low Frequency TENS Reduce Postoperative Pain Intensity After Laparoscopic Tubal Ligation: A Randomized Controlled Trial." Journal Article. (Jan. 2009) 12-19. 25. 1. The Clinical Journal of Pain.

(56) References Cited

OTHER PUBLICATIONS

Desantana, Josimari M., Deirdre M. Walsh, Carol Vance, Barbara A. Rakel, and Kathleen A. Sluka. "Effectiveness of transcutaneous electrical nerve stimulation for treatment of hyperalgesia and pain." Journal Article. (Dec. 2008) 492-499. 10. 6. Current Rheumatology Reports.

Di Pino, Giovanni, Giovanni Pellegrino, Giovanni Assenza, Fioravante Capone, Florinda Ferreri, Domenico Formica, Federico Ranieri, Mario Tombini, Ulf Ziemann, John C. Rothwell, and Vincenzo Di Lazzaro. "Modulation of brain plasticity in stroke: a novel model for neurorehabilitation." Journal Article. (Oct. 2014) 597-608. 10. 10. Nature Reviews Neurology.

Doll, B. B., K. E. Hutchison, and M. J. Frank. "Dopaminergic Genes Predict Individual Differences in Susceptibility to Confirmation Bias." Journal Article. (Apr. 2011) 6188-6198. 31. 16. Journal of Neuroscience.

Dombeck, Daniel A., Christopher D. Harvey, Lin Tian, Loren L. Looger, and David W. Tank. "Functional imaging of hippocampal place cells at cellular resolution during virtual navigation." Journal Article. (Nov. 2010) 1433-1440. 13. Nature Neuroscience.

Dorr, Adrienne E., and Guy Debonnel. "Effect of Vagus Nerve Stimulation on Serotonergic and Noradrenergic Transmission." Journal Article. (Aug. 2006) 890-898. 318. 2. Journal of Pharmacology and Experimental Therapeutics.

Dunaevsky, Anna. "Neuron—Glial Interactions in the Developing Cerebellum." Journal Article. (Aug. 2012) 742-744. 18. 4. Microscopy and Microanalysis.

Kolb, Bryan, G. Campbell Teskey, and Robbin Gibb. "Factors influencing cerebral plasticity in the normal and injured brain." Journal Article. (Nov. 2010) 204-204. 4. Frontiers in Human Neuroscience.

Wilms, Christian D., and Michael Häusser. "Reading out a spatiotemporal population code by imaging neighbouring parallel fibre axons in vivo." Journal Article. (May 2015) 6464. 6. 1. Nature Communications.

Wirz, Annarita, Silvia Mandillo, Francesca R. D'Amato, Alessandro Giuliani, and M. Cristina Riviello. "Response, use and habituation to a mouse house in C57BL/6J and BALB/c mice." Journal Article. (2015) 281-293. 64. 3. Experimental Animals.

Wlodkowski, Raymond J. "Accelerated learning in colleges and universities." Journal Article. (2003) 5-16. 2003. 97. New Directions for Adult and Continuing Education.

Yotsumoto, Yuko, Li-Hung Chang, Takeo Watanabe, and Yuka Sasaki. "Interference and feature specificity in visual perceptual learning." Journal Article. (Oct. 2009) 2611-2623. 49. 21. Vision Research.

Yotsumoto, Yuko, Takeo Watanabe, Li-Hung Chang, and Yuka Sasaki. "Consolidated learning can be susceptible to gradually-developing interference in prolonged motor learning." Journal Article. (2013) 7. Frontiers in Computational Neuroscience.

Zhang, Ting, Lu Huang, Li Zhang, Minjie Tan, Mingliang Pu, Gary E. Pickard, Kwok-Fai So, and Chaoran Ren. "On and Off retinal ganglion cells differentially regulate serotonergic and GABAergic activity in the dorsal raphe nucleus." Journal Article. (May 2016) 26060. 6. 1. Scientific Reports.

Zheng, Nenggan, Lijuan Su, Daqiang Zhang, Liqiang Gao, Min Yao, and Zhaohui Wu. "A computational model for ratbot locomotion based on cyborg intelligence." Journal Article. (Dec. 2015) 92-97. 170. Neurocomputing.

Sultana, Madeena, Padma Polash Paul, and Marina L. Gavrilova. "Online user interaction traits in web-based social biometrics." Book Section. (2014) 177-190. IGI Global.

Kolb, B., Teskey, G.C. & Gibb, R., Nov. 2010. Factors influencing cerebral plasticity in the normal and injured brain. Frontiers in human neuroscience, 4, p. 204. doi: 10.3389/fnhum.2010.00204.

Paul, P.P. & Marina, G., 2012b. Multimodal Cancelable Biometrics. In 2012 IEEE 11th International Conference on Cognitive Informatics and Cognitive Computing. Available at: http://dx.doi.org/10.1109/icci-cc.2012.6311208.

Hallett, M. & Pascual-Leone, Alvaro & Brasil-Neto, Joaquim & Wassermann, Eric & Cammarota, Noemi. (1993). Plasticity of the Human Motor Cortex. 10.1007/978-3-642-78367-8_6. in lieu of Cohen, L.G. et al., 1993. Plasticity of cortical motor output organization following deafferentation, cerebral lesions, and skill acquisition. Advances in neurology, 63, pp. 187-200.

Economidou, Daina, David E. H. Theobald, Trevor W. Robbins, Barry J. Everitt, and Jeffrey W. Dalley. "Norepinephrine and Dopamine Modulate Impulsivity on the Five-Choice Serial Reaction Time Task Through Opponent Actions in the Shell and Core Sub-Regions of the Nucleus Accumbens" Journal Article. (Aug. 2012) 2057-2066. 37. 9. Neuropsychopharmacology.

Ekerot, Carl-Fredrik, and Henrik Jörntell. "Parallel fiber receptive fields: a key to understanding cerebellar operation and learning." Journal Article. (Jan. 2003) 101-109. 2. 2. The Cerebellum.

Ellrich, Jens, Department of Health Science Professor of Medical Physiology, Medical Faculty Aalborg University Technology, and Medical Department Cerbomed Gmbh Chief Medical Officer. "Transcutaneous Vagus Nerve Stimulation." Journal Article. (2011) 254. 6.4. European Neurological Review.

Engert, Florian, and Tobias Bonhoeffer. "Dendritic spine changes associated with hippocampal long-term synaptic plasticity." Journal Article. (May 1999) 66-70. 399. 6731. Nature.

Falcone, Brian, Brian A. Coffman, Vincent P. Clark, and Raja Parasuraman. "Transcranial Direct Current Stimulation Augments Perceptual Sensitivity and 24-Hour Retention in a Complex Threat Detection Task" Journal Article. (Apr. 2012) e34993. 7. 4. PLoS One.

Fang, Jiliang, Peijing Rong, Yang Hong, Yangyang Fan, Jun Liu, Honghong Wang, Guolei Zhang, Xiaoyan Chen, Shan Shi, Liping Wang, Rupeng Liu, Jiwon Hwang, Zhengjie Li, Jing Tao, Yang Wang, Bing Zhu, and Jian Kong. "Transcutaneous Vagus Nerve Stimulation Modulates Default Mode Network in Major Depressive Disorder." Journal Article. (Feb. 2016) 266-273. 79. 4. Biological Psychiatry.

Fanselow, Michael S. "Fear and Anxiety Take a Double Hit From Vagal Nerve Stimulation." Journal Article. (Jun. 2013) 1043-1044. 73. 11 Biological Psychiatry.

Frangos, Eleni, Jens Ellrich, and Barry R. Komisaruk. "Non-invasive Access to the Vagus Nerve Central Projections via Electrical Stimulation of the External Ear: fMRI Evidence in Humans." Journal Article. (May 2015) 624-636. 8. 3. Brain Stimulation.

Frank, Michael J. "Hold your horses: A dynamic computational role for the subthalamic nucleus in decision making." Journal Article. (Oct. 2006) 1120-1136. 19. 8. Neural Networks.

Frank, Michael J., Bradley B. Doll, Jen Oas-Terpstra, and Francisco Moreno. "Prefrontal and striatal dopaminergic genes predict individual differences in exploration and exploitation." Journal Article. (Aug. 2009) 1062-1068. 12. 8. Nature Neuroscience.

Frank, Michael J., and John A. Fossella. "Neurogenetics and Pharmacology of Learning, Motivation, and Cognition." Journal Article. (Jan. 2011) 133-152. 36. 1. Neuropsychopharmacology.

Frank, Michael J., Randall C. O'Reilly, and Tim Curran. "When Memory Fails, Intuition Reigns: Midazolam Enhances Implicit Inference in Humans." Journal Article. (Aug. 2006) 700-707. 17. 8. Psychological Science.

Fritsch, Brita, Janine Reis, Keri Martinowich, Heidi M. Schambra, Yuanyuan Ji, Leonardo G. Cohen, and Bai Lu. "Direct Current Stimulation Promotes BDNF-Dependent Synaptic Plasticity: Potential Implications for Motor Learning" Journal Article. (Apr. 2010) 198-204. 66. 2. Neuron.

Furmaga, Havan, Aparna Shah, and Alan Frazer. "Serotonergic and Noradrenergic Pathways Are Required for the Anxiolytic-like and Antidepressant-like Behavioral Effects of Repeated Vagal Nerve Stimulation in Rats." Journal Article. (Nov. 2011) 937-945. 70. 10. Biological Psychiatry.

George, Mark S., Herbert E. Ward, Philip T. Ninan, Mark Pollack, Ziad Nahas, Berry Anderson, Samet Kose, Robert H. Howland, Wayne K. Goodman, and James C. Ballenger. "A pilot study of vagus nerve stimulation (VNS) for treatment-resistant anxiety disorders." Journal Article. (Apr. 2008) 112-121. 1. 2. Brain Stimulation.

(56) References Cited

OTHER PUBLICATIONS

Gershenfeld, N., Chen, K. & Dalrymple, D.A., . "Asynchronous logic automata." Conference Proceedings. (Jun. 2008) 313-322. Automata 2008: Theory and Applications of Cellular Automata. Bristol, UK.

Geurts, D. E M., Q. J. M. Huys, H. E. M. Den Ouden, and R. Cools. "Serotonin and Aversive Pavlovian Control of Instrumental Behavior in Humans." Journal Article. (Nov. 2013) 18932-18939. 33. 48. Journal of Neuroscience.

Ghacibeh, Georges A., Joel I. Shenker, Brian Shenal, Basim M. Uthman, and Kenneth M. Heilman. "Effect of vagus nerve stimulation on creativity and cognitive flexibility." Journal Article. (Jun. 2006) 720-725. 8. 4. Epilepsy & Behavior.

Ghacibeh, Georges A., Joel I. Shenker, Brian Shenal, Basim M. Uthman, and Kenneth M. Heilman. "The Influence of Vagus Nerve Stimulation on Memory." Journal Article. (Sep. 2006) 119-122. 19. 3. Cognitive and Behavioral Neurology.

Ghosh, Kunal K., Laurie D. Burns, Eric D. Cocker, Axel Nimmerjahn, Yaniv Ziv, Abbas El Gamal, and Mark J. Schnitzer. "Miniaturized integration of a fluorescence microscope." Journal Article. (Oct. 2011) 871-878. 8. 10. Nature Methods.

Gilbert, Charles D., Mariano Sigman, and Roy E. Crist. "The Neural Basis of Perceptual Learning." Journal Article. (Sep. 2001) 681-697. 31. 5. Neuron.

Gilzenrat, Mark S., Sander Nieuwenhuis, Marieke Jepma, and Jonathan D. Cohen. "Pupil diameter tracks changes in control state predicted by the adaptive gain theory of locus coeruleus function." Journal Article. (Jun. 2010) 252-269. 10. 2. Cognitive, Affective, & Behavioral Neuroscience.

Goadsby, PJ, BM Grosberg, A. Mauskop, R. Cady, and KA Simmons. "Effect of noninvasive vagus nerve stimulation on acute migraine: An open-label pilot study." Journal Article. (Oct. 2014) 986-993. 34. 12. Cephalalgia.

Gould, Elizabeth, Anna Beylin, Patima Tanapat, Alison Reeves, and Tracey J. Shors. "Learning enhances adult neurogenesis in the hippocampal formation." Journal Article. (Mar. 1999) 260-265. 2. 3. Nature Neuroscience.

Gould, Elizabeth, and Charles G. Gross. "Neurogenesis in Adult Mammals: Some Progress and Problems." Journal Article. (Feb. 2002) 619-623.22. 3. The Journal of Neuroscience.

Grafman, Jordan. "Conceptualizing functional neuroplasticity." Journal Article. (Jul. 2000) 345-356. 33. 4. Journal of Communication Disorders.

Gross, Charles G. "Neurogenesis in the adult brain: death of a dogma." Journal Article. (Oct. 2000) 67-73. 1. 1. Nature Reviews Neuroscience.

Gu, L., S. Kleiber, L. Schmid, F. Nebeling, M. Chamoun, J. Steffen, J. Wagner, and M. Fuhrmann. "Long-Term In Vivo Imaging of Dendritic Spines in the Hippocampus Reveals Structural Plasticity." Journal Article. (Oct. 2014) 13948-13953. 34. 42. Journal of Neuroscience.

Hallett, M., L. G. Cohen, A. Pascual-Leone, J. Brasil-Neto, E. M. Wassermann, and A. N. Cammarota. "Plasticity of the Human Motor Cortex." Book Section. (1993) 67-81. Issue. Journal.

Hamlat, Abderrahmane, Mahmoudreza Adn, Sylvie Caulet-Maugendre, and Yvon Guegan. "Cerebellar Malignant Fibrous Histiocytoma: Case Report and Literature Review." Journal Article. (Mar. 2004) 745-752. 64. 3. Neurosurgery.

Hamlat, Abderrahmane, Mahmoudreza Adn, Edouardo Pasqualini, Gilles Brassier, and Brahim Askar. "Pathophysiology of capillary haemangioma growth after birth." Journal Article. (Jan. 2005) 1093-1096. 64. 6. Medical Hypotheses.

Hamlat, Abderrahmane, Mahmoudreza Adn, Seddik Sid-Ahmed, Brahim Askar, and Edouardo Pasqualini. "Theoretical considerations on the pathophysiology of normal pressure hydrocephalus (NPH) and NPH-related dementia." Journal Article. (Jan. 2006) 115-123. 67. 1. Medical Hypotheses.

Ide, J. S., P. Shenoy, A. J. Yu, and C. S R. Li. "Bayesian Prediction and Evaluation in the Anterior Cingulate Cortex." Journal Article. (Jan. 2013) 2039-2047. 33. 5. Journal of Neuroscience.

Hamlat, Abderrahmane, Anne Heckly, Mahmoudreza Adn, and Patrice Poulain. "Pathophysiology of intracranial epidural haematoma following birth." Journal Article. (Jan. 2006) 371-374. 66. 2. Medical Hypotheses.

Hamlat, Abderrahmane, Zhi-Fen Hua, Stephan Saikali, Jean François Laurent, Daniel Gedouin, Mohamed Ben-Hassel, and Yvon Guegan. "Malignant Transformation of Intra-Cranial Epithelial Cysts: Systematic Article Review." Journal Article. (Sep. 2005) 187-194. 74. 2. Journal of Neuro-Oncology.

Hamlat, Abderrahmane, Anne Le Strat, Yvon Guegan, Mohamed Ben-Hassel, and Stephan Saikali. "Cerebellar pleomorphic xanthoastrocytoma: case report and literature review." Journal Article. (Jul. 2007) 89-94. 68. 1. Surgical Neurology.

Hamlat, Abderrahmane, and Eduardo Pasqualini. "Stem cells adaptive network: Mechanism and implications for evolution and disease development." Journal Article. (Jan. 2007) 610-617. 69. 3. Medical Hypotheses.

Hamlat, Abderrahmane, Eduardo Pasqualini, and Brahim Askar. "Hypothesis about the physiopathology of acute deterioration and sudden death caused by colloid cysts of the third ventricle." Journal Article. (Jan. 2004) 1014-1017. 63. 6. Medical Hypotheses.

Hamlat, Abderrahmane, Stephan Saikali, Jacques Chaperon, Michèle Le Calve, Daniel Gedouin, Mohamed Ben-Hassel, and Yvon Guegan. "Oligodendroglioma: clinical study and survival analysis correlated with chromosomal anomalies." Journal Article. (Nov. 2005) 1-9. 19. 5. Neurosurgical Focus.

Hamlat, Abderrahmane, Seddik Sid-Ahmed, Mahmoudreza Adn, Brahim Askar, and Edouardo Paqualini. "Idiopathic normal pressure hydrocephalus: Theoretical concept of a spinal etiology." Journal Article. (Jan. 2006) 110-114. 67. 1. Medical Hypotheses.

Hays, Seth A., Robert L. Rennaker, and Michael P. Kilgard. "Targeting Plasticity with Vagus Nerve Stimulation to Treat Neurological Disease." Book Section. (2013) 275-299. 207. Issue. Journal.

Hazy, Thomas E., Michael J. Frank, and Randall C. O'Reilly. "Towards an executive without a homunculus: computational models of the prefrontal cortex/basal ganglia system." Journal Article. (Sep. 2007) 1601-1613. 362. 1485. Philosophical Transactions of the Royal Society B: Biological Sciences.

Hikosaka, Okihide, Kae Nakamura, Katsuyuki Sakai, and Hiroyuki Nakahara. "Central mechanisms of motor skill learning." Journal Article. (Apr. 2002) 217-222. 12. 2. Current Opinion in Neurobiology.

Hong, S. Lee, and George V. Rebec. "A new perspective on behavioral inconsistency and neural noise in aging: compensatory speeding of neural communication." Journal Article. (2012) 4. Frontiers in Aging Neuroscience.

Hong, S. Lee, and George V. Rebec. "Biological sources of inflexibility in brain and behavior with aging and neurodegenerative diseases." Journal Article. (2012) 6. Frontiers in Systems Neuroscience.

Horner, Philip J., and Fred H. Gage. "Regenerating the damaged central nervous system." Journal Article. (Oct. 2000) 963-970. 407. 6807. Nature.

Huang, Yanping, and Rajesh P. N. Rao. "Reward Optimization in the Primate Brain: A Probabilistic Model of Decision Making under Uncertainty." Journal Article. (Jan. 2013) e53344. 8. 1. PLoS One.

Huettel, S. A. "Decisions under Uncertainty: Probabilistic Context Influences Activation of Prefrontal and Parietal Cortices." Journal Article. (Mar. 2005) 3304-3311. 25. 13. Journal of Neuroscience.

Hung, Shao-Chin, and Aaron R. Seitz. "Retrograde Interference in Perceptual Learning of a Peripheral Hyperacuity Task." Journal Article. (Sep. 2011) e24556. 6. 9. PLoS One.

Ito, Masao. "Adaptive Control of Reflexes by the Cerebellum." Book Section. (1976) 435-444. Elsevier.

Orrin, S. "The SOA/XML Threat Model and New XML/SOA/Web 2.0 Attacks & Threats." Website. (2007) Intel Corporation. Retrieved from: https://www.defcon.org/images/defcon-15/dc15-presentations/dc-15-orrin.pdf.

Jacobs, Heidi I. L., Joost M. Riphagen, Chantalle M. Razat, Svenja Wiese, and Alexander T. Sack. "Transcutaneous vagus nerve stimulation boosts associative memory in older individuals." Journal Article. (May 2015) 1860-1867. 36. 5. Neurobiology of Aging.

(56) References Cited

OTHER PUBLICATIONS

Kano, Masanobu, and Makoto Kato. "The long-term depression of parallel Fiber-Purkinje cell transmission induced by conjunctive local glutamate application with climbing fiber stimulation in the cerebellar cortex of the rabbit." Journal Article. (Jan. 1985) S126. 1. Neuroscience Research Supplements.

Köhler, Per, Anette Wolff, Fredrik Ejserholm, Lars Wallman, Jens Schouenborg, and Cecilia E. Linsmeier. "Influence of Probe Flexibility and Gelatin Embedding on Neuronal Density and Glial Responses to Brain Implants." Journal Article. (Mar. 2015) e0119340. 10. 3. PLoS One.

Koziol, Leonard F., Deborah Buuding, Nancy Andreasen, Stefano D'Arrigo, Sara Bulgheroni, Hiroshi Imamizu, Masao Ito, Mario Manto, Cherie Marvel, Krystal Parker, Giovanni Pezzulo, Narender Ramnani, Daria Riva, Jeremy Schmahmann, Larry Vandervert, and Tadashi Yamazaki. "Consensus Paper: The Cerebellum's Role in Movement and Cognition." Journal Article. (Feb. 2014) 151-177. 13. 1. The Cerebellum.

Kraus, Thomass, Olga Kiess, Katharina Hösl, Pavel Terekhin, Johannes Kornhuber, and Clemens Forster. "CNS Bold fMRI Effects of Sham-Controlled Transcutaneous Electrical Nerve Stimulation in the Left Outer Auditory Canal—A Pilot Study." Journal Article. (Sep. 2013) 798-804. 6. 5. Brain Stimulation.

Kreuzer, Peter M., Michael Landgrebe, Oliver Husser, Markus Resch, Martin Schecklmann, Florian Geisreiter, Timm B. Poeppl, Sarah Julia Prasser, Goeran Hajak, and Berthold Langguth. "Transcutaneous Vagus Nerve Stimulation: Retrospective Assessment of Cardiac Safety in a Pilot Study." Journal Article. (2012) 3. Frontiers in Psychiatry.

Krigolson, Olav E., and Clay B. Holroyd. "Hierarchical error processing: Different errors, different systems." Journal Article. (Jun. 2007) 70-80. 1155. Brain Research.

Lalonde, Robert. "Cerebellar contributions to instrumental learning." Journal Article. (Jun. 1994) 161-170. 18. 2. Neuroscience & Biobehavioral Reviews.

Lamprecht, Raphael, and Joseph Ledoux. "Structural plasticity and memory." Journal Article. (Jan. 2004) 45-54. 5. 1. Nature Reviews Neuroscience.

Liepert, J., M. Tegenthoff, and J. P. Malin. "Changes of cortical motor area size during immobilization." Journal Article. (Dec. 1995) 382-386. 97. 6. Electroencephalography and Clinical Neurophysiology/Electromyography and Motor Control.

Liu, Ai-Fen, Feng-Bo Zhao, Jing Wang, Yi-Fan Lu, Jian Tian, Yin Zhao, Yan Gao, Xia-Jun Hu, Xiao-Yan Liu, Jie Tan, Yun-Li Tian, and Jing Shi. "Effects of vagus nerve stimulation on cognitive functioning in rats with cerebral ischemia reperfusion." Journal Article. (Dec. 2016) 101. 14. 1. Journal of Translational Medicine.

Lomber, Stephen G., and Bertram R. Payne. "Task-specific reversal of visual hemineglect following bilateral reversible deactivation of posterior parietal cortex: A comparison with deactivation of the superior colliculus." Journal Article. (May 2001) 487-499. 18. 3. Visual Neuroscience.

Magis, D., R Gérard, and J. Schoenen. "Transcutaneous Vagus Nerve Stimulation (tVNS) for headache prophylaxis: initial experience." Journal Article. (Feb. 2013) P198,-1129-2377-1114-S1121-P1198. 14. S1. The Journal of Headache and Pain.

Maletic-Savatic, M. "Rapid Dendritic Morphogenesis in CA1 Hippocampal Dendrites Induced by Synaptic Activity." Journal Article. (Mar. 1999) 1923-1927.283. 5409. Science.

Manta, Stella, Jianming Dong, Guy Debonnel, and Pierre Blier. "Optimization of vagus nerve stimulation parameters using the firing activity of serotonin neurons in the rat dorsal raphe." Journal Article. (Apr. 2009) 250-255. 19. 4. European Neuropsychopharmacology.

Mariën, Peter, and Alan Beaton. "The enigmatic linguistic cerebellum: clinical relevance and unanswered questions on nonmotor speech and language deficits in cerebellar disorders." Journal Article. (Dec. 2014) 12. 1. 1. Cerebellum & Ataxias.

Matthews, R., P. J. Turner, N. J. McDonald, K. Ermolaev, T. Mc Manus, R. A. Shelby, and M. Steindorf. "Real time workload classification from an ambulatory wireless EEG system using hybrid EEG electrodes." Conference Proceedings. (Aug. 2008) 5871-5875. 2008 30th Annual International Conference of the IEEE Engineering in Medicine and Biology Society.

McClure, Samuel M., Mark S. Gilzenrat, and Jonathan D. Cohen. "An exploration-exploitation model based on norepinepherine and dopamine activity." Conference Proceedings. (2006) 867-874.

McIntyre, Christa K., James L. McGaugh, and Cedric L. Williams. "Interacting brain systems modulate memory consolidation." Journal Article. (Aug. 2012) 1750-1762. 36. 7. Neuroscience & Biobehavioral Reviews.

Messerer, Mahmoud, Julie Dubourg, Sylma Diabira, Thomas Robert, and Abderrahmane Hamlat. "Spinal epidural hematoma: not always an obvious diagnosis." Journal Article. (Feb. 2012)2-8. 19. 1. European Journal of Emergency Medicine.

Milad, Mohammed R., Roger K. Pitman, Cameron B. Ellis, Andrea L. Gold, Lisa M. Shin, Natasha B. Lasko, Mohamed A. Zeidan, Kathryn Handwerger, Scott P. Orr, and Scott L. Rauch. "Neurobiological Basis of Failure to Recall Extinction Memory in Posttraumatic Stress Disorder." Journal Article. (Dec. 2009) 1075-1082. 66. 12. Biological Psychiatry.

Murphy, Peter R., Redmond G. O'Connell, Michael O'Sullivan, Ian H. Robertson, and Joshua H. Balsters. "Pupil diameter covaries with Bold activity in human locus coeruleus." Journal Article. (Aug. 2014) 4140-4154. 35. 8. Human Brain Mapping.

Nelson, Jeremy T., R. Andy McKinley, Edward J. Golob, Joel S. Warm, and Raja Parasuraman. "Enhancing vigilance in operators with prefrontal cortex transcranial direct current stimulation (tDCS)." Journal Article. (Jan. 2014) 909-917. 85. NeuroImage.

Nemeroff, Charles B., Helen S. Mayberg, Scott E. Krahl, James McNamara, Alan Frazer, Thomas R. Henry, Mark S. George, Dennis S. Charney, and Stephen K. Brannan. "VNS Therapy in Treatment-Resistant Depression: Clinical Evidence and Putative Neurobiological Mechanisms." Journal Article. (Jul. 2006) 1345-1355. 31. 7. Neuropsychopharmacology.

Nesbitt, AD, JCA Marin, E. Tomkins, MH Ruttledge, and PJ Goadsby. "Non-invasive vagus nerve stimulation for the treatment of cluster headache: a case series." Journal Article. (Feb. 2013) P231,-1129-2377-1114-S1121-P1231. 14. S1. The Journal of Headache and Pain.

Nieuwenhuis, Sander, Gary Aston-Jones, and Jonathan D. Cohen. "Decision making, the P3, and the locus coeruleus—norepinephrine system." Journal Article. (2005) 510-532. 131. 4. Psychological Bulletin.

Nieuwenhuis, Sander, Mark S. Gilzenrat, Benjamin D. Holmes, and Jonathan D. Cohen. "The Role of the Locus Coeruleus in Mediating the Attentional Blink: A Neurocomputational Theory." Journal Article. (2005) 291-307. 134. 3. Journal of Experimental Psychology: General.

Noroozian, Maryam. "The Role of the Cerebellum in Cognition." Journal Article. (Nov. 2014) 1081-1104. 32. 4. Neurologic Clinics.

O'Keane, Veronica, Ted G. Dinan, Lucinda Scott, and Ciaran Corcoran. "Changes in Hypothalamic-Pituitary—Adrenal Axis Measures After Vagus Nerve Stimulation Therapy in Chronic Depression." Journal Article. (Dec. 2005) 963-968. 58. 12. Biological Psychiatry.

Padma Polash, Paul, and MD Maruf Monwar. "Human iris recognition for biometric identification." Conference Proceedings. (Dec. 2007) 1-5. 2007 10th International Conference on Computer and Information Technology (ICCIT 2007).

Parasuraman, Raja. "Neuroergonomics: Brain, Cognition, and Performance at Work." Journal Article. (Jun. 2011) 181-186. 20. 3. Current Directions in Psychological Science.

Parasuraman, Raja, and Yang Jiang. "Individual differences in cognition, affect, and performance: Behavioral, neuroimaging, and molecular genetic approaches." Journal Article. (Jan. 2012) 70-82. 59. 1. NeuroImage.

Parasuraman, Raja, and Dietrich H. Manzey. "Complacency and Bias in Human Use of Automation: An Attentional Integration." Journal Article. (Jun. 2010) 381-410. 52. 3. Human Factors: The Journal of the Human Factors and Ergonomics Society.

Park, M. C., M. A. Goldman, L. L. Carpenter, L. H. Price, and Gerhard M. Friehs. "Vagus nerve stimulation for depression: ratio-

(56) References Cited

OTHER PUBLICATIONS nale, anatomical and physiological basis of efficacy and future prospects." Book Section. (2007) 407-416. Springer Vienna. Vienna.

Pascual-Leone, Alvaro, Catarina Freitas, Lindsay Oberman, Jared C. Horvath, Mark Halko, Mark Eldaief, Shahid Bashir, Marine Vernet, Mouhshin Shafi, Brandon Westover, Andrew M. Vahabzadeh-Hagh, and Alexander Rotenberg. "Characterizing Brain Cortical Plasticity and Network Dynamics Across the Age-Span in Health and Disease with TMS-EEG and TMS-fMRI." Journal Article. (Oct. 2011) 302-315. 24. 3-4. Brain Topography.

Pascual-Leone, A., J. Grafman, and M. Hallett. "Modulation of cortical motor output maps during development of implicit and explicit knowledge." Journal Article. (Mar. 1994) 1287-1289. 263. 5151. Science.

Pascual-Leone, A., D. Nguyet, L. G. Cohen, J. P. Brasil-Neto, A. Cammarota, and M. Hallett. "Modulation of muscle responses evoked by transcranial magnetic stimulation during the acquisition of new fine motor skills." Journal Article. (Sep. 1995) 1037-1045. 74. 3. Journal of Neurophysiology.

Pascual-Leone, A., M. Peris, J. M. Tormos, A. Pascual-Leone Pascual, and M. D. Catalá. "Reorganization of human cortical motor output maps following traumatic forearm amputation." Journal Article. (Sep. 1996) 2068-2070. 7. 13. NeuroReport.

Pascual-Leone, Alvaro, Francisco Tarazona, Julian Keenan, Jose M. Tormos, Roy Hamilton, and Maria D. Catala. "Transcranial magnetic stimulation and neuroplasticity." Journal Article. (Nov. 1998) 207-217. 37. 2. Neuropsychologia.

Paul, Padma Polash, and Marina Gavrilova. "PCA Based Geometric Modeling for Automatic Face Detection." Conference Proceedings. (Jun. 2011) 33-38. 2011 International Conference on Computational Science and its Applications (ICCSA).

Paul, Padma Polash, and Marina Gavrilova. "Multimodal biometric approach for cancelable face template generation." Conference Proceedings. (May 2012) 84070H-84070H-84077. SPIE Defense, Security, and Sensing.

Paul, Padma Polash, and Marina Gavrilova. "Novel multimodal template generation algorithm." Conference Proceedings. (Jul. 2013) 76-82. 2013 12th IEEE International Conference on Cognitive Informatics & Cognitive Computing (ICCI*CC).

Paul, Padma Polash, and Marina Gavrilova. "Multimodal Biometrics Using Cancelable Feature Fusion." Conference Proceedings. (Oct. 2014) 279-284. 2014 International Conference on Cyberworlds (CW).

Paul, Padma Polash, Madeena Sultana, Sorin Adam Matei, and Marina Gavrilova. "Editing Behavior to Recognize Authors of Crowdsourced Content." Conference Proceedings. (Oct. 2015) 1676-1681. 2015 IEEE International Conference on Systems, Man, and Cybernetics (SMC).

Paul, Padma Polash, Marina Gavrilova, and Stanslav Klimenko. "Situation Awareness through Multimodal Biometric Template Security in Real-Time Environments." Conference Proceedings. (Oct. 2013) 82-88. 2013 International Conference on Cyberworlds (CW).

Paul, Padma Polash, Marina Gavrilova, and Stanislav Klimenko. "Situation awareness of cancelable biometric system." Journal Article. (Sep. 2014) 1059-1067. 30. 9. The Visual Computer.

Paul, Padma Polash, MD Maruf Monwar, and Marina L. Gavrilova. "Face Detection Using Skin Color Recursive Clustering and Recognition Using Multilinear PCA." Conference Proceedings. (Oct. 2011) 100-105. 2011 International Conference on Cyberworlds (CW).

Pena, David Frausto, Jessica E. Childs, Shawn Willett, Analicia Vital, Christa K. McIntyre, and Sven Kroener. "Vagus nerve stimulation enhances extinction of conditioned fear and modulates plasticity in the pathway from the ventromedial prefrontal cortex to the amygdala." Journal Article. (Sep. 2014) 8. Frontiers in Behavioral Neuroscience.

\* cited by examiner

TRANSCUTANEOUS ELECTRICALLY AMPLIFIED COGNITIVE ENHANCEMENT SYSTEM

CROSS-REFERENCE TO RELATED APPLICATIONS

This application claims the benefit of U.S. Provisional Application No. 62/685,643, filed Jun. 15, 2018, the contents of which are incorporated herein in their entirety.

BACKGROUND

The present invention relates to systems and methods for stimulating the modification of synapses to enhance the speed and quality of cognitive brain function Although every human brain has the same basic anatomical structure, each one performs quite differently at every organizational layer, down to the subatomic. The cortical structure and its six layers of 3 dimensional foldings are structurally the same, yet functionally quite different. The consistency of these structures ironically leads to heterogeneity (intelligence, personality, talent etc.). For these reasons and many others, plasticity is not an easy point of arrival, but it is indeed a scientific point of departure. When humans or animals learn something, synapses are strengthened or pruned, dendrites branch out to make new connections, and blood vessels and support cells grow to support the change.

Accordingly, a need arises for techniques that can stimulate the modification of synapses to enhance the speed and quality of cognitive brain function.

SUMMARY

Embodiments of the present systems and methods may provide the capability to stimulate nerve activity using transcutaneous nerve stimulation, as well as monitor nerve activity through the skin. Various branches of the nervous system may be accessed at various points on the body. For example, the ulnar nerve may be accessed at the elbow, for both stimulation and monitoring. Likewise, the vagal nerve may be accessed via the ear canal, for both stimulation and monitoring. While embodiments of the present systems and methods may be described with reference to particular nerves or nervous system branches, and to particular points on the body, it is to be understood that embodiments may be applied to any nerves or nervous system branches and to any points on the body.

Embodiments of the present systems and methods may use combinations of transcutaneous vagal nerve stimulation (tVNS) and transcutaneous electrical nerve stimulation (TENS) on selected target areas to enhance synaptic plasticity and increase ability to learn new skills, comprehend new ideas and make more effective decisions, especially in high uncertainty task conditions.

For example, in an embodiment, a system for monitoring and stimulating human body activity and conditions may comprise at least one transcutaneous nerve stimulation circuitry comprising a circuitry adapted to generate a nerve stimulation signal and at least one electrode or contact adapted to apply the nerve stimulation signal to a nerve of a human through a skin of the human, transcutaneous electrical nerve monitoring circuitry comprising a circuitry adapted to monitor at least one nerve signal received from at least one sensor adapted to obtain the at least one nerve signal from a human through the skin of the human, and control circuitry adapted to control signal generation and signal application of the transcutaneous nerve stimulation circuitry.

In embodiments, there may be a plurality of transcutaneous nerve stimulation circuitries. A first transcutaneous nerve stimulation circuitry may comprise transcutaneous vagal nerve stimulation circuitry comprising circuitry adapted to generate a vagal nerve stimulation signal and at least one electrode or contact adapted to apply the vagal nerve stimulation signal to a vagal nerve of a human through the skin of the human, a second transcutaneous nerve stimulation circuitry may comprise transcutaneous electrical nerve stimulation circuitry comprising a circuitry adapted to generate a transcutaneous electrical nerve stimulation signal and at least one electrode or contact adapted to apply the transcutaneous electrical nerve stimulation to a human through the skin of the human, and the control circuitry may be adapted to control signal generation and signal application of the transcutaneous vagal nerve stimulation circuitry and the transcutaneous electrical nerve stimulation circuitry.

The at least one electrode or contact adapted to apply the vagal nerve stimulation signal to a vagal nerve of a human may be adapted to apply the vagal nerve stimulation signal to an auricular branch of a vagus nerve in a cymba conchae of an ear of the human. At least the transcutaneous vagal nerve stimulation circuitry and the at least one vagal nerve stimulation electrode or contact may be included in an ear-mounted device adapted to be at least partially inserted in the ear of the human. The system may further comprise wireless communication circuitry adapted to provide communication with the control circuitry. The transcutaneous electrical nerve stimulation circuitry and the transcutaneous electrical nerve stimulation electrode or contact may be included in a device adapted to be attached to a body of the human and the transcutaneous electrical nerve stimulation circuitry may be adapted to communicate with the control circuitry using the wireless communication circuitry. The system may further comprise at least one sensor selected from a group comprising: audio sensors, video sensors, EEG sensors, ECG sensors, heart rate sensors, breathing rate sensors, blood pressure sensors, body temperature sensors, head movement sensors, body posture sensors, and blood oxygenation levels sensors. The system may further comprise a computing device adapted to wirelessly communicate with the control circuitry via the wireless communication circuitry. The system may further comprise at least one server computer system adapted to communicate with the computing device. The system may further comprise a helmet adapted to be worn on a head of the human, the helmet comprising: at least one sensor selected from a group comprising: audio sensors, video sensors, EEG sensors, ECG sensors, heart rate sensors, breathing rate sensors, blood pressure sensors, body temperature sensors, head movement sensors, body posture sensors, and blood oxygenation levels sensors and wireless communications circuitry adapted to provide communications with at least one ear-mounted device and at least one computing device. The electrode or contact may comprise at least one of a carbon nanotube or graphene.

In an embodiment, a method for monitoring and stimulating human body activity and conditions may comprise generating, at control circuitry, control signals to control signal generation and signal application of at least one transcutaneous nerve stimulation signal and control signals to control monitoring of at least one nerve signal, generating, at at least one transcutaneous nerve stimulation circuitry, under control of the controls signals, at least one nerve stimulation signal and transmitting the generated at least one nerve stimulation signal to at least one electrode or contact adapted to apply the nerve stimulation signal to a nerve of a human through the skin of the human, and monitoring, at transcutaneous electrical nerve monitoring circuitry, under control of the controls signals, at least one nerve signal received from at least one sensor adapted to obtain the at least one nerve signal from a human through the skin of the human.

In embodiments, there may be a plurality of transcutaneous nerve stimulation circuitries. The method may further comprise generating, at the control circuitry, control signals to control signal generation and signal application of the transcutaneous vagal nerve stimulation signals and the transcutaneous electrical nerve stimulation signals, generating, at a first transcutaneous nerve stimulation circuitry comprising transcutaneous vagal nerve stimulation circuitry, under control of the controls signals, a vagal nerve stimulation signal and transmitting the generated vagal nerve stimulation signal to at least one electrode or contact adapted to apply the vagal nerve stimulation signal to a vagal nerve of a human through the skin of the human, and generating, at a second transcutaneous nerve stimulation circuitry comprising transcutaneous electrical nerve stimulation circuitry, under control of the controls signals, a transcutaneous electrical nerve stimulation signal and transmitting the generated transcutaneous electrical nerve stimulation signal to at least one electrode or contact adapted to apply the transcutaneous electrical nerve stimulation to a human through the skin of the human In embodiments, the at least one electrode or contact adapted to apply the vagal nerve stimulation signal to a vagal nerve of a human may be adapted to apply the vagal nerve stimulation signal to an auricular branch of a vagus nerve in a cymba conchae of an ear of the human. At least the transcutaneous vagal nerve stimulation circuitry and the at least one vagal nerve stimulation electrode or contact are included in an ear-mounted device adapted to be at least partially inserted in the ear of the human. The method may further comprise communicating with the control circuitry using wireless communication circuitry. The transcutaneous electrical nerve stimulation circuitry and the transcutaneous electrical nerve stimulation electrode or contact may be included in a device adapted to be attached to a body of the human and the transcutaneous electrical nerve stimulation circuitry is adapted to communicate with the control circuitry using the wireless communication circuitry. The method may further comprise monitoring at least one physical or physiological condition of the human using at least one sensor selected from a group comprising: audio sensors, video sensors, EEG sensors, ECG sensors, heart rate sensors, breathing rate sensors, blood pressure sensors, body temperature sensors, head movement sensors, body posture sensors, and blood oxygenation levels sensors. The method may further comprise communicating with a computing device via the wireless communication circuitry. The method may further comprise communicating with at least one server computer system adapted to communicate with the computing device. The method may further comprise monitoring at least one physical or physiological condition of the human using a helmet adapted to be worn on a head of the human, the helmet comprising at least one sensor selected from a group comprising: audio sensors, video sensors, EEG sensors, ECG sensors, heart rate sensors, breathing rate sensors, blood pressure sensors, body temperature sensors, head movement sensors, body posture sensors, and blood oxygenation levels sensors and communicating with at least one ear-mounted device and at least one computing device using wireless communications circuitry included in the helmet.

BRIEF DESCRIPTION OF THE DRAWINGS

The details of the present invention, both as to its structure and operation, can best be understood by referring to the accompanying drawings, in which like reference numbers and designations refer to like elements.

DETAILED DESCRIPTION

Embodiments of the present systems and methods may provide the capability to stimulate nerve activity using transcutaneous nerve stimulation, as well as monitor nerve activity through the skin. Various branches of the nervous system may be accessed at various points on the body. For example, the ulnar nerve may be accessed at the elbow, for both stimulation and monitoring. Likewise, the vagal nerve may be accessed via the ear canal, for both stimulation and monitoring. While embodiments of the present systems and methods may be described with reference to particular nerves or nervous system branches, and to particular points on the body, it is to be understood that embodiments may be applied to any nerves or nervous system branches and to any points on the body.

For example, embodiments of the present systems and methods may use combinations of transcutaneous vagal nerve stimulation (tVNS) and transcutaneous electrical nerve stimulation (TENS) on selected target areas to enhance synaptic plasticity and increase ability to learn new skills, comprehend new ideas and make more effective decisions, especially in high uncertainty task conditions.

Embodiments may target, for example, three cognitive skills:

Motor Function—any activity or movement that requires the use of motor neurons including motor acquisition/adaptation.

Cognitive Flexibility—The mental ability to adapt one's cognitive processes to deal with new environments, new concepts, and multiple concepts simultaneously (Scott 1962; Cañas et al. 2003).

Verbal Skills (humans only)—The ability to predict sentence structure given concordant/discordant verb/agent combinations enabling better error-processing in language. Additionally, investigate possible neural mechanism behind one way brain may override prepotent biases in language thus facilitating acquisition of new language skills.

Figure 1:
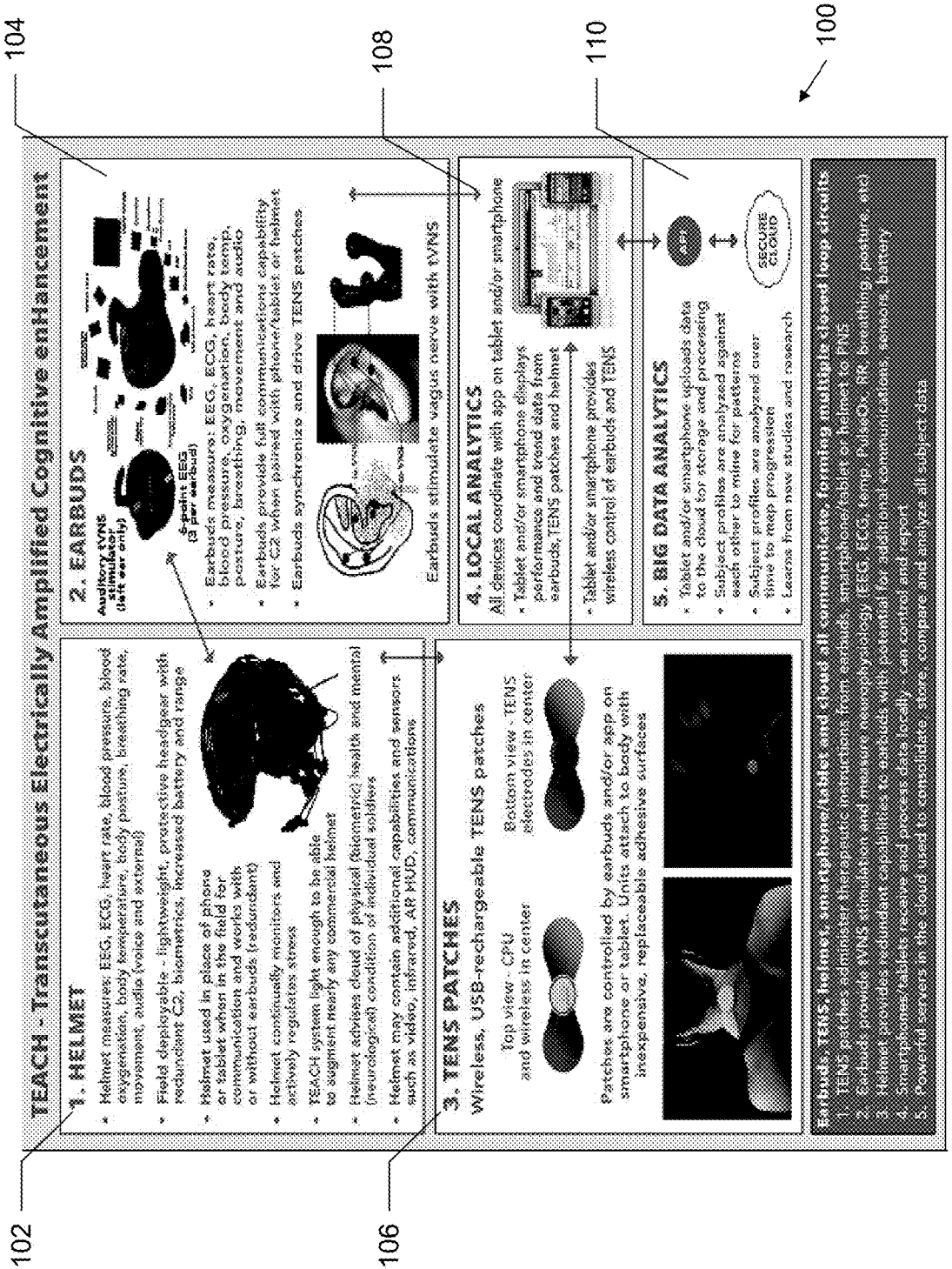
FIG. 1 is an exemplary diagram of an intelligent, closed-loop learning enhancement system according to embodiments of the present systems and methods.

Embodiments of the present systems and methods may include an intelligent, closed-loop learning enhancement system 100, shown in FIG. 1, which may use multiple methods of noninvasive stimulation to promote synaptic plasticity and increase learning performance. For example, embodiments may include one or more earbuds 104 with transcutaneous vagal nerve stimulation (tVNS) and recording capabilities, such as electroencephalogram (EEG) capabilities, a plurality of transcutaneous electrical nerve stimulation (TENS) patches 106, and a customized helmet 102, which may be equipped with a range of sensors and stimulators. The entire system may wireless and securely controlled by software running on, for example, a smartphone or tablet, which may communicate with a cloud platform for automated deep machine learning analysis.

In embodiments, helmet 102 may include sensors to measure physical and physiological parameters such as EEG, ECG, heart rate, blood pressure, blood oxygenation, body temperature, body posture, breathing rate, movement, audio (voice and external). In embodiments, helmet 102 may be field deployable, lightweight, protective headgear with redundant C2, biometrics, increased battery, and range. In embodiments, helmet 102 may be used in place of a phone or tablet when in the field for communication and may works with or without earbud 104. In embodiments, helmet 102 may monitors and actively regulates stress, communicate physical (biometric) health and mental (neurological) condition of individuals. In embodiments, helmet 102 may include additional capabilities and sensors T such as video, infrared, AR HUD, communications, etc.

In embodiments, earbuds 104 may include auditory and tVNS stimulators, although, as explained below, the tVNS stimulator may only be included in the left earbud. Embodiments may include, for example, 6-point EEG sensors, 3 per earbud, as well as sensors to measure ECG, heart rate, blood pressure, oxygenation, body temp, posture, breathing, movement, and audio. In embodiments, earbuds 104 may provide full communications capability for C2 when paired with a phone/tablet or helmet 102. In embodiments, earbuds 104 may synchronize and drive TENS patches 106 and stimulate the vagus nerve with tVNS.

In embodiments, TENS patches 106 may provide wireless communications and be rechargeable, for example, using a USB port. In embodiments, TENS patches 106 may include a controller (CPU) and wireless communication circuitry, as well as TENS electrodes. In embodiments, TENS patches 106 may be controlled by earbuds 104 and/or an app on a smartphone or tablet. Units may attach to the body with inexpensive, replaceable adhesive surfaces.

In embodiments, local analytics may be provided by a computing device such as a smartphone, tablet, etc. 108 communicating with helmet 102, earbuds 104, and or TENS patches 106. In embodiments, helmet 102, earbuds 104, and or TENS patches 106 may coordinate with an app on tablet and/or smartphone 108. The tablet and/or smartphone 108 may display performance and trend data from helmet 102, earbuds 104, and or TENS patches 106 and may provide wireless control of helmet 102, earbuds 104, and or TENS patches 106.

In embodiments, big data analytics may be provided by secure servers and/or secure cloud-based processing and storage 110. The tablet and/or smartphone 108 may upload data to the cloud 110 for storage and processing. Subject profiles may be analyzed against each other to mine for patterns. Subject profiles may be analyzed over time to map progression. The analytics may learn from new studies and research.

In embodiments, earbuds 104, TENS 106, helmet 102, smartphone/tablet 108, and cloud 110 may all communicate, forming multiple closed loop processing circuits. TENS patches 106 may administer therapeutic instructions from earbuds 104, smartphone/tablet 108, or helmet 102 to a human subject. Earbuds 104 may provide tVNS stimulation and measure neurophysiology (EEG. ECG, temp, PulseOx, RR, breathing, posture, etc.) Helmet 102 may provide redundant capabilities to earbuds with the potential for additional communications, sensors, battery, etc. Smartphones/tablets 108 may receive and process data locally, and may control the other devices, receive, and analyze data from the devices, and report on the received data. Powerful servers in the cloud 110 may be used to consolidate, store, compare, and analyze all subject data.

Embodiments may be lightweight, wearable for extended periods of time and useful both in the classroom and in the field, as the user may wear either the earbuds alone or in combination with the helmet, which augments the battery and increases range with Wi-Fi. The system may include commercial-off-the-shelf (COTS) devices and/or custom or customizable components. Embodiments may use a suite of software based on the Fundamental Code Unit (FCU) and the Brain Code (BC) theorems, as described, for example, in U.S. Pat. No. 10,154,812, the contents of which are incorporated by reference herein in their entirety. The FCU provides a common mathematical framework for analyzing aggregate data-streams and formulating feedback instructions for optimal neuro-modulation in near real-time.

In embodiments, sensors and stimulators may include electrodes, contacts, etc. made from a variety of materials, including, but not limited to carbon nanotubes (CNT), graphene, etc.

Figure 2:
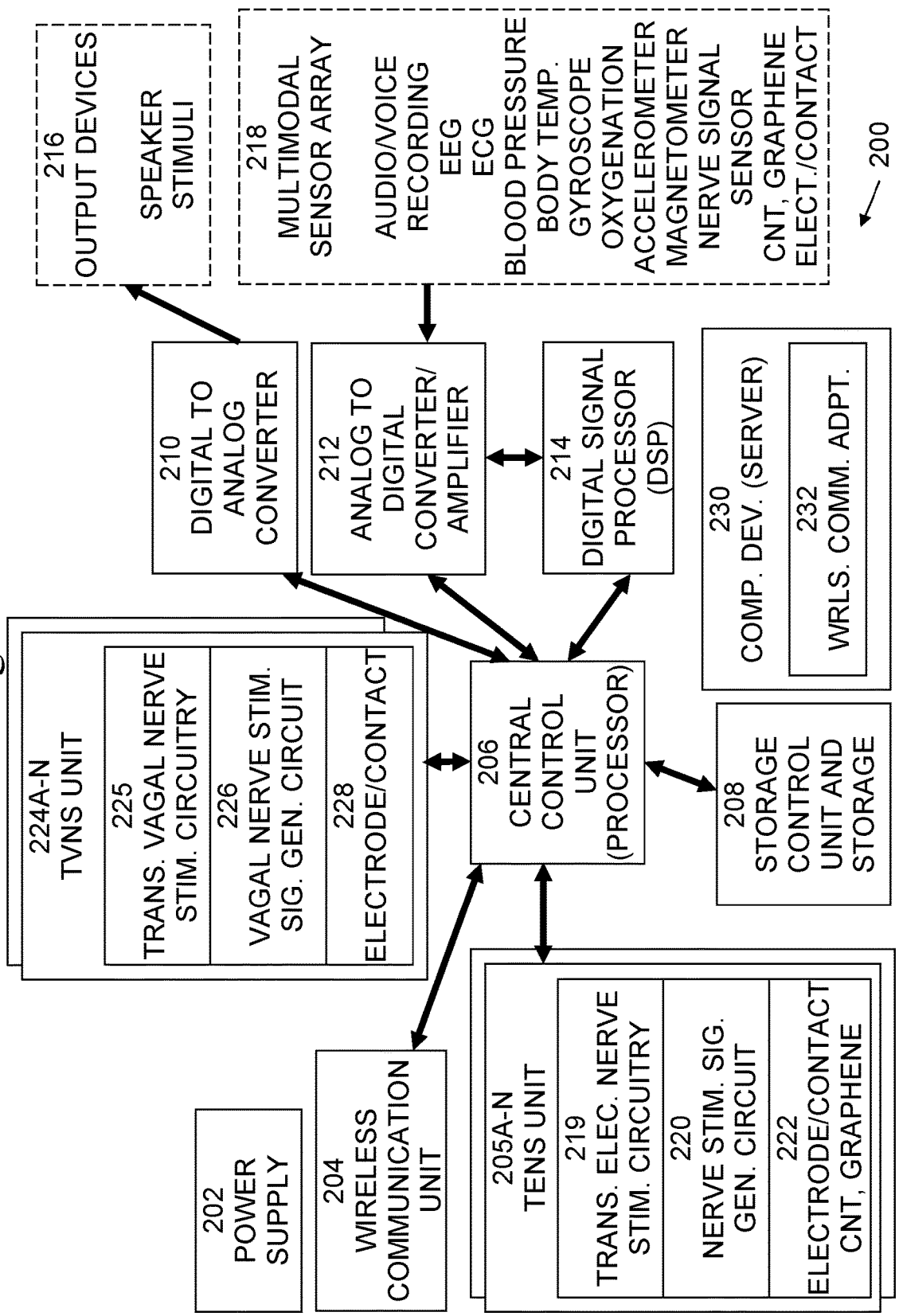
FIG. 2 is an exemplary diagram of a system according to embodiments of the present systems and methods.

An exemplary block diagram of a system 200 according to embodiments of the present systems and methods is shown in FIG. 2. In this example, system 200 may include power supply 202, wireless communication unit 204, one or more TENS units 205A-N, central control unit (processor) 206, storage control unit and storage 208, digital to analog converter (DAC) 210, analog to digital converter (ADC)/amplifier 212, digital signal processor (DSP) 214, output devices 216, multimodal sensor array 218, one or more transcutaneous vagal nerve stimulation (tVNS) units 224A-N, and a computing device 230, which may act as a server, which may include a wireless communication adapter 232. Power supply 202 may include a battery and/or circuitry for providing power to system 200. Wireless communication unit 204 may include circuitry and software for providing wireless communications to and from system 200. For example, wireless communication unit 204 may perform functions such as the access protocol, security/firewall, connect to app, data transfer, receive control from app, connect to TENS units 205A-N, send stimuli to patches, receive data from patches, etc. TENS units 205A-N may provide electrical stimulation signals that may provide therapeutic benefit on pain. TENS units 205A-N may include a commercial unit, such as the iTENS, or may include a custom or customized TENS unit. In the exemplary embodiment shown in FIG. 2, TENS units 205A-N may communicate wirelessly via wireless communication unit 204. In embodiments, TENS units 205A-N may communicate via hardwired connections. In embodiments, each TENS unit 205A-N may include transcutaneous electrical nerve stimulation circuitry 219, which may include nerve stimulation signal generation circuitry 220, and each TENS unit 205A-N may include one or more electrodes or contacts 222, which may be made, for example, from carbon nanotubes (CNT) or graphene. In embodiments, each tVNS unit 224A-N may include transcutaneous vagal nerve stimulation circuitry 225, which may include vagal nerve stimulation signal generation circuitry 226, and each tVNS unit 224A-N may include one or more electrodes or contacts 228, which may be made, for example, from carbon nanotubes (CNT) or graphene.

Central control unit (processor) 206 may include a processor, such as a microprocessor, microcontroller, etc. to provide processing and control of the operation of system 200, such as to control signal generation and signal application by TENS units 205A-N and tVNS units 224A-N. Storage control unit and storage 208 may include storage circuitry and circuitry to control storage and retrieval of data from storage by central control unit (processor) 206. DAC 210 may include circuitry to accept digital signals and to output corresponding analog signals. ADC/amplifier 212 may include circuitry to accept analog signals and to output corresponding digital signals, and may include amplifier circuitry to amplify the accepted analog signals. DSP 214 may include circuitry to process digital signals corresponding to analog signals, in order to alter the ultimate characteristics of the analog signals. Output devices 216 may include devices to output sounds and other stimuli to a user of system 200. Output devices 216 may include one or more speakers to output sound, as well as other stimulus devices, as described below, to output other stimuli. Multimodal sensor array 218 may include a plurality of sensors to obtain information about the physical and physiological state of the user of system 200. Such sensors may include, but are not limited to, audio/voice recording sensors, such as microphones, etc., EEG sensors, ECG sensors, blood pressure sensors, body temperature sensors, gyroscopes, oxygenation sensors, accelerometers, magnetometers, nerve signal sensors, CNT, graphene elect./contact one or more electrodes or contacts, which may be made, for example, from carbon nanotubes (CNT) or graphene, etc.

The example shown in FIG. 2 illustrates the components of system 200 as separate blocks. However, one of ordinary skill in the art would recognize that these components may be combined with each other in physical devices in many different ways. It is well within the skill of one of ordinary skill in the art to arrange the various components based on engineering considerations. Embodiments of the present systems and methods may include any or all such arrangements.

Figure 13:
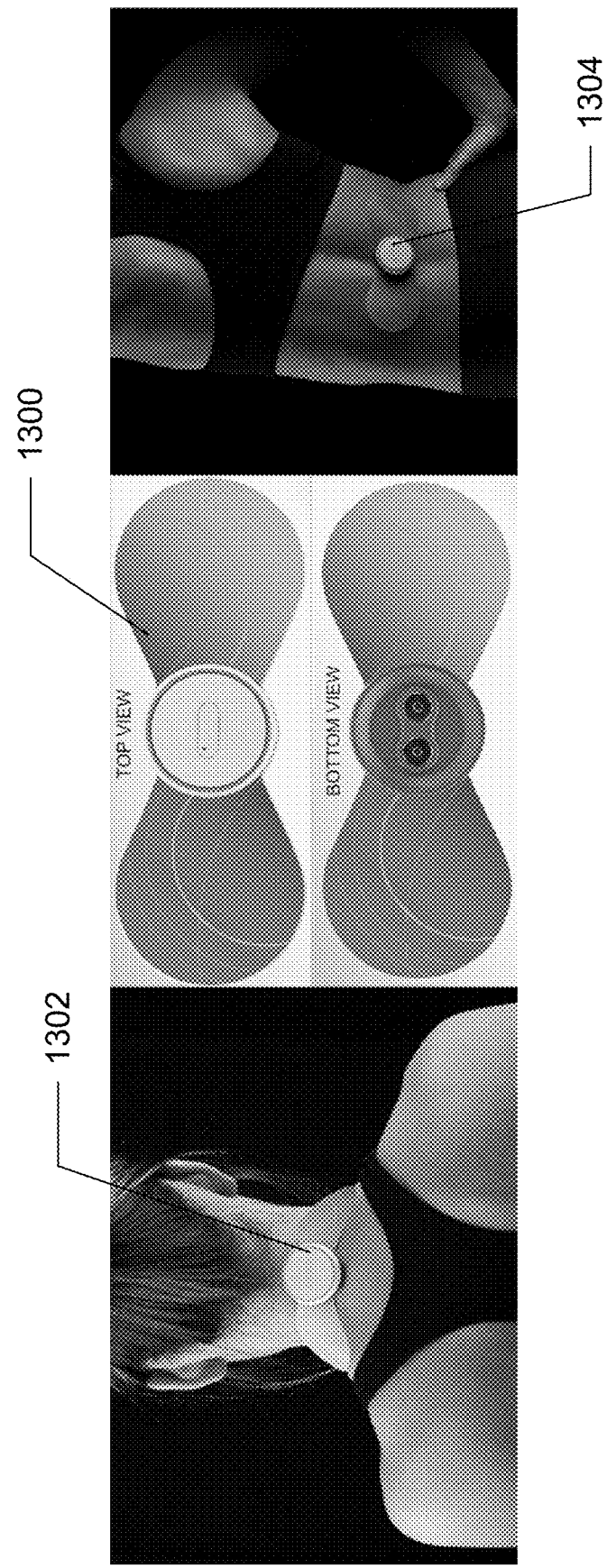
FIG. 13 is an exemplary illustration of a TENS unit according to embodiments of the present systems and methods.

Embodiments may include a TENS unit 1300, which may be commercially available, custom designed, proprietary, etc. An example of a commercially available TENS unit 1300, such as the iTENS, is shown in FIG. 13. TENS unit 1300 may be used to inhibit C fibers and stimulate proprioceptive signaling in A delta (Aδ) fibers to assist in the acquisition of novel tasks and motor skills. The iTENS device is the first FDA-cleared, wireless TENS therapy device controlled with an iOS or Android app. The app communicates with the iTENS devices over Bluetooth and sends these signals through gel pads and wings to the nerve. Using a secure, magnetic connection, the laser-printed silver conduction coming from the device is smooth, reliable, and powerful. The innovative wing structure is flexible and the water-based gel pads curve with movement, enabling iTENS to be worn without inhibiting activity. An energy efficient, lithium-ion battery provides 24 hours of use on a single charge, and the unique gel pad design is reusable and replaceable for multiple applications at a very low cost. In embodiments, the app that drives the earbuds may drive multiple iTENS devices in synchronous application. iTENS patches will not damage skin even under continuous use. An illustration of the devices and sample placements 1302, 1304 is shown in FIG. 13.

In embodiments, the sensors may be positioned for better stimuli and noise free multi-sensor data to test the plasticity. Embodiments may include variations in the size and weight of the earbuds and helmet, power consumption for multi-dimensional sensor array, charging the battery, for example, the helmet may be an intermediate source of power supply for the ear buds if they are equipped at the same time, bandwidth optimization for the data communication from and to the earbuds and helmet, and firmware design for both earbud and helmet for better interfacing with tablet/phone or any other compatible device.

In embodiments, software may be developed using available tools and libraries from vendors (such as iTENS, intent, Intel Corporation, etc.) and prior works (FCU, BC, etc.). Security requirements and protocols may also be defined, in advance of any development so as to ensure a consistent security design throughout. Server software may be written in, for example, Python using Django. Embodiments may include an API will be written to provide an interface for the website and mobile application. In embodiments, the mobile app may provide communication to the API, iTENS, and earbuds and may be provide control and reporting capabilities. Finally, custom software for the iTENS and intent earbud devices may be developed to drive and optimize these processes.

Embodiments may include 1) mobile software to communicate with iTENS patches and earbuds, providing both reporting and control capabilities; 2) server software to apply FCU and machine learning to deep analysis of data; 3) API and website to provide interface for reporting; 4) custom software in earbuds to provide FCU, high-level signal processing/filtering; 5) security protocol and end-to-end security for the system.

In embodiments, security features may include 1) a protocol of secure communication (iTENS patches, earbuds and Tablet App); 2) Authentication protocols for tablet software and cloud software; 3) Integrated security for data collection, application, wireless communication, analytics/storage and API layers; 4) Security controls and guidance for external interfaces to 3rd party systems, databases and services; and 5) Security controls including platform security consideration, user and application access security, data encryption and integrity, and attack/manipulation protection for the bi-directional data flows and user accesses.

Figure 3:
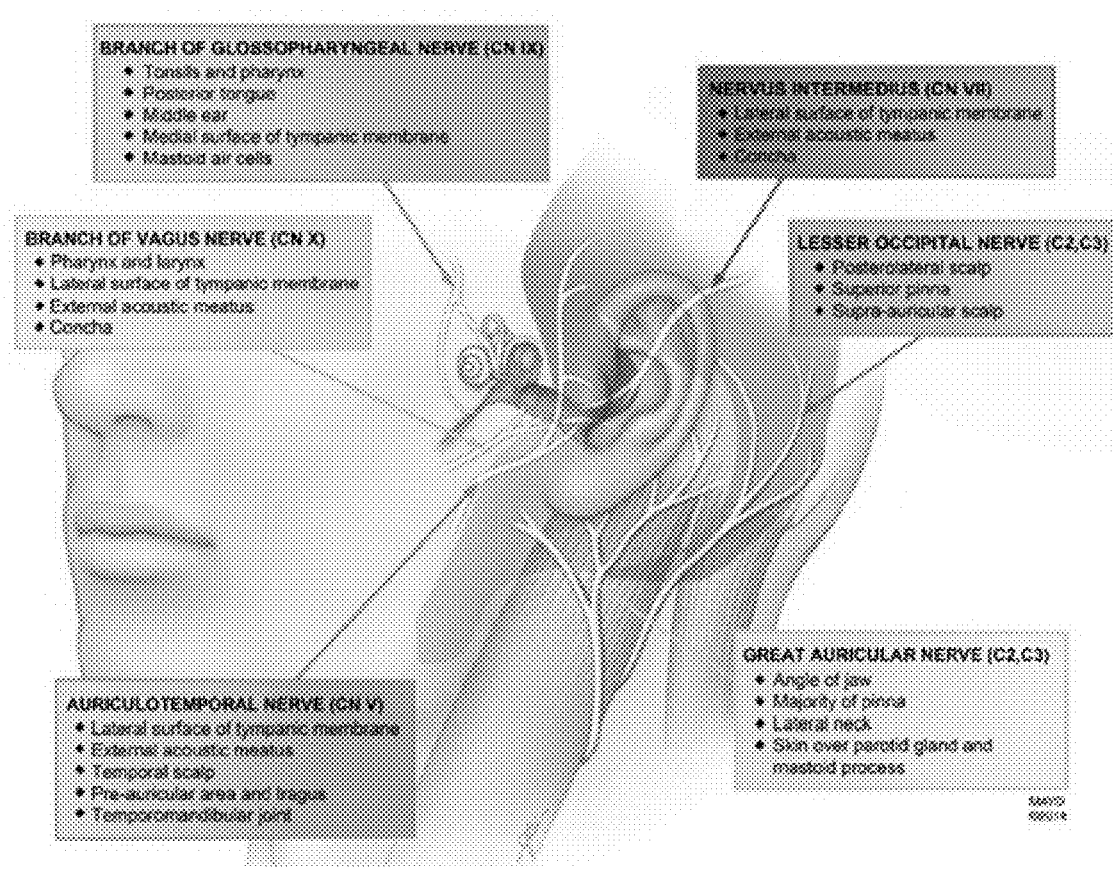
FIG. 3 is an exemplary illustration of anatomy of the Vagus nerve.
Figure 4:
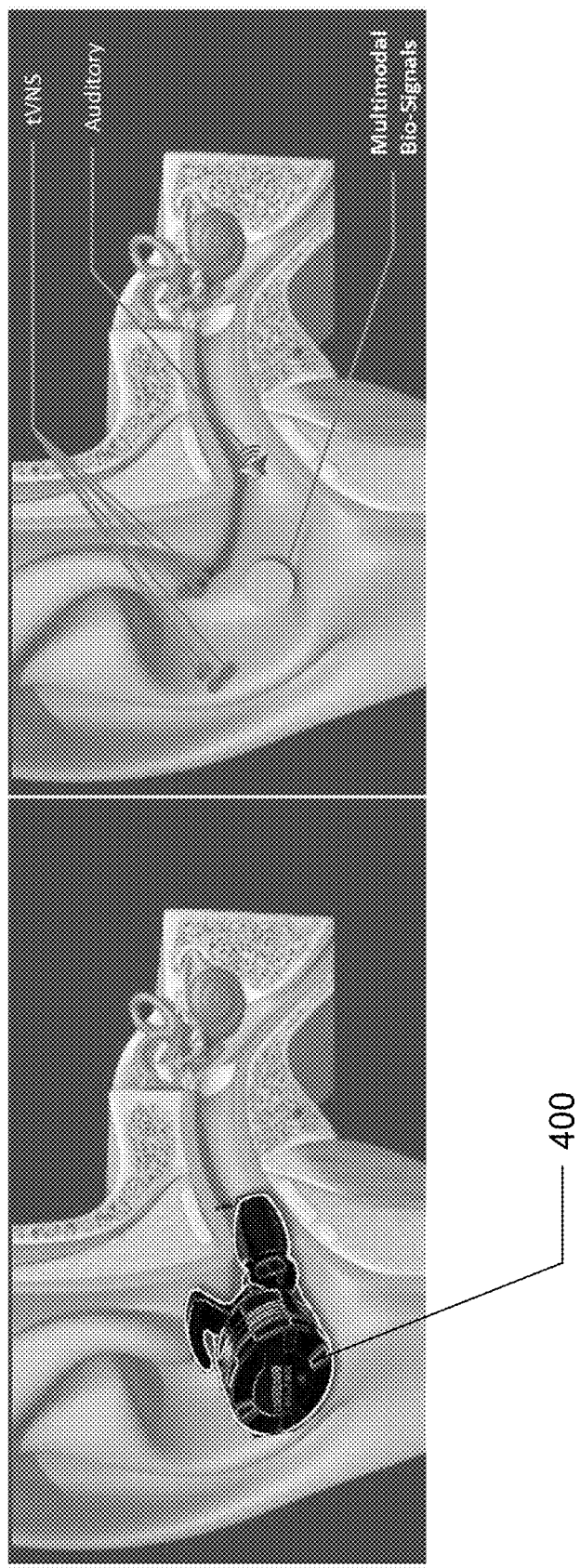
FIG. 4 is an exemplary illustration of contact points for the biosensors and tVNS stimulator within an earbud according to embodiments of the present systems and methods.
Figure 5:
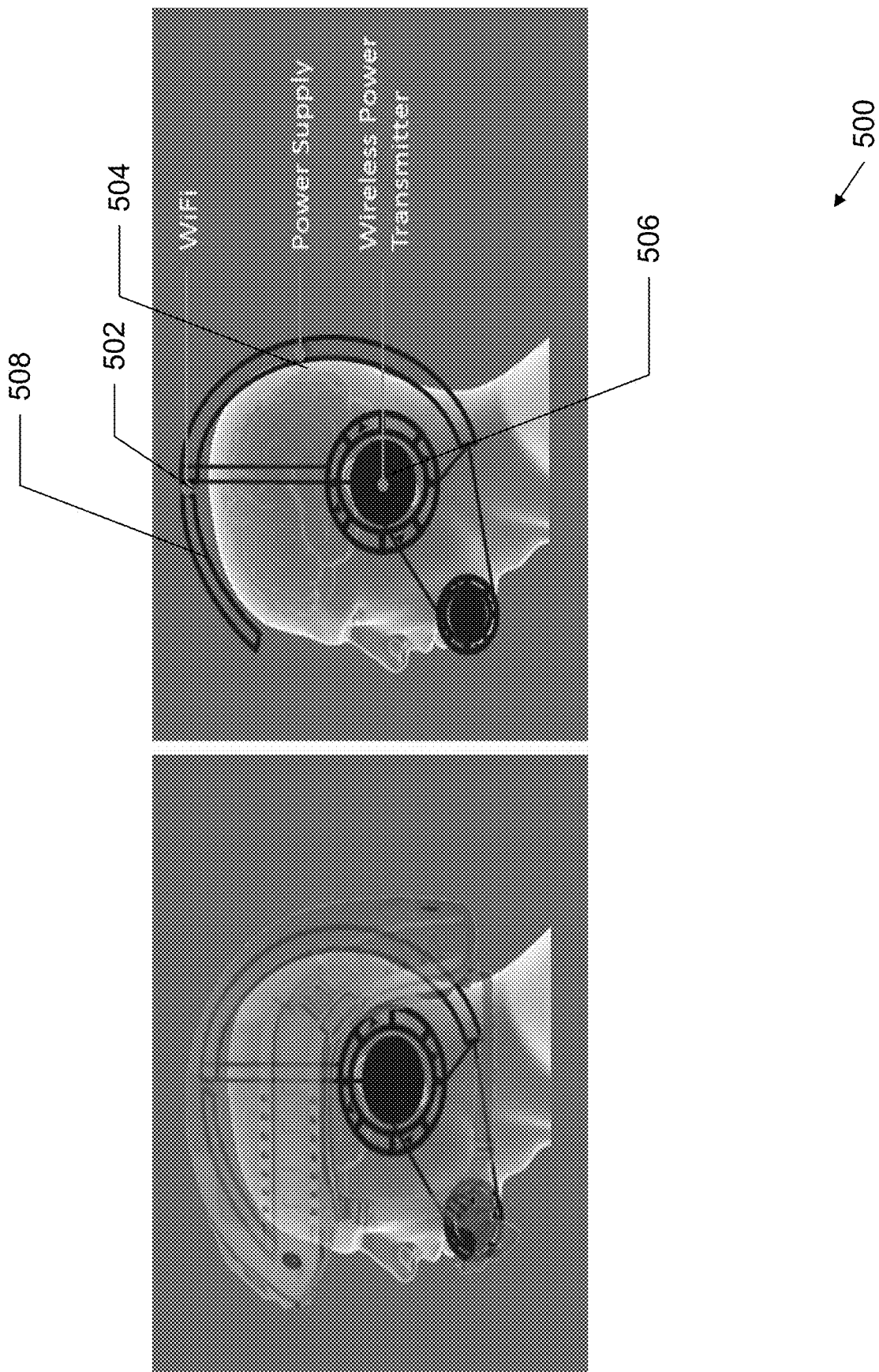
FIG. 5 is an exemplary illustration of a helmet according to embodiments of the present systems and methods.

The anatomy of the Vagus nerve is shown in FIG. 3. For cognitive skill training in humans, a transcutaneous vagal nerve stimulation (tVNS) unit, consisting of a stimulation unit and dedicated ear electrodes, may be built into a pair of customized earbuds 400, as shown in FIG. 4, for maximum mobility and comfort. FIG. 4 illustrates the contact points for the biosensors and tVNS stimulator within the earbud. The stimulation unit sends out electrical impulses, which are transferred via the ear electrode to skin afferents of the auricular branch of the vagus nerve in the left ear's cymba conchae. The earpiece may emit electrical, rectangular pulses (250 µs duration) with intensity above detection threshold and below pain threshold evoking a tingling sensation. FIG. 5 illustrates an embodiment 500 in which the various components, WiFi 502, backup power supply 504, inductive charging 506, etc., may be contained within a helmet 508.

Brain Plasticity. Neuroplasticity is the brain's ability to change itself, to form new connections, produce new cells, and sculpt existing connections to be more efficient. Brain plasticity allows the brain to adapt its structural and functional connectivity in response to an external condition by promoting a novel function, or a new way to perform an old function, or the suppression of a sensorimotor ability (Di Pino et al. 2014), therefore cerebral plasticity is a continuous process allowing short-term, middle-term and long-term remodeling of neurons-synaptic maps, to optimize the functioning of brain networks. Distinct from Plasticity, excitability is the immediate reaction of nerve cells to incoming change, whereas plasticity is the permanent transformation of a system of neurons (Gilbert et al. 2001).

Brain plasticity is an ambiguous term and refers to changes on myriad levels of the central nervous system. These changes need not be long-term, nor necessarily correspond to behavioral changes to be considered plasticity. Any experience will induce some degree of plasticity in the brain, but not every experience will do so to the same extent. What is more, changes on the molecular level do not necessarily translate to changes on the behavioral level, especially across subjects. The effect of molecular changes will depend on underlying genetics and neurochemical history. Importantly, not all plasticity in the brain is beneficial. Plasticity refers to any change in brain chemistry and behavior and therefore can be detrimental as well (Kolb et al. 2010). For example, cocaine could induce plasticity, but does not translate to enhanced cognitive function.

Mechanisms of Brain Plasticity. Brain plasticity is a multifaceted mechanism occurring in different contexts including development, diseases, and learning. Several hypotheses underlying plasticity have been suggested, from ultra-structural to synaptic map levels (Lomber & Payne 2001; Grafman 2000; Homer & Gage 2000; Chen et al. 2002). Plasticity is linked to several domains (a domain being a biological specificity or anatomical compartment) both having functional and time-space limited operational quality and tributary of inner or outer subject information. Plasticity may be viewed as changes of isolated neurons or a cluster of neuron activities, including synaptic efficacy, temporo-spatial relationship between ensembles of neurons in specific biological or anatomical domains. Cooperation of these mechanisms can lead to a variation of behavior through a restructuration of the eloquent networks, and through the elaboration of concrete 'neo-networks'.

At the neuronal level, dendritic spine and axonal sprouting or neo-synaptogenesis have been observed in vitro and in animals (Lamprecht & LeDoux 2004). Morphological synaptic plasticity may also be induced by brain damage, because rapid structural changes including number, size, and shape of dendritic spines have been observed rapidly after damage (Maletic-Savatic et al. 1999). Neurogenesis is another way the brain invokes plasticity and has been observed within the olfactory bulb, the dentate gyrus (Gould & Gross 2002) and the neocortex of adult primates (Gould et al. 1999). This phenomenon has also been observed in the adult human brain (Steindler & Pincus 2002; Sanai et al. 2004) and in vitro from multipotential progenitor cells isolated from the temporal neocortex (Pincus et al. 1997), hippocampus (Roy et al. 2000), and sub cortical white matter (Goldman & Roy 2014) of adults human brains. These new neurons may play a role in learning and memory, through the modulation of neuron-synaptic circuits, the elaboration of new connections between them, and the development of new networks (Gross 2000).

Executive Function. Executive function has become an umbrella term encompassing a myriad of cognitive processes, and although it has been extensively studied, we have yet to determine exactly what it entails and how it works. The term generally refers to the control and coordination of motor and cognitive functions to attain specific goals. To better understand the mechanisms behind executive function, models detailing the interaction between the Basal Ganglia (BG) and cortical areas by way of dopamine signaling have been developed (Stocco et al. 2009). These neural network models of cortico-BG circuitry include separate D1 and D2 striatal populations that differentially learn from positive and negative reward prediction errors (Hazy, Frank & O'Reilly 2006, Frank et al. 2006). Dopamine activity, tonic or phasic, acts on D1 and D2 striatal populations in opposite directions. Competing activity in these striatal populations regulates plasticity in the striatum thereby encompassing how BG uses dopamine signaling to direct behavior. Due to dopamine's role in reward representation and decision-making, these models have made for an excellent framework for cognitive processing as a whole (Beaudry et al. 2014; Hazy et al. 2007; Frank 2006; Collins & Frank 2013; Wiecki & Frank 2013).

More recently, the Adaptive Gain Modulation Locus Coeruleus (LC) Norepinephrine (NE) theory has been incorporated into computational models to further elucidate the mechanisms underlying executive functions (Aston-Jones & Cohen 2005). This theory provides some insight into how the brain regulates arousal/attention thereby mediating explorative and exploitative behaviors. Aston-Jones & Cohen (2005) describe an inverse U shape graph for tonic LC-NE activity and optimal attention performance. Whereas too little tonic LC-NE activity correlates with inattentiveness, too much LC-NE correlates with distractibility. More specifically, Aston-Jones & Cohen's (2005) theory for LC-NE Adaptive Gain Modulation argues that tonic LC-NE activity is inversely correlated with utility. In stable environments, the BG uses Reinforcement Learning (RL) to drive behavior without much interference so that consistently rewarded stimuli becomes proponent. Put simply, as reward contingencies are learnt, utility increases, LC-NE activity decreases, and exploitation is favored. On the other hand, in unstable environments, where utility is low, and no response is readily available, tonic LC-NE activity increases activating the anterior cingulate cortex (ACC) and orbitofrontal-cortex (OFC). ACC activation engages the hyperdirect pathway in the BG, which modulates the response threshold in the Subthalamic Nucleus (STN) and encourages explorative versus exploitative behaviors. There have been several studies, computational and not, that suggest the validity of this mechanism as a way to explain how the brain deals with uncertainty (Huang & Rao 2013; Aston-Jones & Cohen 2005; Huettel et al. 2005; Ide et al. 2013; Wiecki & Frank 2013; Collins & Frank 2013; Frank 2006; Hazy et al. 2007; Cavanagh et al. 2011; Alnæs et al. 2014).

Cerebellum. The cerebellum contains half of the brain's neurons. It plays a vital role in coordinating movement, as evidenced by lesion studies in animal models (Ito 1976; Ekerot & Jörntell 2003; Vercher & Gauthier 1988; Amrani et al. 1996; Baizer et al. 1999). Other findings have suggested that the cerebellum is also involved in cognition (Lalonde 1994; D'Angelo & Casali 2012; Noroozian 2014; Koziol et al. 2014; Schmahmann 1991). Although exact mechanisms are not well known, some suggest that the cerebellum provides a more Increased cerebellar plasticity has been associated with faster transfer to automaticity in learning (Ekerot & Jörntell 2003). The cerebellum influences early learning (coordinating sequence), but its involvement tapers off as learning is automated and carried out by the BG. It has also been found that activity in the cerebellum increases during high uncertainty decision making, this may be because of its involvement in attention. The cerebellum is involved in regulating attention by means of error-signal detection, irregularity detection, stimulus salience etc. For example, there is more involvement of the cerebellum in attention switching tasks (such as the Wisconsin Card Switching Task) than in simple tasks (McClure et al. 2006; Balsters et al. 2013; Koziol et al. 2014). The cerebellum is also involved in autonomic visual attention (Porrill & Dean 2007; Coffin et al. 2005; Raberger & Wimmer 2003) and therefore may play an important role in LC-NE attention/arousal modulation (Alnæs et al. 2014).

It is also known that long-term depression (LTD), a form of neuroplasticity, is the mechanism by which activity is regulated in the cerebellum, specifically at the level of Purkinje cell-Parallel fiber synapses (Uemura et al. 2007; Chen & Thompson 1995; Kano et al. 1985). In fact, when a motor performance ends in failure, climbing fibers send a signal to depress the synaptic transmission from parallel fibers projecting onto Purkinje cells, which weakens the connections that might have contributed to the failed action, resulting in a decreased excitatory post-synaptic potential (EPSP) at the level of Purkinje cells (Ito 1976). This mechanism, called LTD, acts like a filter that reduces the effect of unnecessary connections in the process of learning motor tasks. Thus, LTD, in the cerebellum, is crucial for motor learning (Schonewille et al. 2011). This suggests that the cerebellum is a region of interest to our project if we want to study the effect of peripheral nerve stimulation on motor learning.

State of The Art in Plasticity Enhancement. Humans have long used cognitive enhancement methods to expand the proficiency and range of the various cognitive activities that they engage in. With the development of neuroscience-based techniques, a variety of neuroenhancement methods has been developed to increase cognition in human. This includes transcranial electromagnetic stimulation methods, such as transcranial direct current stimulation (tDCS) and transcranial magnetic stimulation (TMS), along with deep brain stimulation (DBS), behavioral training techniques, and other techniques in conjunction with neuroimaging. These methods have been reported to improve attention, perception, memory, and other forms of cognition in healthy individuals, leading to better performance in many aspects of everyday life (Clark & Parasuraman 2014).

Transcranial direct current stimulation (tDCS) is a non-invasive brain stimulation technique that has shown modulatory effect on cognitive functions and motor behavior in healthy subjects and patients with neuropsychiatric diseases. tDCS effects have been reported on three fundamental cognitive processes: attention, learning, and memory, which can mediate higher-order cognitive processes such as decision-making and problem solving. For example, enhanced executive attention control (or reduced distractibility and/or inattentiveness) leads to more accurate and less biased decision making (De Martino et al. 2006; Parasuraman & Manzey 2010). The use of tDCS in healthy adults is also of relevance to efforts to accelerate learning and enhance performance in such domains as education (Wlodkowski 2003), the military (Clark et al. 2012; Falcone et al. 2012; Nelson et al. 2014), and other work and everyday settings (Parasuraman 2011; Parasuraman & Jiang 2012).

TMS has been used to modulate neuroplasticity by enhancing or decreasing cortical excitability to potentiate or reduce neuroplasticity processes (Cohen et al. 1993; Hallett et al. 1993; Pascual-Leone et al. 1997; Pascual-Leone & Wassermann 1996; Pascual-Leone et al. 1994; Pascual-Leone et al. 1998; Pascual-Leone et al. 1999; Pascual-Leone et al. 2011). TMS has been used to demonstrate reorganization of cortical motor outputs after acquisition of new motor skills, transient immobilization, amputation, and recovery from CNS injury (Liepert et al. 1995; Pascual-Leone et al. 1995; Pascual-Leone et al. 1996). It has also been used for recovery in stroke patients, and aphasia (Coffman et al. 2014; Fritsch et al. 2010).

Vagus Nerve Stimulation. First developed in the 1980s, VNS is an invasive, yet effective means of neuromodulation. VNS has been used as treatment for epilepsy (Hays et al. 2013) and has more recently been considered as treatment for a series of psychiatric conditions including migraines (Hays et al. 2013) and treatment-resistant depression (Fang et al. 2016; Fanselow 2013; Nemeroff et al. 2006) among others (Schachter 2004; Van Leusden et al. 2015; Hays et al. 2013).

Ventureyra developed tVNS as a non-invasive method of stimulating the vagus nerve. tVNS utilizes the topographic anatomy of the auricular branch of the vagus nerve located in the concha of the human ear in order to gain non-invasive access to the vagal system (Ellrich 2011). Several studies have demonstrated success using a tVNS protocol of stimulating the external ear to modulate the Vagus Nerve (Van Leusden et al. 2015; Frangos et al. 2015; Fang et al. 2016). Furthermore, Frangos et al. (2015) used fMRI to validate that tVNS is as effective as invasive VNS to stimulate the brain stem.

Many therapeutic and nontherapeutic applications have been developed using tVNS to treat a myriad of conditions including epilepsy (Ben-Menachem et al. 2015; Stefan et al. 2012; Anon n.d.) depression (Fang et al. 2016), headaches (Magis et al. 2013; Hays et al. 2013; Goadsby et al. 2013; Nesbitt et al. 2013), pain (Busch et al. 2013) and memory (Boon et al. 2006; Jacobs et al. 2015; Liu et al. 2016). Since tVNS is non-invasive and inexpensive, the technique has also been gaining attention as an experimental tool for conducting fundamental research (Steenbergen et al. 2015; Kraus et al. 2013; Argyropoulos 2016). This research has produced a growing body of literature suggesting the feasibility of using tVNS to enhance and direct cognitive control (Van Leusden et al. 2015; Jacobs et al. 2015). For instance, tVNS targeting hippocampal hyperactivity improved cognition in schizophrenic patients (Smucny et al. 2015).

In embodiments, the effect of VNS and TENS on neuroplasticity using established animal models in vitro and in vivo may be determined. All procedures should be carried out in accordance with the NIH Guide for the Care and Use of Laboratory Animals, and require approval by the Institutional Animal Care and Use Committee of Georgetown University.

Surgically implanted VNS electrodes may be used to stimulate mice during cognitive task training. The effect of VNS and TENS on neural plasticity may be measured in two different rodent behavioral tasks combined with in vivo multiphoton imaging. The first cognitive training paradigm, the Intra/ExtraDimensional Set Shift task, may target cognitive flexibility. The second and third cognitive training paradigm may use the Erasmus Ladder task and Rotarod task.

The Intra/extraDimensional Set Shift Task measures alterations in executive control and cognitive flexibility in an adapted version of the Wisconsin Card Sorting Test and the CANTAB task, which are both widely used measures of attentional control in humans and animal models (Scheggia & Papaleo 2016). To evaluate motor function training, the Erasmus Ladder Task and Rotarod Task will be used to measure the acquisition and adaptability of an unfamiliar motor skill (Schonewille et al. 2011; Shiotsuki et al. 2010; Bruinsma et al. 2015).

We may use Calcium imaging to measure changes in neural activity and demonstrate that VNS promotes synaptic plasticity. Our approach may consist of injecting an adeno-associated virus (AAV) to express GCaMP6f, a fast genetically encoded calcium indicator (GECI) in the cells of interest (e.g. Purkinje cells of cerebellum). These indicators respond to the binding of Calcium ions by changing their fluorescence properties. It may then be possible to record neural activity by optical imaging of fluorescence intensity changes in cells expressing those calcium indicator (Russell 2011). The idea is to compare the activity in these cells, before, during, and after VNS. For instance, calcium imaging constitutes a very appropriate choice to study plasticity in the cerebellum. It may permit us to probe the functional changes in Purkinje cells by measuring the spiking activity in correlation with VNS and behavior. On the other hand, calcium imaging may provide insightful data from an anatomical point of view, by monitoring cell growth and measuring changes in dendritic spine density in target neurons, all linked to neuroplasticity.

Additionally, dendritic spines in the hippocampus may be quantified, before and after training, using in vivo multiphoton imaging of rodents implanted with a chronic hippocampal window (Gu et al. 2014; Engert & Bonhoeffer 1999). A similar procedure may be used to quantify cerebellar plasticity (Dunaevsky 2012; Wilms & Hausser 2015). Novel fluorescent calcium sensors have been used in rodents to detect single action potentials and calcium transients in individual dendritic spines, for functional analysis of neuronal circuitry before, during, and after VNS/TENS assisted and placebo learning (Chen et al. 2013). We may use 2 photon imaging combined with patch clamping in brain slices to analyze both dendritic spine density changes as well as the effects on synaptic amplitude during stimulation of the vagus nerve (Roy et al. 2016).

Figure 6:
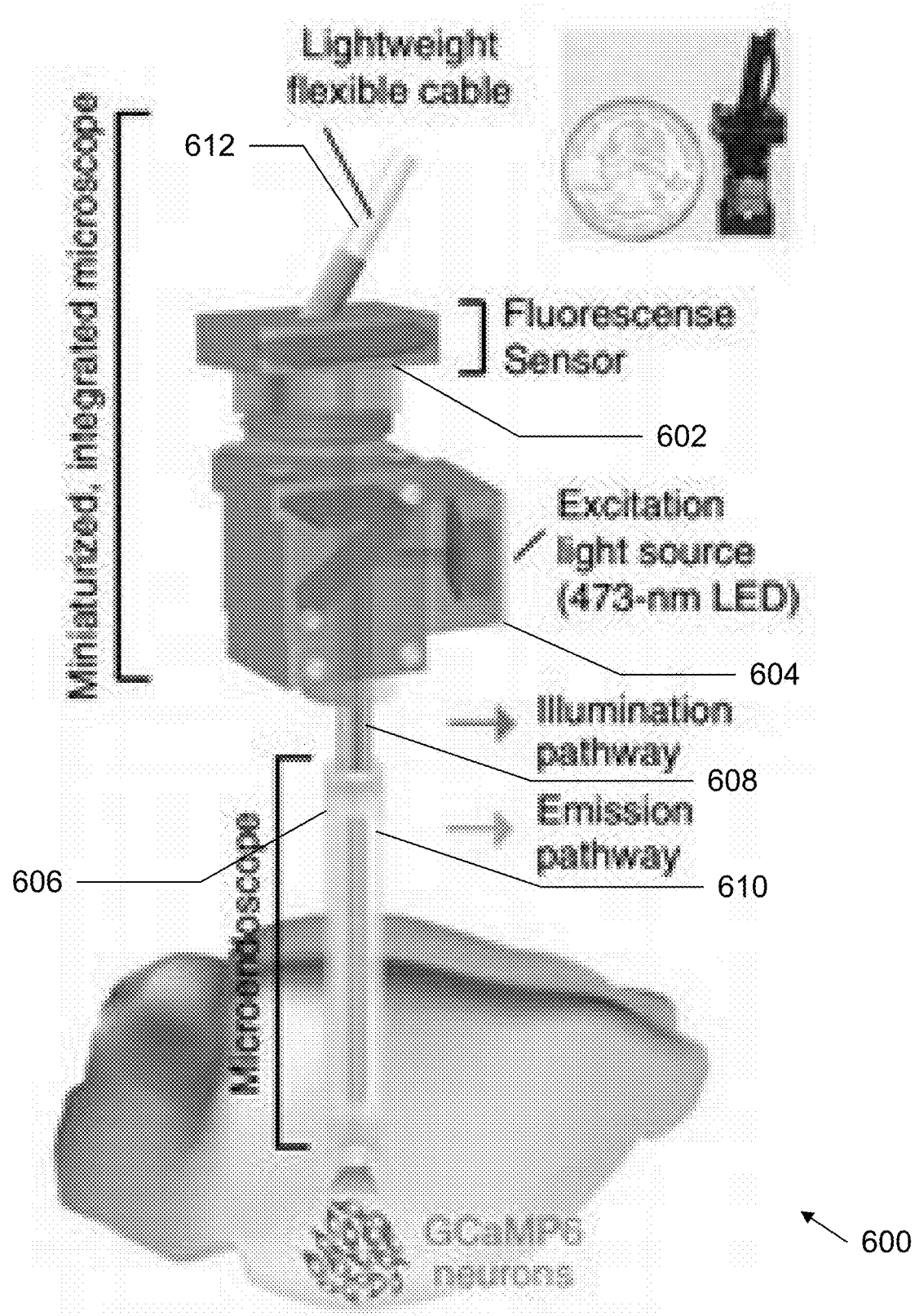
FIG. 6 is an exemplary diagram of a microscope according to embodiments of the present systems and methods.

For in vivo experiments we may use 2-photon imaging during stimulation to record changes in neural activity linked to long-term depression (LTD) and long-term potentiation (LTP). 2 photon microscopy allows us to perform high resolution imaging of brain regions of interest and identify the smallest changes in spiking activity and dendritic spine density. However, this technique cannot be used to track brain activity in the behaving mice unless they are head restrained. Which limits our possibilities of assessing the effect of VNS in the context of complex learning tasks where the animal needs to move freely (e.g. in a maze). To address this issue, we propose to use implantable miniaturized microscopes for further analysis during the learning task. In order to perform calcium imaging, we may implant miniaturized fluorescence microscopes on rodents' heads to record from cerebellum, hippocampus, and motor cortex. For example, such a scope may include a chassis, electrical and optical components, and printed circuitry connected to a coaxial cable. An example of such a microscope 600 is shown in FIG. 6. As shown in FIG. 6, a fluorescence microscope 600 may include a fluorescence sensor 602, an excitation light source 604, such as a 473 nm LED, a microendoscope 606, including an illumination pathway 608 and an emission pathway 610, and a signal and power cable 612. These microscopes may weigh less than 3 grams and embodiments may be built from off the shelf components. Embodiments may be based on the work of Ghosh et al. (Ghosh et al. 2011) from the Schnitzer lab at Stanford University. The miniaturized microscope works exactly as a regular fluorescence microscope however, this technique takes advantage of the widespread availability of microfabricated components.

The microscope works as follows: the illumination pathway starts with an excitation light source (473-nm (blue) LED on a printed circuit board (PCB)) emits light that is collected by a drum lens. The light then passes through an excitation filter to remove unwanted wavelengths. A dichroic mirror deflects off the light into a gradient refractive index (GRIN) objective lens which focuses illumination on the imaged sample. Emitted fluorescence from the sample marks the beginning of the emission pathway. Fluorescence returns through the objective and passes through the dichroic mirror (without reflection), then through an emission filter and an achromatic lens which focuses the image on a CMOS sensor mounted on a PCB and connected to a data acquisition (DAQ) board for live video processing, via a lightweight tether. The DAQ is then connected to a computer for live display, data analysis, and storage. The body of the microscope will be 3d-printed. The miniaturized microscope will provide a resolution of, for example, 752px×480px and a full-field frame rate of up to 60 Hz.

This technique may provide progress in the study of neural dynamics. In fact, with an implanted miniaturized microscope it may be possible to analyze neural activity from hundreds of neurons (substantially higher capability compared to electrode recordings) while the animal is doing a behavioral task. Doing optical imaging in freely moving rodents will allow us to correlate neural activity not only with VNS but also with behavior.

We may also use a batch of mood/anxiety tasks to monitor cognitive side effects. For rodents we will use established task paradigms such as Open-field, Elevated Plus Maze, Tail Suspension, Grip Strength, Hot Plate, and Marble Burying. We will also conduct a few context control experiments and a few motor control experiments to try and distinguish between bottom-up and top-down influences on increased behavioral flexibility, consistent with our predictions.

Data analysis and Mapping. Recordable neurophysiological signals as well as neuroimaging are available from multiple levels of the brain, including a single neuron, multiple individual neurons, a localized population of neurons, or a large-scale population of neurons. With VNS and TENS neuromodulation, synapses are either strengthened or pruned, dendrites branch out to make new connections, and blood vessels and support cells grow to support the change. With multimodal, multiscale data and corresponding analysis methods, it is possible to build the structural and functional mapping from peripheral stimulation, to brain activity, and to behavioral output.

In embodiments, data from in vitro and in vivo may be analyzed using intracellular and extracellular recordings to measure plasticity on a cellular/neuronal level and develop anatomical and functional mapping by using cellular imaging data as well as electrode electrophysiological data. Here neural plasticity refers to changes in spiking activity or dendritic spine density.

In vitro, we may measure cellular plasticity using slices of living mouse brain tissue. Sections of brain tissue can be analyzed for presence of proteins that indicate more connectivity between neurons. It is thought that special proteins in the supporting cells around the neuron are responsible for promoting growth of synapses and dendrites. These proteins can be considered markers of plasticity. We may perform intracellular recording as well as the extracellular recording. Intracellular recording involves measuring voltage and/or current across the membrane of a cell. The voltage clamp technique allows us to "clamp" the cell potential at a chosen value, which makes it possible to measure how much ionic current crosses a cell's membrane at any given voltage. The clamp technique records the membrane potential by injecting current into a cell through the recording electrode. The extracellular recording includes single-unit recording, multiunit recording, as well as local field potentials.

In vivo, we may examine the neural activity of the mouse brain using high resolution miniature microscopes.

We may image changes in spiking activity, dendritic spine density, as well as synaptic efficacy in different brain regions. These regions may include: the cerebellum, the hippocampus, and the motor cortex. For each region we may have a set number of implanted animals that may be trained on specific tasks in order to assess brain activity and map the effect of VNS on those regions.

We may test the effectiveness of noninvasive tVNS and TENS on human neuroplasticity with 3 series of cognitive skill training. Using wireless earbuds in combination with a smartphone/table or helmet (Matthews et al. 2008) and reusable self-adhesive iTENS patches, tVNS and TENS stimulation may be noninvasive, portable and comfortable for optimum cognitive training. The Earbuds also house a suite of biosensors, including electroencephalogram (EEG), electrocardiogram (ECG), oxygen saturation of skin (PulseOx), heart's electrical cycle (QT intervals), blood pressure (BP), heart rate (HR), respiratory rate (RR), true body temperature the (IR Thermal Sensor), motion (Accelerometer), rotation (Gyroscope) and audio capture (Mic). These multimodal data streams may be collected during stimulation to monitor physiological side effects and to enrich our analysis of underlying mechanisms involved in plasticity.

To assess motor acquisition, we may use a modified Visio Motor Skill Task paradigm. To assess cognitive flexibility we may use a Wisconsin Card Sort Task paradigm (Heaton et al. 1993) and to assess verbal skill, we may use a modified and extended Predictive World Task paradigm.

We may also use a batch of mood/anxiety evaluations to monitor cognitive side effects and changes in behavior. More specifically all subjects may be asked to complete a Positive and Negative Affect scale (PANAS), a 20-item self-report measure before and after the training period to screen for both potential short-term (within session) and/or long-term (across sessions) effects of tVNS on mood (regardless of direction) (Reis et al. 2009).

Data Analysis and Algorithm Design. We may use algorithms and software for the analysis and visualization of data on animals as well as humans. And then we may develop ways to "close the loop": to analyze neural data online during experiments, and use the results to optimize experiment protocols, or perform targeted manipulations of neural activity by peripheral stimulation. This brings together several exciting challenges—data stream processing, online machine learning, real-time visualization, and closed-loop experimental design.

Brain mapping is the visualization of "brain areas and their interconnection engaged in a certain function" (Shibasaki 2008). Non-invasive techniques currently available for brain mapping and analysis are largely divided into two groups based on electrophysiological or hemodynamic principles. The former group includes EEG, MEG, and transcranial magnetic stimulation (TMS); the latter group includes positron emission tomography (PET), single-photon emission computed tomography (SPECT), fMRI, and near-infrared spectroscopy (NIRS). We may record EEG during cognitive skill training and stimulation. We may use sophisticated mathematical signal analysis techniques such as correlation dimension (CD) a nonlinear time series analysis technique, signal coherence, fractal dimension, small world, and entropy, for dimensional analysis of EEG recordings.

A number of analysis approaches have been applied to identify plasticity changes in recording data. An analysis approach that is becoming standard in the functional imaging community uses the general linear model (GLM) to estimate the effects of a set of variables. Analyses may also be conducted to examine differences over a time series (i.e. correlations between a task variable and brain activity in a certain area) using linear convolution models of how the measured signal is caused by underlying changes in neural activity and examine effects of interest while removing the effects of other possibly confounding variables. In some cases, simpler subtraction analyses have been used to analyze learning data.

Network analyses or connectivity analyses, have been used to identify networks of brain regions and their interactions. Functional connectivity analyses the correlation between activity in particular brain regions in a model-free manner. Effective connectivity analyses, on the other hand, are used to determine the causal structure of influences on different brain regions. They together to provide a promising method to understand how the localized regions work together as large-scale neural networks (Poldrack 2000).

Using data from human trials, we may develop a closed-loop neurostimulation optimization feature to auto-sense physiological and behavioral feedback to modify stimulation and/or training protocols to achieve optimal performance. In closed-loop neurostimulation application, an understanding of the relationship between human behavioral performance and physiological signals under the influence of external peripheral neurostimulation is fundamental to any utilization of the signal as a surrogate marker for cognitive enhancement. Closed-loop neurostimulation based on available neuronal recording and meaningful behavioral performance can use measurements to automatically adjust the peripheral neurostimulation as the device is operating. In this way, the closed-loop control could guide perturbations of neural systems (neurons and circuits) to achieve sophisticated, near real-time control over neurostimulation/neuromodulation and cognitive skill training.

TABLE 1

Overview of Proposed Approach

| Targeted Cognitive Skill | | Task/Training Paradigm | Mechanism |
|---|---|---|---|
| Phase I Mice | Cognitive Flexibility | Intra/Extra Dimensional Shift Set Task | Global monoamine increase following VNS stimulation |
| | Motor Function | Rotarod Task | Motor performance and learning over time, dealing with an obstacle paired with a conditioned stimulus. Cerebellar excitation following VNS |
| | Motor Function | Erasmus Ladder Task | Motor performance and learning over time, dealing with an obstacle paired with a conditioned stimulus. Cerebellar excitation following VNS |
| Phase II Humans | Motor Function | Visio motor skill Task | Motor acquisition and adaptation skills over range of task difficulty/uncertainty Cerebellar excitation following tVNS and/or increased tonic LC-NE activity as possible mechanisms. |
| | Cognitive Flexibility | Wisconsin Card Task | Cognitive flexibility and generalization abilities (rule learning, switch/stay executive function). Cerebellar excitation following tVNS and/or increased tonic LC-NE activity as possible mechanisms. |
| | Verbal Skills | Predictive world task | Predictive inference abilities in language possibly facilitating language error-processing and more effective language learning skills. Cerebellar excitation following tVNS and/or increased tonic LC-NE activity as possible mechanisms. |

Understanding the cerebellum as an error-processing engine within the BG-dopamine-LC-NE framework may help further elucidate how the human brain learns and makes decisions in high-uncertainty situations. This is particularly relevant to better understanding human behavior and executive function, especially in terms of real world applications where utility is not as palpable. Therefore, this proposal aims to probe at the cerebellum's involvement in executive function, particularly as a necessary error-processor. With a better understanding of this, it may be possible to explain/induce enhanced learning and decision-making in real-world scenarios following tVNS and other types of stimulation.

Exciting the cerebellum via stimulation of the Vagus Nerve may improve predictive-inference capabilities and enhance learning by improving executive control of attention due to enhanced LC-NE activity. To test this hypothesis we will use a combination of VNS and TENS stimulation to excite the cerebellum (invasively in rodents and transcutaneously in humans). tVNS reliably stimulates the cerebellum but its effect on the brain in not constrained to the cerebellum. Therefore it cannot reliably be inferred that enhanced performance is alone associated with increased cerebellar activity correlated with tVNS stimulation rather than alternative explanations such as hippocampal inhibition or global increase in monoamine activity in the brainstem. We predict that enhanced performance likely correlates to a combination of all these factors and even others. The selected methodology, simulation and training protocols here developed asses performance across the motor, linguistic, and cognitive flexibility functions and look into the possible neural mechanisms involved.

Implantable Vagus nerve stimulators may be acquired from, for example, Harald Stauss Scientific, and example of which is shown in Fig. The implantable nerve stimulators are for chronic nerve stimulation in conscious unrestrained mice. The bodies of the modules are designed to be implanted subcutaneously. Besides the battery, the modules contain a microprocessor that will be programmed individually. Continuous and scheduled stimulation protocols will be programmed.

Figure 8:
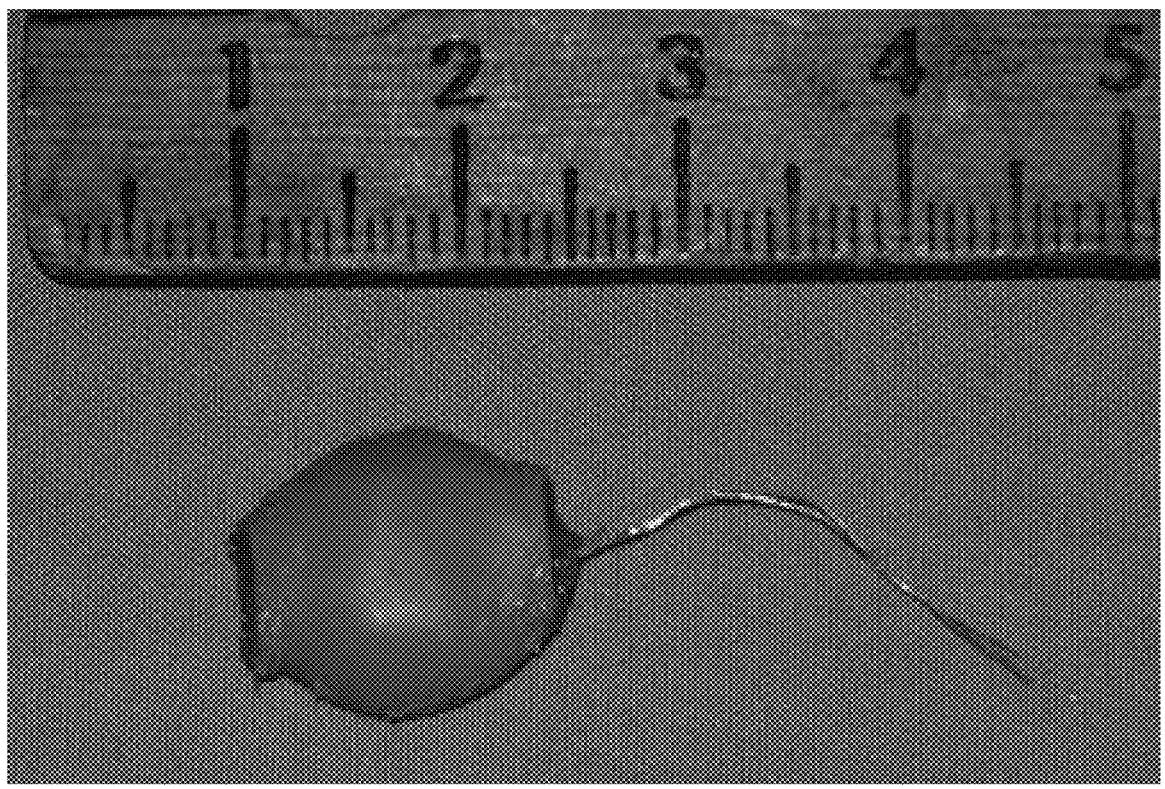
FIG. 8 is an exemplary illustration of an implantable vagus nerve stimulator according to embodiments of the present systems and methods.

Specifications for, for example, the implantable vagus nerve stimulator for mice from Harald Stauss Scientific shown in FIG. 8 may include Stimulation voltage: 3.0 V, Stimulation frequency: customized (e.g., 5 Hz). Multiple stimulation frequencies can be programmed into the module. Switching between stimulation frequencies is possible with an external magnet. A radio frequency transmitter sends a signal that indicates the setting of the stimulator (stimulation frequency) every 75 seconds and on change of the setting. The radio frequency signal can be received with a standard AM radio. Pulse Width: customized, for example, 1 ms. Can be turned on and off with an external magnet. Electrode wire: silver wire for Rat Neural Stimulation (RNS), platinum wire for Mouse Neural Stimulation (MNS). Battery life: about 6 months for RNS, about 1 month for MNS. Weight: about 4.6 g for RNS, about 1.2 g for MNS.

Rodent VNS stimulators are available as off the shelf products, but TENS stimulators used for rodent experiments are typically commercial TENS devices for use on humans (such as http://www.lgmedsupply.com/tecodiparesy.html) modified for rodents (Vera-Portocarrero et al. 2013). Work required to modify commercially available TENS stimulators for rodent use is expected to be minor.

An Operon chamber may be used for the Intra/Extra Dimensional Set Shift Task and may be assembled from standard, modular chambers and accessories (poke holes, olfactometers, LED lights, etc.) available from commercial retailers.

Figure 9:
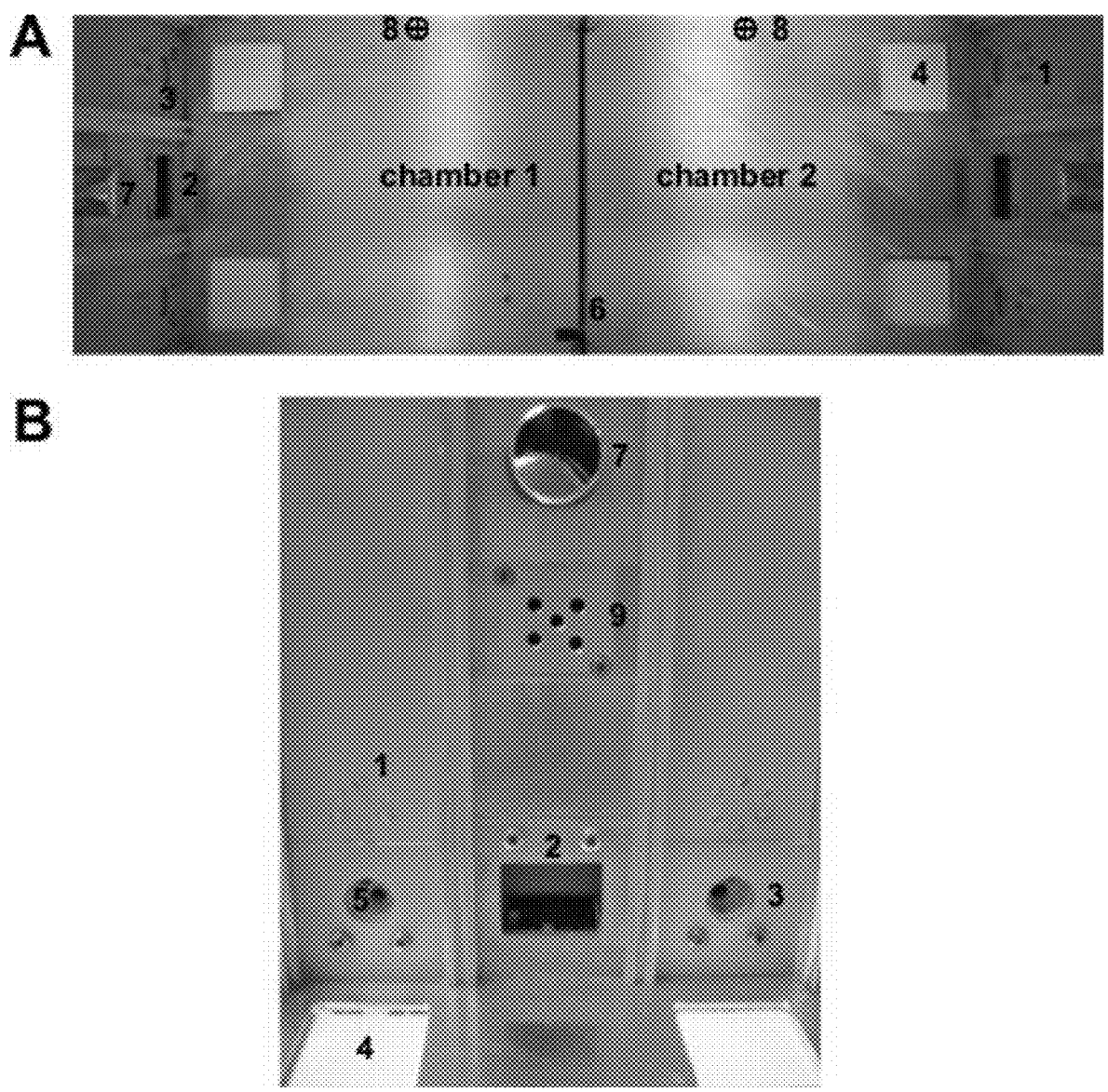
FIG. 9 is an exemplary diagram of illustration of an Operon apparatus.

The Operon apparatus, an example of which is shown in FIG. 9, includes two identical chambers with Plexiglas walls and an aluminum floor (16×16×16 cm3 for each chamber). Chambers are separated by a transparent Plexiglas dividing door that can be automatically controlled to allow the mouse to access either chamber. Each chamber has two nose-poke holes with infrared photobeams, and, between them, a food magazine with photobeams where a pellet dispenser delivered the food reinforcement. A fan and a house-light are located above each of the two food magazines.

FIG. 9 shows the two-chamber "Operon" apparatus. (A) View from the top of the entire apparatus and (B) view from the front of a single chamber mimicking the mouse point-of-view during the test. 1: visual stimuli (LEDs); 2: food magazine; 3: nose-poke hole; 4: tactile stimulus (texture); 5: olfactory stimulus; 6: automatic sliding door; 7: house-light;

8: infrared photobeam for door control. Chambers (16×16×16 cm3) are separated by a transparent plastic door (6). Infrared photobeams (8) track the animal movements and controlled the opening/closing of the automatic door to allow the mouse to change chambers. Each chamber presents two nose-poke holes (3) with infrared photobeams, and, between them, a food magazine (2) with photobeams where a pellet dispenser delivered the food reinforcement. A houselight (7) is located above each of the two food magazines. Each nose-poke hole is equipped with a series of changeable stimuli that could vary in three different perceptual dimensions (odor, view, tact). Originally published in (Scheggia et al. 2014) and (Scheggia & Papaleo 2016).

Figure 10:
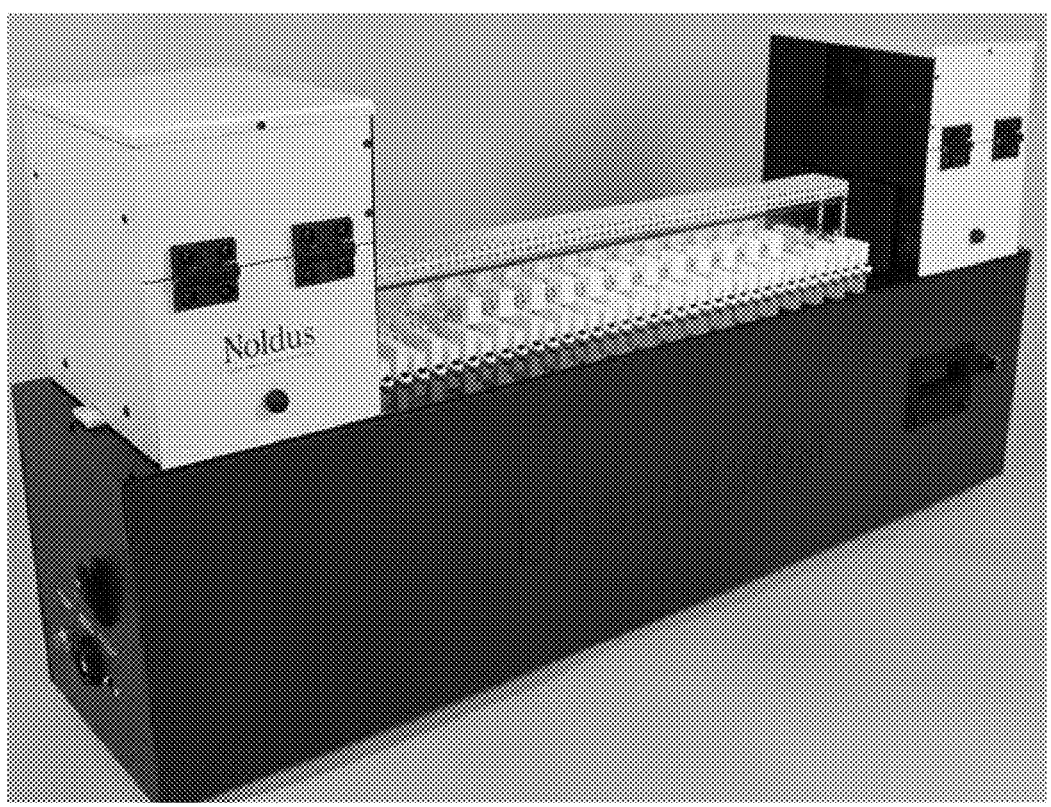
FIG. 10 is an exemplary diagram of a Noldus Erasmus Ladder.

The Noldus Erasmus Ladder, and example of which is shown in FIG. 10, (http://www.noldus.com/animal-behavior-research/products/erasmusladder) is a high throughput, fully automated system for assessment of motor performance and motor learning in mice. The system comes complete with all the required components and operating software. FIG. 10 shows a fully assembled Noldus Erasmus Ladder.

Figure 11:
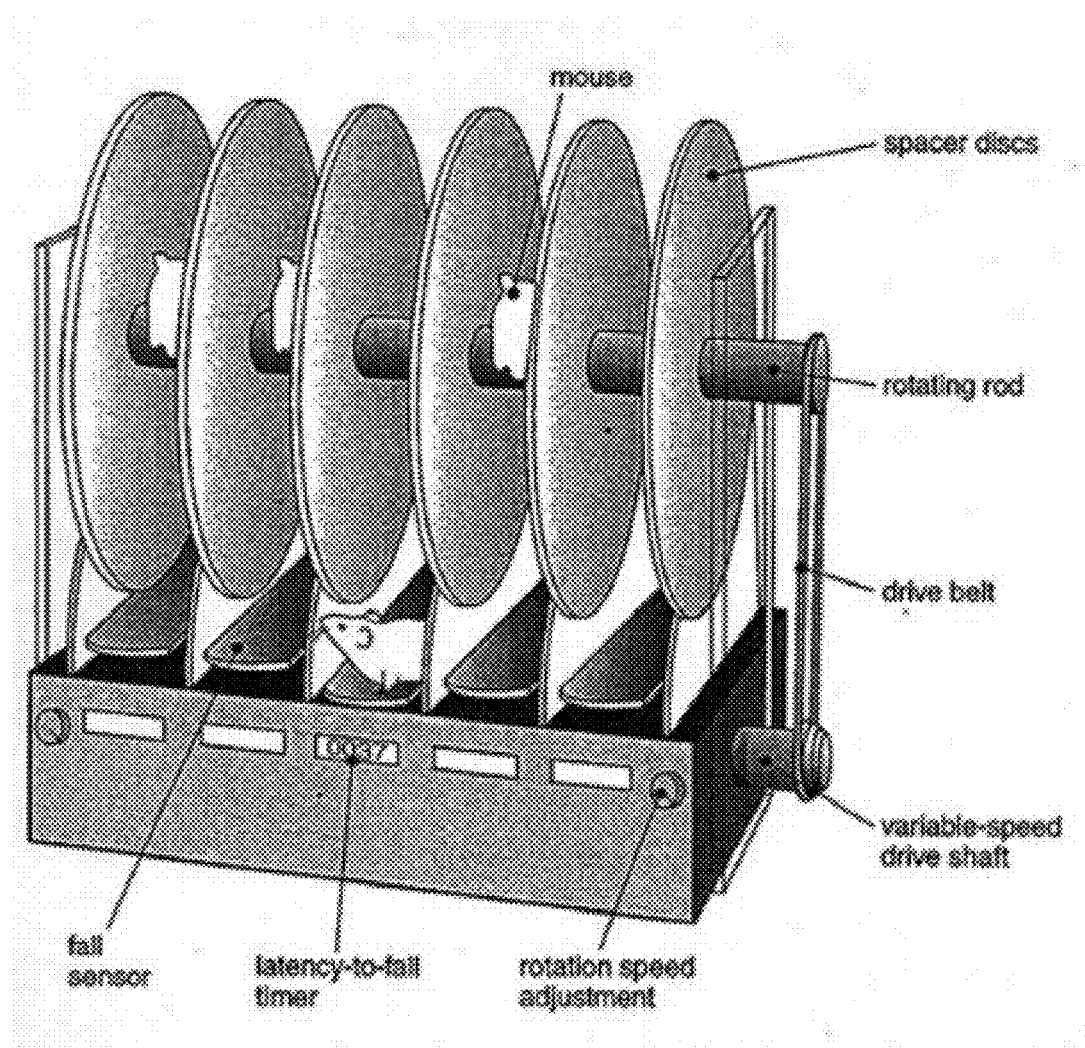
FIG. 11 is an exemplary schematic illustration of a standard rotarod apparatus.

FIG. 11 shows a schematic illustration of a standard rotarod apparatus.

Steps that may be performed may include: 1) Collect behavioral and neural data from rodents during cognitive skill training with and without Vagus Nerve Stimulation (VNS) and 2) Analyze data to quantify changes in synaptic plasticity, validate cerebellar plasticity, develop functional and anatomical maps/models of neural circuitry underlying plasticity, and mine optimized neural tuning parameters from training data, behavioral data, neural data, VNS and TENS stimulation and functional connectivity. Further, embodiments may include a non-invasive, wearable TEACH system for human trials using modified COTS hardware, including a TEACH app/software (including data analysis engine) on a secure, cloud platform. With such hardware, human trials may be conducted, such as 3 training series with and without tVNS. The data may be analyzed to a) quantify changes in synaptic plasticity, b) validate cerebellar plasticity, c) develop functional and anatomical maps/models of neural circuitry underlying plasticity, and d) develop optimization feature from tuning parameters and metrics (training, behavioral data, neural data, tVNS and TENS stimulation and functional connectivity)

In embodiments, software may automatically collect data from rodent experiments in real time with sufficient resolution. Data from the implanted VNS, miniature microscope, and training equipment (Operant chamber, Rotarod, Erasmus Ladder) will all flow into the same data analysis platform, and therefore must be integrated carefully.

In embodiments, software for a miniaturized microscope may include modules that provide the capability for automated collection of images, real-time remote control, an intuitive user-friendly interface, automatic extraction of statistical data from high-quality images, and 3D Roughness Reconstruction applications to interpret sample characteristics from flat 2D images Task Overview: The effect of VNS/TENS stimulation on training and neural plasticity may be measured in three different rodent behavioral tasks combined with in vivo multiphoton imaging. The goal is to 1) demonstrate the feasibility of enhancing learning of relevant tasks by paired VNS/TENS stimulation 2) quantify the extent of enhancement in tasks in three domains (motor acquisition, motor adaptation and cognitive flexibility) for comparison with human trials and 3) quantify neuronal plasticity in vivo before, during and after enhanced learning within these domains using in vivo imaging of relevant neuronal circuitry.

Mice will undergo a period of acclimatization between 10-30 days, housed on a 12 h light/dark cycle (lights on at 7:00 am) with access to food and water ad libitum. Body weight, food intake, home cage behaviors, emotionality, and response to standard cage changing procedures will be evaluated (Wirz et al. 2015).

Once mice are acclimated, A number of mice will be injected with an adeno-associated virus to express GCaMP6 in the hippocampus and cerebellum. They will be put back in their cages for a period of 21 days (time needed for the virus to be expressed in cells). Then, they will be perfused and their brains will be extracted and sliced using a cryostat (or a Vibratome). Brain slices will be imaged under fluorescence microscope in order to confirm our injection coordinates.

For in vivo imaging, we will use 40 mice that will be split into two imaging groups: 20 will be implanted with a miniature microscope, the other 20 will undergo in vivo multiphoton imaging, which requires a hippocampal window implant as described previously by other groups in the field (Dombeck et al. 2010; Gu et al. 2014). Within each imaging group, half the mice will be assigned to receive VNS/TENS and the other half will be the control group.

In all surgeries, mice will be anesthetized with isoflurane (2% at an oxygen flow rate of 600-800 ml/min) and mounted in a stereotaxic frame (World Precision Instruments, Sarasota, Fla.).

The implant procedure of the hippocampal window is composed of a GCAMP vector injection through a small primary craniotomy followed by a secondary craniotomy over the primary site, through which a portion of the cerebral cortex and white matter is removed to expose the hippocampus, after which a transparent window is used to close the wound.

The implant procedure of the mini microscopes consists of a GCaMP vector injection through a small primary craniotomy followed by a secondary craniotomy for implanting the GRIN lens (see FIG. 12) which is then attached to the skull using cyanoacrylate glue and dental cement.

The implant procedure of the VNS consists of making an incision on the medial aspect of the animal's neck to expose the descending branch of the vagus nerve, and wrapping the VNS platinum electrode leads around it. The body of the stimulator is implanted subcutaneously and the wound is closed.

Figure 12:
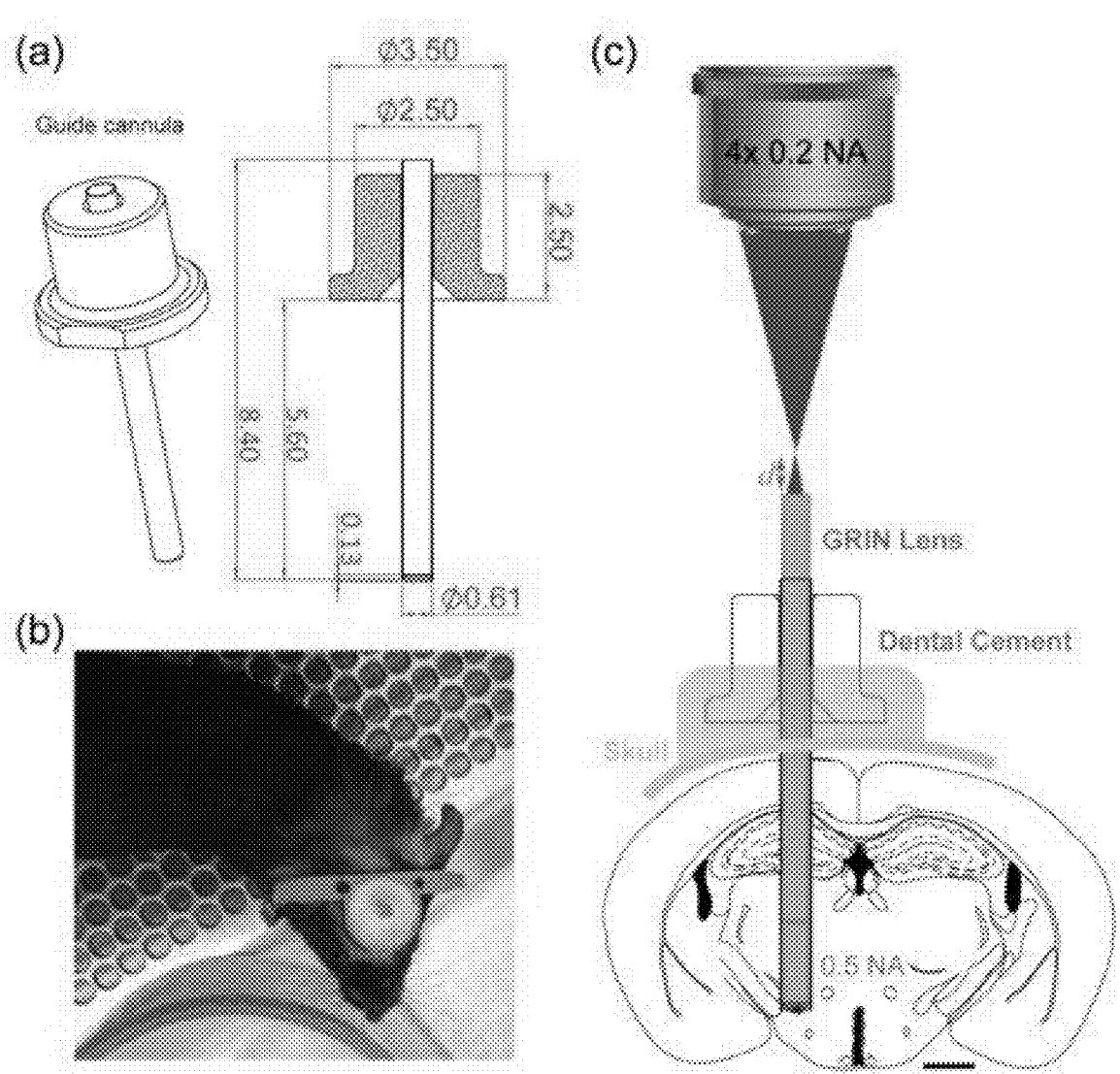
FIG. 12 is an exemplary illustration of an implant procedure of the mini microscopes according to embodiments of the present systems and methods.

As shown in FIG. 12, after surgeries are complete and before training begins, baseline in vivo imaging will take place. Dendritic spines in the hippocampus will be quantified using in vivo multiphoton imaging via the implanted hippocampal window. A similar procedure to quantify cerebellar plasticity following these tasks will be used. Novel fluorescent calcium sensors will be used in rodents to detect single action potentials and calcium transients in individual dendritic spines, for functional analysis of neuronal circuitry before, during, and after VNS/TENS assisted and placebo learning. Imaging of calcium transients during task learning will be performed using a customized miniature microscopy head stage first described by Mark Schnitzers group (Ghosh et al. 2011).

Intra/Extra Dimensional Set Shift Task Training. The intra/extra-dimensional set shift task for mice measures alterations in executive control and cognitive flexibility in an automated version of the Wisconsin card sorting test and CANTAB intra/extra dimensional set shift task, both widely used measures of attentional control in humans.

Animals will be trained to perform a series of compound discrimination and reversal tasks where one stimulus dimension consistently cued reward are forced to switch to a new, arbitrary set of rules. Animals aided by VNS stimulation, 0-100 mA; 2-250 Hz; pulse width 40-250 µs, will be compared to a control group of animals subjected to a sham procedure. Task performance metrics are response latencies, intra- and extradimensional shift ability, number of trials to reach the criterion, time to reach the criterion, and latency to respond.

Training takes 22 days per mouse during which half will be assisted by VNS/TENS stimulation during training. Before and after training in vivo imaging will be performed again to observe the number of dendritic spines pre- and post training of each task.

Rotarod Task Training. To evaluate motor coordination and balance the rotarod task will be used. This test measures the speed of acquisition of a motor skill and cerebellar function. Mice have to keep their balance on a rotating rod. The amount of time (latency) the mouse stays on/falls off the rod will be measured. Depending on performance, level of difficulty can be changed by varying speed (e.g. from 4 to 40 rpm).

Training takes 22 days (parallel to Erasmus ladder and set shift task training) with stimulation during training. Test of rotarod performance daily with increasing difficulty. Mice aided by VNS 0-100 mA; 2-250 Hz; pulse width 40-250 µs and TENS will be compared to the control group subjected to a sham procedure. After training in vivo imaging will be performed again to observe the number of dendritic spines pre- and post training of each task.

Erasmus Ladder Task Training. To evaluate motor performance, the Erasmus ladder task will be used. These tests measure the fast acquisition of a motor skill and cerebellar function by pairing a conditioned stimulus to the traversing of an obstacle using a complex motor task. The apparatus consists of a horizontal ladder between two goal boxes. The mouse traverses this ladder while the touch sensitive rungs allows the system to measure step time and length, missteps, back steps, and jumps, while cerebellar functioning is tested in a challenge that involves a barrier raising during the run.

Training takes 22 days (parallel to Rotarod and set shift task training) with stimulation during training. Erasmus ladder trials will be run at regular intervals with the possibility to increase difficulty as training progresses by forcing the animals to relearn the task under altered circumstances. Mice aided by VNS 0-100 mA; 2-250 Hz; pulse width 40-250 µs and TENS will be compared to the control group subjected to a sham procedure. After training in vivo imaging will be performed again to observe the number of dendritic spines pre- and post training of each task.

Data Analysis and Mapping: Using Fundamental Code Unit based algorithms, we will analyze the structural and functional mapping from peripheral stimulation to brain activity, and use the graph theoretical and general linear model approach to build the map from peripheral stimulation, to brain activity, and to behavioral output, thus to implement the closed-loop neurostimulation system to obtain the optimal noninvasive stimulation methods and the optimal training protocols. The goal of this task is to 1) elucidate the anatomical and functional maps of the peripheral and central nervous system circuitry that regulates synaptic plasticity in the brain (rodents); 2) demonstrate effects of peripheral neurostimulation on brain activity and behavior (rodents) 3) to optimize stimulation methods and training protocols for long-term retention without negative side effects.

Structural and functional mapping from peripheral stimulation to brain activity. Two types of data will be collected from calcium imaging: dendritic spine density (cell growth) and spiking activity (firing rate). We will develop the structural and functional mapping from VNL and TENS to brain activity with these steps:

1. Brain mapping and plasticity analysis with two photon calcium imaging
   a. Imaging Post- and Presynaptic Function In Vitro
   b. Dendritic and Spine Calcium Signals In Vivo
   c. Calcium Imaging in Behaving Animals
      i. Preprocessing and segmentation of calcium imaging data
      ii. Reconstruction of neuronal firing from calcium signals
      iii. Analysis of network activity and mapping
2. Brain mapping and plasticity analysis with electrophysiological data
   a. Functional brain mapping analysis with intracellular recording
      i. Voltage clamp analysis
      ii. Current clamp analysis
      iii. Correlation analysis with two photon imaging
   b. Functional brain mapping analysis with extracellular recording
      i. Develop ICA Spike Sorting
      ii. Test ICA with open-source data
      iii. Compare ICA with other spike sorting algorithms
   c. Correlation analysis between patch clamping, intracellular, and extra-cellular recording
3. Structure-function mapping and plasticity analysis
   a. Structural and functional connectivity
   b. Computational modelling of structural and functional mapping Graph theoretical analysis with peripheral stimulation, brain activity, and behavioral output. Embodiments may graph theoretical analysis with peripheral stimulation, brain activity, and behavioral output to demonstrate the effects of peripheral neurostimulation on brain activity and cognitive skills: 1) Cognitive enhancement demonstration with big behavioral data analysis; 2) Correlation analysis between peripheral neuro stimulation and brain activity; 3) Correlation analysis between brain activity and behavioral output; and 4) Correlation analysis between peripheral neurostimulation, brain activity and behavioral output a) General Linear Model Approaches, b) Subtraction Analyses, and c) Connectivity Analyses.

Closed-loop neurostimulation optimization. Embodiments may include a closed-loop neurostimulation optimization system to analyze neural data online during experiments, and use the results to change an experiment protocols as well as perform targeted manipulations of neural activity: 1) Sample of peripheral stimulation, to brain activity, to behavioral output; 2) Train the network with supervised learning method; 3) Test the network with cross validation; and 4) Minimize the cost function to get the optimal noninvasive stimulation parameters and training protocols.

Scientific Rationale. Enhanced performance on motor, cognitive flexibility and linguistic tasks may be due to heightened cerebellar error-processing/predictive inference abilities. More specifically, bottom-up error-processing/predictive inference capabilities via LC-NE activity may be provided. Behaviorally we expect improved error learning (decreased number of errors) and shorter response latencies (faster response time) particularly for concordant predictive conditions (high predictive inference). Put together, this would suggest faster automation of skill acquisition and adaptation.

The cerebellum has ½ of all neurons in the brain. Its role in movement and motor control has been well studied and more recently it has been implicated in a range of cognitive functions as well. Many suggest a more domain-general role for the cerebellum as an error-processor, implying that the cerebellum's role in cognition is similar to its role in motor control. Cerebellar error-processing and predictive inference capabilities may be enhanced according to Aston-Jones & Cohen's (2005) Locus Coeruleus-Norepinephrine (LC-NE) Adaptive Gain and Optimal Performance Theory. In line with this, an LC-NE's bottom-up mechanism may aid the cerebellum, thereby encapsulating optimized executive attention/arousal control.

Embodiments may use a combination of two non-invasive peripheral stimulations (tVNS and TENS); three different task domains (motor, cognitive flexibility and linguistic), heavily reliant on predictive inference and/or error-processing skills, across a range of varying levels of difficulty and different training and stimulation protocols, to enable superfluous coupling of stimulation onset and latency across different training phases and demands.

Understanding the LC-NE System. NE can optimize performance on a variety of learning and memory tasks due to its role in modulating arousal. Aston-Jones and Cohen (2005) differentiate the role of tonic LC-NE activity in regulating attention/arousal, with low-levels of tonic LC-NE activity corresponding to inattentiveness, while high-levels of tonic LC-NE activity correspond to distractibility. Optimal attention/arousal control falls somewhere in between. Their Adaptive Gain Theory suggests that LC-NE may be responsible for modulating arousal/attention by enhancing the signal-noise ratio. An increase in gain increases the activity of neurons receiving excitatory inputs and decreases those receiving inhibitory inputs. This increases signal-noise ratio by bolstering contrast between activated and inhibited units. Therefore tonic LC-NE activity can be used to help optimize the explore-exploit tradeoff in the brain (how the brain distinguishes between what is relevant and what is not; such as regulation of attention) especially with its interactions with utility. Specifically, tonic LC-NE activity is inversely proportional to utility, whereas dopamine has been shown to be involved in the encoding of utility (Wiecki & Frank 2013; Hazy et al. 2007; Frank 2006). This is consistent with the effect of increasing tonic LC-NE activity on performance on tasks that require focused attention (Aston-Jones & Cohen 2005). Put together, these describe ways that tonic LC-NE activity may be regulated in either a top-down (due to increased conflict/task demands) or a bottom-up (due to stimuli specific saliency) manner and provide a good framework for our current understanding of executive function without the need of a homunculus.

NE and DA both interact with 5HT such that tonic LC-NE activity has innervations in DRN (Dorr & Debonnel 2006). 5HT has more recently been investigated as a motivational opponent to dopamine in learning and decision making (Dalley & Roiser 2012; Cools et al. 2011; den Ouden et al. 2013; Shiner et al. 2012; Economidou et al. 2012; Seymour et al. 2012; Geurts et al. 2013). The mechanisms of 5HT in executive function are not as clear compared to the proposed mechanisms for DA and NE, as there are a number of 5HT receptors throughout the brain. The interaction between 5HT and dopamine helps to explain how the brain mediates between stay/switch modes (similar to explore/exploit) and why increased 5HT has been associated with both increased compulsivity (excessive stay) and increased impulsivity (excessive switch) across different people and studies. Most studies suggest that the specific effect of enhancing 5HT depends on underlying neurochemistry particularly in respect of baseline dopamine activity in the brain and the level of saturation in 5HT receptors in the brain.

Both computational (Sikström & Söderlund 2007; Nieuwenhuis, Gilzenrat, et al. 2005) and pharmacological (Doll et al. 2011) studies describe that the effect of increasing tonic dopamine or NE activity on cognition (in the BG and LC respectively) may depend on the underlying neurochemical activity (Frank & Fossella 2011; Frank et al. 2009; Doll et al. 2011; den Ouden et al. 2013; Cools et al. 2009; Collins & Frank 2013). In a hypo-functioning dopamine system, such as ADHD (Sikström & Söderlund 2007; Nieuwenhuis, Gilzenrat, et al. 2005) or aging (Hong & Rebec 2012b; Hong & Rebec 2012a; Allard et al. 2011; Bäckman et al. 2006) increasing tonic dopamine activity may enhance attention regulation and improve performance (Sikström & Söderlund 2007), whereas in a hyper-functioning dopamine system, increasing tonic dopamine activity may cause cognitive and motor rigidity (Parkinson's). This explains why stimulant medications and treatments effective for treating attention deficits in those with ADHD often have an opposite effect for those who do not. Similarly, increasing tonic LC-NE activity in a hypo-functioning LC-NE system may enhance arousal and increase cognitive engagement in task and flexibility thereby improving performance but actually worsen performance in a hyper-functioning LC-NE system by causing excessive distractibility. Since tonic LC-NE activity is inversely proportional to utility, NE and dopamine interactions may be most salient at the start of learning and in high conflict/high uncertainty tasks (high demand) where utility is low.

Stimulating the vagus nerve invasively induces production and release of neurotransmitters, namely norepinephrine (NE) production in the Locus Coeruleus (LC), dopamine (DA) production in the Nucleus Accumbens (NA) and serotonin (5HT) production in the Dorsal Raphe Nucleus (DRN). Increasing the release of these neurotransmitters also increases the concentration of the neuromodulators acetylcholine (ACh) and elevated levels of inhibitory GABA (Manta et al. 2009; Boon et al. 2006; Frangos et al. 2015; Hays et al. 2013; Van Leusden et al. 2015; Don & Debonnel 2006; Ghacibeh et al. 2006b; Jacobs et al. 2015; Smucny et al. 2015; McIntyre et al. 2012; Roozendaal & McGaugh 2011; Fang et al. 2016). It has been suggested that VNS may modulate cortical plasticity and memory via synergistic interaction of multiple neuromodulators (Peña et al. 2014; Dorr & Debonnel 2006). The literature is rich in evidence for the role of all these neuromodulators/neurotransmitters in enhancing cognitive control, however the exact relationship between VNS and cognitive function is poorly understood and needs to be further explored. This means that improved cognitive performance is more likely due to a combination of neurotransmitter and neuromodulator systems and their interactions rather than LC-NE activity alone.

Several studies suggest that enhanced cognitive capabilities by VNS or tVNS are predominantly due to increased LC-NE activity. This is consistent with the fact that the Vagus Nerve has direct efferents on LC but not on DRN (Manta et al. 2009) and that VNS has a quicker and more robust effect on NE relative to 5HT and DA firing rates (Dorr & Debonnel 2006; Manta et al. 2009). Further, the LC has connections to and from the DRN and NA allowing ample opportunity for cross-modulation between NE, 5HT and DA responsible for cognitive improvement. Put together these suggest that reported enhanced cognitive performance following tVNS and VNS due to LC-NE activity and its influence on other neurotransmitter and neuromodulator systems.

What is more LC-NE activity has downstream effects throughout the entire brain including the cerebellum, amygdala, hippocampus, BG, dlPFC, ACC and OFC (among others) each of which have been implicated in cognition. This means that even if LC-NE activity framework encapsulates theoretical framework for enhanced performance, it is likely that any witnessed performance effect is consequence of LC-NE's influence across a number of different neural pathways/loops rather than confined to the cerebellar mechanism proposed here.

Why tVNS and TENS Together? To better map specific neural underpinnings, embodiments may utilize TENS to isolate the cerebellum by subtracting the stimulation effect from the rest of the brain. The exact mechanism of TENS treatment effects are not known for certain. However, some things can be inferred about its mechanism of action: TENS stimulation seems to inhibit nociceptive C-fiber activity in experimental and clinical pain trials as well as stimulate proprioceptive Aβ-fibers. Both C-fiber inhibition and Aβ-fiber excitation could potentially be manipulated using very simple devices to accelerate training. Nociceptive C-fiber projections to the anterior midcingulate cortex have been implicated in cognitive control and could be used to tune attention to a training task (Shackman et al. 2011).

Using a combination of tVNS and TENS allows embodiments to better probe possible neural mechanisms involved/extent of influence in enhanced learning performance across motor, cognitive, and linguistic tasks. For example, tVNS inhibits the hippocampus and excites the cerebellum (Frangos et al. 2015), whereas TENS stimulates the cerebellum with minimal effect on other areas such as the hippocampus. The cerebellum and the and the hippocampus are both implicated in early learning with a decreasing involvement as learning becomes consolidated (D'Angelo & Casali 2012; Baillieux et al. 2008; Mariën & Beaton 2014; Atallah et al. 2004; Frank et al. 2006; Bornstein & Daw 2012; Badre et al. 2014; Milad et al. 2009). (Brashers-Krug et al. 1996; Cohen & Robertson 2011; Alvarez & Squire 1994; Seitz et al. 2005; Yotsumoto et al. 2009; Yotsumoto et al. 2013; Hung & Seitz 2011). Therefore using a combination of both stimulation types may further elucidate neural mechanisms involved and provide a better more reliable framework for reproducing results with minimal side effects.

Rationale: Training and stimulation protocols. In embodiments, the selected tasks, training and stimulation protocols for rodents and humans, may allow us to gauge the extent of enhanced performance. More specifically, enhanced performance on the selected tasks depends on predictive inference and/or error-processing skills thought to be associated with the cerebellum (Stoodley & Schmahmann 2010; Krigolson & Holroyd 2007). Cerebellum has also been implicated in early learning (Penhune & Doyon 2005; Hikosaka et al. 2002; Bastian 2006) and with increased task demand/conflict (Stoodley 2012). Therefore, embodiments using broad range of stimulation protocol modulating range of latencies and onsets may provide for further examination of LC-NE and cerebellar influence on enhanced performance. Pupilometry measures have been predictive of level of LC-NE activity and its engagement in high demand/conflict cognitive tasks (Murphy et al. 2014; Gilzenrat et al. 2003; Aston-Jones & Cohen 2005). Therefore, adding pupilometry across different task domains further enables examination of the effect of LC-NE activity in enhancing cognitive performance.

Why EEG. EEG is a reliable technique for exploring functional activity of the brain, because it is sensitive to changes in neural plasticity related to LTP-like phenomena, thus it can be used to investigate functional connectivity and to explore how neural networks are organized and interact. Although fMRI has better spatial resolution and signal to noise ratio, EEG has its advantages over other techniques in terms of temporal resolution and portability. EEG can explore real-time spontaneous electrical brain activity with a millisecond temporal resolution. EEG recordings should be able to show synaptic plasticity, as it has been used in combination with neuroimaging and TMS to map patterns of brain activation (Roy et al. 2016).

Possible side effects. The vagus nerve, the longest cranial nerve, provides an excellent point for stimulation, because it is a central nerve connecting to many other systems within the body. It contains motor and sensory fibers and, because it passes through the neck and thorax to the abdomen, has the widest distribution in the body. These interconnections may be advantageous for targeting neuroplasticity, but could introduce the risk of potentially harmful side effects. Side effects of tVNS are minimal and usually disappear soon after stopping stimulation. Possible side effects include itching, discomfort in the area of the outer ear and local pain at the stimulation site. tVNS uses less current than existing FDA-approved VNS implant treatment for seizures and depression, so adverse effects are unlikely. Furthermore, tVNS allows for high temporal specificity (by controlling stimulation onset and latency) meaning that it is unlikely for any unrelated task behaviors to have long term effects. However, precaution may be taken to mitigate possible side effects. The most effective means of avoiding risk may be strict inclusion/exclusion criteria for human subjects. For example, subjects may have to be within a certain age range, and not have existing or history of medical conditions.

Cardiac. Cardiac side effects of tVNS are possible, but unlikely. A clinical pilot study testing the safety of tVNS on patients with chronic tinnitus concluded that in subjects with no known pre-existing cardiac conditions, tVNS does not cause arrhythmic effects (Kreuzer et al. 2012). As an extra precaution, embodiments may only stimulate the vagus nerve from the left ear.

Although unlikely in a human study, excessive activation of the vagal nerve (usually during emotional stress) can cause vasovagal syncope due to a sudden drop in cardiac output leading to cerebral hypoperfusion. It can also lead to temporary loss of bladder control under moments of extreme fear. To avoid responses like these we may closely monitor heart rate, body temperature, breathing rate, and pulse oximetry during all periods of training and stimulation even with subjects receiving sham stimulation. These biosensors are already built into the INTENT Earbud and we may include automatic risk/warning indicators within the software.

Mood/Anxiety. The Cognitive side effect profile of VNS is positive, however we may use a batch of standard mood/anxiety evaluation tests (both in rodents and human studies) to monitor cognitive changes. Stimulating the Vagus nerve may cause global increase in monoamine production in brainstem, which can lead to changes in mood/anxiety. Negative side effects are highly unlikely given that tVNS and VNS have been both been found effective in reducing mood and anxiety pathologies, such as treatment resistant depression (Nemeroff et al. 2006; Park et al. 2007; O'Keane et al. 2005; George et al. 2008; Furmaga et al. 2011)

Inverted U Shaped/Stimulation and intensity. Several studies have observed an inverse U-shaped relationship between stimulation intensity and cognitive performance (Ghacibeh et al. 2006a; Boon et al. 2006; Van Leusden et al. 2015). Clark et al. (1995) found that rats who received an intermediate level of stimulation (0.4 mA) intensity demonstrated significantly better avoidance memory compared to those that received 0.2 mA, 0.8 mA, or the control condition. A follow up study in epilepsy patients corroborated the inverted-U pattern with results showing that intermediate stimulation intensity yielded the best performance in a recognition memory task (Clark et al., 1999). To account for this, embodiments may utilize a range of stimulation intensities for calibration and to include data analysis. Furthermore, embodiments utilize an intermediate level of stimulation.

Figure 7:
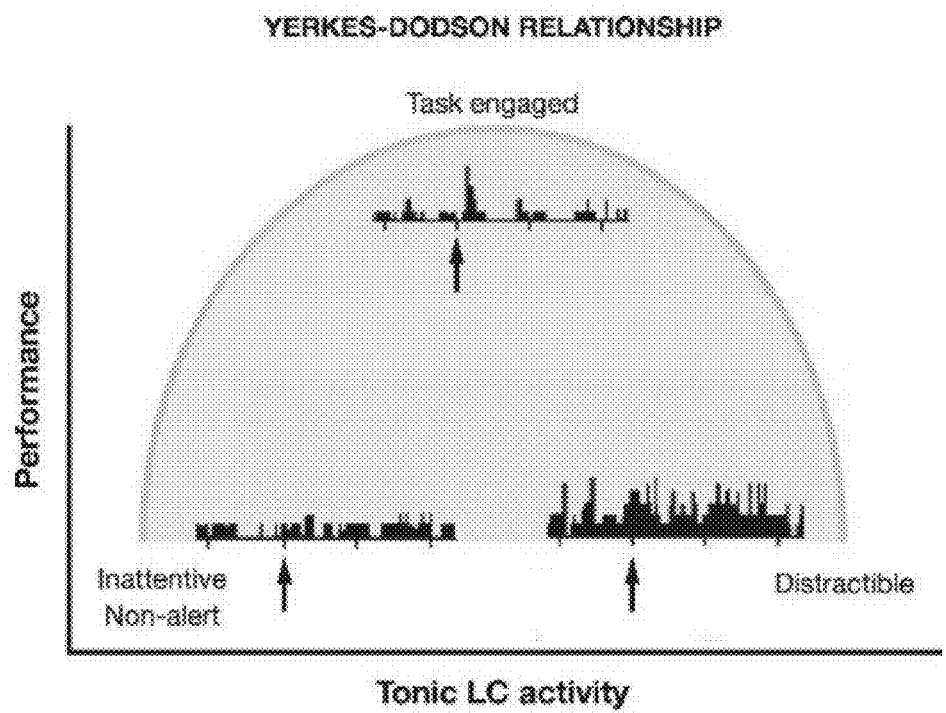
FIG. 7 is an exemplary illustration of the inverted-U relationship between LC activity and performance on tasks that require focused attention.

FIG. 7 (Aston-Jones & Cohen 2005) illustrates the inverted-U relationship between LC activity and performance on tasks that require focused attention. Performance is poor at very low levels of LC tonic discharge because animals are drowsy and nonalert. Performance is optimal with moderate LC tonic activity and prominent phasic LC activation following goal-relevant stimuli (phasic LC mode). Performance is poor at high levels of tonic LC activity (tonic mode, lacking phasic LC activity). This resembles the classical Yerkes-Dodson relationship between arousal and performance. (Aston-Jones et al. 1999).

Because tVNS technology is fairly novel, it has not yet developed an established experimental paradigm. Therefore, there is no gold standard for appropriate patient selection, optimal stimulation intensity, or duration. To address this challenge, we may have strict subject inclusion criteria and we may test various levels of stimulation intensity and duration with various difficulty levels for each cognitive training tasks. For example, in some studies, all subjects may be right handed to account for any possible individual differences confounding the data.

Many studies have observed that the success of a tVNS protocol is highly dependent on the targeted cognitive function and desired outcome (Hays et al. 2013). VNS has to be applied with a high degree of temporal precision to ensure that only the intended events are inducing long-term changes on the molecular and behavioral level and to make sure that effects are not attenuated with time, as is often the case with pharmacological approaches (Hays et al. 2013). The effect of VNS on cognitive/motor performance may depend on the time and duration of stimulation within a particular task and subject. The specific mechanisms by which VNS enhances performance may likewise rely on the stage of learning and the level of uncertainty associated with it. Therefore, we may include a series of levels and challenges for each training task. So, for example when a subject comes for their first training session they may start with task level 1, at their next session the following week may continue to level 2 depending on their performance.

Using two different stimulation methods may be more useful for mapping brain mechanisms involved. Embodiments may use two kinds of peripheral stimulation, namely VNS and TENS. There is evidence of TENS stimulation yielding proprioceptive AP excitation, which is known to project indirectly to the cerebellum, but not other parts of the brain (such as the hippocampus). Using a combination of these stimulation types may provide a better approach than using one alone, because we will be able to better correlate witnessed results to the proposed neural mechanism. Understanding the mechanisms behind the witnessed effects is of utmost importance in order to reliably reproduce positive results with minimal negative side effects.

Using tVNS allows great temporal specificity (stimulation onset and latency) in coupling stimulation with stimuli and task conditions. This may deepen understanding of neural frameworks involved, allows for successful reproduction with minimal negative side effects and allows for more specific and efficient training protocols.

All tasks are highly dependent on predictive inference/error-processing abilities thought to be associated in a domain-general way with cerebellum. Using combination of tasks within different domains but reliant on similar mechanisms furthers the validity of this effect across a range of functions. If results are consistent across motor, cognitive flexibility and linguistic tasks here proposed, the generalizability of the effects across even more domains is more likely. This is powerful because it allows for expansion beyond this proposal's specific task set.

The human experiments were designed to relate to the real-world tasks within specific use cases, where motor function, executive decision making and verbal proficiency can be crucial. While the technique presented here has potential for academic applications, the proposed neural mechanism here incorporates real world applications (high conflict/demand) not limited to laboratory settings.

The specifics for how the cerebellum contributes to cognition is not yet understood. There is plentiful research for how LC-NE activity enhances executive function in the brain improving performance on a series of tasks. Embodiments may expand on well-developed computational neural network models to include the cerebellum as an error-processor enhanced by LC-NE activity. The effects of LC-NE activity on executive function have been reliably reported and reproduced in a series of investigations across a myriad of brain areas and experimental paradigms.

Embodiments may include ways to closely monitor possible cardiac and mood/anxiety negative side-effects. While cardiac side effects are avoidable to a very large degree by stimulating unilaterally, the risk of transient stimulation effects on cardiac rhythm cannot be excluded. For this reason, ECG may be monitored to alert of possible arrhythmia. Negative effects on mood may be unlikely given that VNS and tVNS have been associated with attenuated mood/anxiety symptoms rather than increase. Embodiments of a tVNS stimulation protocol described herein entails significantly less stimulation intensity and latency compared to FDA-approved VNS protocols used to treat treatment resistant depression among others. Further, tVNS allows for high temporal specificity (by controlling stimulation onset and latency) meaning that it is unlikely that it any unrelated task behaviors to have long term effects.

Accordingly, described embodiments may provide an advantageous approach to target enhanced performance, such as neuroplasticity, across a range of task domains and difficulties within a single underlying neural mechanism. Embodiments may provide an efficient way to enhance learning across a range of cognitive skills, task domains and levels of difficulty instead of being limited to one specific experimental protocol, as is the case with conventional techniques.

Further, embodiments may include adaptations to the methodology to better accommodate other possible mechanisms through which tVNS may enhance cognition. This is made possible due to broad effects of tVNS on monoamine brainstem production and their possible roles in different areas at different phases of learning.

Potential Impact. Embodiments of the present systems and methods may be beneficial for all levels of military personnel and civilian applications. Embodiments may include an optimization feature to modify neurostimulation in real-time to achieve optimal cognitive enhancement would broaden possible application areas. Not only would a system capable of real time, personalized neuromodulation be valuable to the military, but could also be a tool for education and health. Embodiments may include techniques for understanding the anatomical and functional maps of the peripheral and central nervous system circuitry that regulates synaptic plasticity in the brain. Embodiments may include techniques for understanding how the hippocampus and cerebellum interact with the Basal Ganglia (BG) in order to elucidate mechanisms of learning and decision-making specifically when uncertainty is high. This may be important because although the Basal Ganglia Reinforcement Learning computational framework is quite apt for predicting human behavior in tasks with little conflict, it cannot by itself explain the individual differences reported in the literature specifically in tasks more akin to the real world in their high uncertainty level. Decision-making in the real world is often not clear cut and learning is often not explicit. Understanding how people deal with uncertainty is important to understanding human executive function. In embodiments, a cloud repository could be a big brain data processing center for future brain science research.

Embodiments may be used for enhanced learning of motor, cognitive flexibility and verbal tasks in humans as a result of paired VNS/TENS stimulation protocols.

Visio Motor Skill Task. The Visio Motor Skill Task may be used to assess motor acquisition and adaptation skills across a range of different task difficulties and experimental protocols (Reis et al. 2009). This framework allows for better approximation to real world motor learning scenarios. Participants manipulate a joystick to move a cursor on computer screen in front of them through a series of gates/target points in a particular sequence order (see FIG. 15). Movement time per trial will be defined as time taken to complete entire sequence. Errors will be understood as failure to reach target (undershoot), and passing target gate (overshoot). Sequence errors will also be noted and analyzed separately. Performance will be measured as error rate. Error rate will be calculated as the proportion of trials with at least one overshooting or undershooting movement per epoch. Other measures of performance include: positions of the cursor, speed of the cursor, speed-accuracy tradeoff function, cursor movement reflective of the motor skill, eye movement (pupilometry), and online/offline effects. We anticipate a decrease in error rate after the first few trials for all subjects regardless of stimulation.

In embodiments, a motor acquisition and a motor adaptation version of the task may be used, which will use the same interface and task structure, but which may include a specific training and stimulation protocol adapted to better probe underlying cerebellar influence responsible for enhanced performance (expressed by reduced number of errors).

Figure 14:
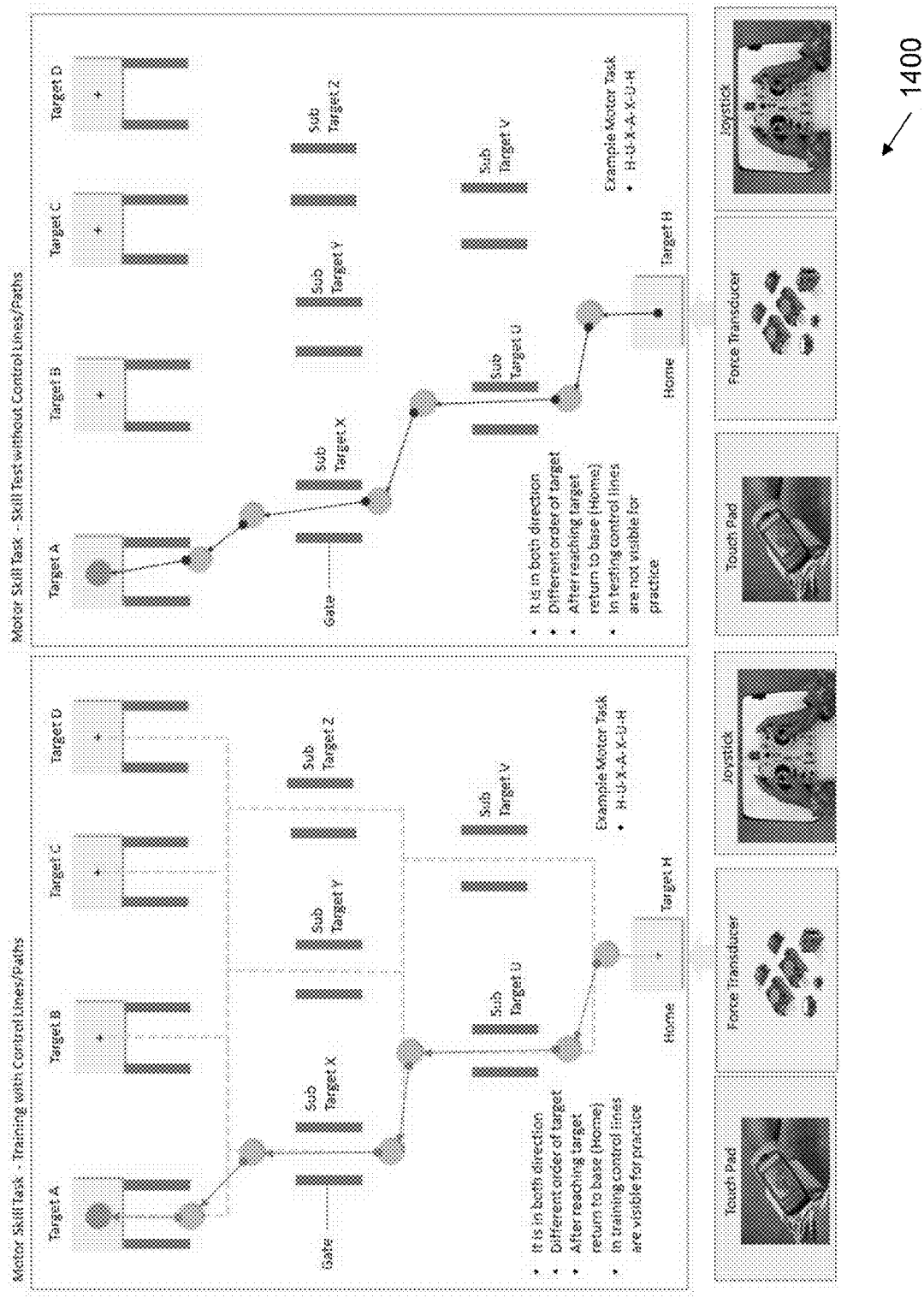
FIG. 14 is an exemplary illustration of Visio Motor Skill Task according to embodiments of the present systems and methods.

An example of a Visio Motor Skill Task with different level of difficulties and learning targets is shown in FIG. 14. In this example, 50 healthy subjects will be recruited by two research coordinators with the support of GU administrative resources. All subjects will be right-handed and provide informed consent prior to participation. Stimulation will be administered in a double-blind fashion. Half of the participants will receive tVNS and the other half will receive sham stimulation. For our sham procedure we will switch the tVNS on for a short period of time, allowing the subject to perceive the stimulation. We will then turn the stimulation off completely and tell the subject that we are still stimulating but are decreasing the charge to an imperceptible level, asking them to state when they are no longer able to perceive it. Since TENS delivers an electrical current through the skin to produce pain relief, patients can typically feel the stimulation under the electrodes. The standard placebo in prior clinical studies has been to utilize a unit that appears to be functioning (lights on) but does not deliver a current. In this case the subject would not feel the stimulation. We will compare this standard placebo to a new device in which a current is delivered for 30 seconds and then slowly ramps to off. This current would then be felt by the subject as intensity is set, and then would slowly ramp down. Thus, electrical currents will be felt by the subject, without most or all of the stimulation effect of TENS (Anon n.d.).

For all sessions, subjects will provide information on sleep duration of the previous night, sleep quality, tiredness, attention, general fatigues of the trained hand, possible discomfort elicited by the tVNS, perception of the intensity of the tVNS, and potential distraction elicited by the tVNS, using questionnaires and visual analogue scales. They will also complete a Positive and Negative Affect scale (PANAS), a 20-item self-report measure before and after the training period to screen for both potential short-term (within session) and/or long-term (across sessions) effects of tVNS on mood (regardless of direction). In this assessment negative affect will reflect dispositional dimensions, with high negative affect epitomized by subjective distress and unpleasant engagement, and low negative affect by the absence of these feelings. Positive affect represents the extent to which an individual experiences pleasurable engagement with the environment or again the absence of these feelings. The scores of the questionnaires and ratings (1-10) on the visual analogue scales will be averaged per session and subsequently used for comparison across groups. Heart rate, body temperature, and pupil size will also be monitored throughout task to help probe at predictive-inference capabilities and regulate for any possible cardiac side effects. P300 EEG response will also be noted for comparison and data analysis purposes.

Series 1: Motor Acquisition. Each subject will attend a one hour training session each week for a total of 14 sessions. Each training session will consist of six blocks with the first and last block being test blocks (with no stimulation) and the middle four blocks being training blocks (with stimulation). Each session will examine performance on a specific motor sequence. Timeline is broken down into 4 different task demand manipulations with 3 sessions each and 2 testing-only sessions separated from other sessions by a 2 week period.

Sessions 1-12 will be broken down into 4 different task demand manipulations each 3 sessions long.

Sequence length manipulation—sequence length will start with 4 target gates and increase by 1 additional target gate for each session until sequence length totals 7 target gates (average digit span capacity).

Sequence predictability manipulation—sequence length will remain stable at 5 target gates but the predictability of the sequence will change to increase difficulty (less predictable=harder).

Moving target manipulation—sequence length will remain stable at 4 but target-gates will move around screen at different velocities Target width manipulation—target gate width will decrease gradually, increasing dexterity necessary for success.

The sequence path may be delineated during the initial 10 training trials within each block, but will not be present during testing blocks. Starting from the second week onwards, the first and last blocks will also assess performance on the prior week's motor skill (offline effects—short term). Feedback will be given both visually and audibly during training (errors are signaled with buzz sound and task aim is reinforced), but not during testing blocks. The sequence path will also be delineated after each error with a red dotted line to exemplify what should have been done for success. The order of task manipulations will be counterbalanced across subjects to account for possible ordering effects.

Sessions 13 & 14 may be shorter testing-only sessions. There may be a 2 week break between session 12 and 13, 13 and 14. Performance across all motor skills learned in first 12 sessions is assessed to probe at offline effects.

Stimulation Specifics. Both stimulation types will be temporally combined with training but not testing blocks. Stimulation frequency, intensity and latency (duration) will increase across training blocks within and across sessions such that final training block of final session. Both high- and low frequency TENS stimulation has been shown to induce C-fiber inhibition and proprioceptive excitation (Desantana et al. 2009). For this study, high frequency stimuli between 80-100 Hz (200 μsec, 2 mA) may be used, as these are the most commonly described parameters in randomized controlled trials in humans (DeSantana et al. 2008). Stimulus frequency may be adjusted so as to not cause unnecessary discomfort and maximum pain relief on a self-report scale.

Series 2: Motor Adaptation. Each subject may attend a one hour training session each week for a total of 8 sessions. Each session will consist of 3 training blocks (with 50 trials each) and 5 test blocks (with 5 trials each) for a total of 8 blocks. Training and testing blocks are intercalated such that blocks 1, 3, 5, 7 and 8 are testing blocks and blocks 2, 4, and 6 are training blocks. Training blocks will have a path delineated in red throughout the first 25 trials, but path will only appear after errors in the remaining 25 trials as feedback (analogous to what was described for the motor acquisition task above).

The first test block (block 1) may provide a measure for subject baseline performance for a specific motor skill evaluating subject performance with no training. The second test block (block 3) will evaluate motor acquisition performance post training, but prior to any adaptation (identical to motor acquisition task). The third test block (block 5) will evaluate performance post motor adaptation training. The final 2 test block (block 7 & block 8) will evaluate performance on either initial or adapted skills looking into possible effect of conflict.

Motor adaptation skills may be manipulated across 3 different domains with 2 sessions per domain and a final 3 generalization sessions (1 for each domain). Domains include: moving target, target width, and sequence order. Sequence length will be kept constant at 4 target-gates throughout. Subjects cannot have 2 sessions within the same domain back to back thereby reducing facilitation effects from prior week's experience. This means that sessions will always be intercalated with 1 session per domain separated from the next session by >1 week. To account for possible ordering effects, initial session domain may be counterbalanced across subjects. The focus will be on online effects on error-rate and response latency performance measures, but offline effects and generalization capacities can also be measured. Proposed specifics are highlighted below.

Sessions 1-6 will be moving target sessions. Initial test block provides baseline performance with no target movement. Subjects undergo extensive training (block 2) to habituate motor response. The extent of this effect will be measured in the second test-block (block 3). Subjects then undergo extensive training (block 4) to adapt motor behavior to a target that moves at a set speed. The extent of this effect is measured in the third test-block (block 5). In block 6, subjects undergo extensive training to readapt to initial conditions (no movement). In the two test blocks (blocks 7 and 8 respectively) subject performance will be measured for both initial (no movement) and adapted conditions.

Target width session 1 (target width versus half of target width).

Sequence order session 1 (gate sequence order changes from more predictable, such as chronological left-right visually to less predictable)

Moving target session 2 (target speed versus 150% of target speed)

Target width session 2 (half of session 1 target width versus 150% of session 1 target width).

Sequence ordering session 2 (gate sequence changes from less predictable to more predictable).

Sessions 7-9 will be generalization sessions. These final generalization sessions will be longer test-only blocks. Meaning that the subject has to adaptively learn without training. For these sessions, maladaptive behavior is linked to a descending tone and correct behavior to an ascending tone. Other than this no other feedback will be given.

Moving target session 3

Target width session 3

Sequence ordering session 3

Stimulation specifics. Both stimulation types will be present for both training and testing blocks across all sessions. The exact protocol for stimulation will differ for training vs testing blocks. More specifically, stimulation will be more temporally bound for training blocks than testing blocks. During training, stimulation intensity will be of a preset intensity in the first number of trials and then taper off at a linear rate until no stimulation is present. During testing, stimulation intensity will be lower, but stimulation will be present for entire trial duration for half of the trials. Stimulated and sham stimulation trials will be intercalated.

Predictive Language Processing. An expanded version of Visual World Paradigm Task may be used to measure predictive processing in language (Lesage et al. 2012; Lesage et al. 2014; Miall et al. 2014; Miall et al. 2016). More specifically, the experimental procedure will be adapted to include tVNS and TENS rather than tDCS. Other modifications will be made to have varying levels of task difficulty to further examine predictive language processing across different tasks within the visual world paradigm.

In this example, 50 healthy subjects will be recruited by two research coordinators with the support of GU administrative resources. All subjects will be right-handed and will provide informed consent prior to first session. Stimulation will be administered in a double-blind fashion. Half of the participants will receive tVNS and the other half will receive sham stimulation. For details on the sham procedure please refer to 3.2 Training Series 1. For all sessions, subjects will provide information about previous night sleep, affect, mood etc. using questionnaires and visual analogue scales (see Task 3.2 Training series 1 for more details). Heart rate, body temperature, and pupil size will be monitored throughout every task to help probe at predictive-inference capabilities and regulate for any possible cardiac side effects. P300 EEG response will also be noted for comparison and data analysis purposes. For each subject, we will try to conduct sessions at the same time/day of the week to reduce confounding effects. Each subject will attend a 1 hour session each week.

Figure 15:
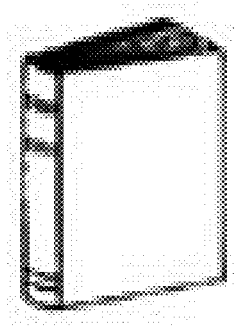
FIG. 15 is an exemplary illustration of a predictive world paradigm task according to embodiments of the present systems and methods.
Figure 15:
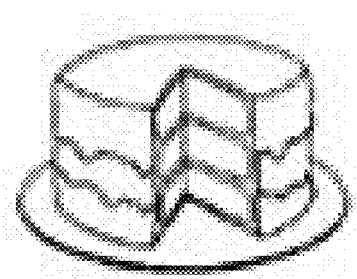
Figure 15:
Figure 15:
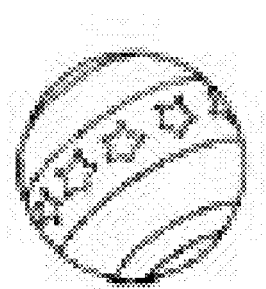
Figure 15:
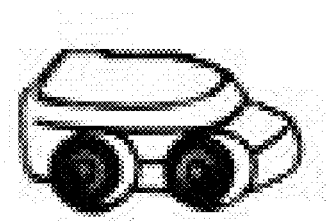

Each trial will consist of a familiarization phase and a decision phase. During the familiarization phase subjects will be instructed to look at all the stimuli (images or words etc.), which will be placed equidistant from a central fixation point on a screen, as shown in FIG. 15. FIG. 15 is an illustration of a predictive world paradigm task showing stimuli equidistant from the fixation point in the middle of the screen (Lesage et al. 2012; Lesage et al. 2014; Miall et al. 2014; Miall et al. 2016).

tVNS and TENS stimulation will be administered at this point within the initial seconds of each trial (familiarization phase) prior to agent (session 1) or question/test stimuli (sessions 2 & 3). The length of familiarization phase of each trial will vary according to specifics of each session. Once stimulation is administered participants hear a buzz and will look to the fixation point in the middle where a stimulus appears. Prior to the each task subjects will be given detailed instructions about what to expect and how to respond.

To help account for ordering effects half the subjects will do session a) then b); the other half of the subjects will do session b) then a) in sessions 1-3. Trial presentation will be randomized so that the order of specific 'questions' and stimuli presentation at fixation point will be different for all subjects further limiting possible confounding factors.

Session 1: Easy—Predictive. As soon as the participant is fixated on the face of the agent, a pre-recorded sentence will be played over headphones. Participants will be instructed to look at an object) on the screen. Response latency (how long it took to look at the object), accuracy (did the subject look at the correct object) pupil diameter (uncertainty/measure of task difficulty) will be measured for each subject across trials. Session 1(a) will have 4 stimuli and session 1(b) will have 8 stimuli. Adaptations will be made to account for increased stimuli but otherwise the display will remain the same.

In this session the instruction will be a simple sentence (about 5 words). There will be 3 conditions: baseline, predictive-concordant and predictive-discordant. Conditions differ from each other in terms of sentence structure, and whether or not the verb predicts the target object/response. The difference between Prediction and Control sentences is the verb, which will either refer to only one of the objects on the display (Prediction condition), or to any of the objects in the display (control condition). The difference between the Misleading and Prediction sentences is the object, which will agree with the sentence verb (Prediction condition), or will not agree (misleading condition).

Session 2: Intermediate—Predictive Sounds and Meanings. Instead of picture stimuli, words will be displayed on the screen. One of the words is the correct answer to the target stimuli. During the familiarization phase subjects will have X seconds to familiarize themselves with word stimuli appearing on screen. The length of this familiarization phase is proportional to the number of word stimuli on screen (i.e. more words on the screen means more time to familiarize). tVNS/TENS stimulation or sham stimulation will only be administered during the familiarization phase. After the familiarization phase is over subjects will hear a buzz, indicating that they look at the fixation point in the middle of the screen. Once they have held their gaze on the fixation point for 3 seconds a question appears in its place. The question will refer to one of the words on the screen. To make their decision, subjects can either hold their gaze over the correct response (for a duration of x seconds) or press a button corresponding to its position on screen. Allotted decision time will be directly proportional to the amount of available responses (words/stimuli) on the screen and level of difficulty. Session 2(a) will have four available stimuli response options; session 2(b) will have 8 possible response options. For the harder conditions in session 2(b), tVNS/TENS stimulation will also be administered within the first few seconds of the decision phase. There will be a total of 4 conditions: rhyming (all stimuli words rhyme), phonetically similar/half-rhymes (all stimuli words are half rhymes), visually similar (all stimuli words start with the same letter), semantically similar (all stimuli words belong to similar category for example all animals)

Response latency (how long it took to provide a response), accuracy (did the subject chose the correct response), pupil diameter (uncertainty/measure of task difficulty), and gaze-pattern (how much time was spent looking at each response stimuli) will be measured for each subject across all trials Session 3: Hard: Predictive. This session will present SAT style sentence completion questions adapted to the visual world paradigm framework. This session is more challenging because subjects have to consider multiple linguistic variables, such as sentence tone, prepositions, and verbs to make a predictive inference. Instead of picture stimuli as in session 1, words (like session 2) will be displayed. The words may or may not fit into the sentence provided after the familiarization phase. The sentence will appear written on the fixation point after the familiarization phase. The length of the familiarization phase will be directly proportional to the number of stimuli presented on the screen. tVNS/TENS stimulation or sham stimulation will only be administered during the familiarization phase. When this phase is over subjects will hear a buzz indicating that they should look to the fixation point in the middle of the screen. Once they have held their gaze for 3 seconds over fixation point a sentence completion style question will appear. Allotted decision time will be directly proportional to the amount of available responses (words) on the screen and level of difficulty (such as how many gaps need to be filled in). To make their decision, subjects can either hold their gaze over the correct response (for a duration of x seconds) or press a button corresponding to its position on screen. For the harder conditions stimulation is also administered within the first few seconds of the decision phase. Session 3(a) will have one condition; 4 stimuli/response options and one gap to fill. Session 3(b) will have 2 conditions; 5 stimuli/response options and 2 gaps to fill or 5 stimuli/response options and 3 gaps to fill.

Response latency (how long it took to provide a response), accuracy (did the subject chose the correct response), pupil diameter (uncertainty/measure of task difficulty), and gaze-pattern (how much time was spent looking at each response stimuli) will be measured for each subject across all trials.

Figure 16:
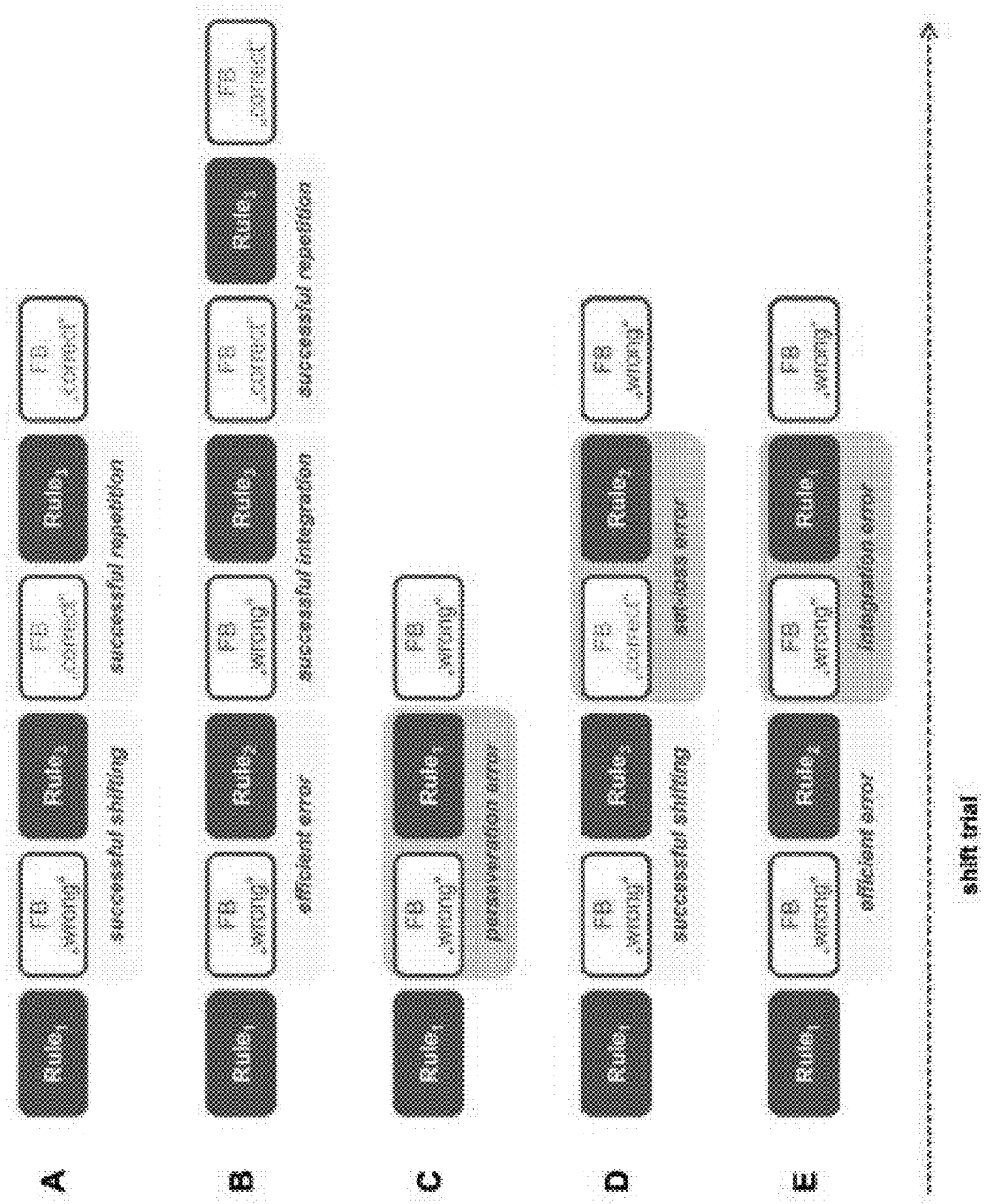
FIG. 16 is an exemplary illustration of Wisconsin Card Sorting Test according to embodiments of the present systems and methods.

Training series 3 Wisconsin Card Sorting Task. An example of a Wisconsin Card Sorting Test (WCST) is shown in FIG. 16. The WCST is a neuropsychological test of "set-shifting," or the ability to flexibly adapt when faced with changing rules or parameters (Heaton et al. 1993). The traditional testing paradigm asks subjects to classify cards according to an unknown criteria (such as the color of its symbols, shape of the symbols, or number of shapes on each card) by trial and error. To identify the rule, participants rely on experimental feedback. Once the correct rule has been identified and correctly implemented for a certain number of trials (usually 10) the valid task rule changes. Participants then have to infer a new rule via trial-and-error. Once a new rule has been uncovered, participants have to update rule maintained in working memory and continue to use it until said rule is deemed inappropriate.

The WCST is understood as a good measure of set-shift attentional abilities, but other cognitive processes such as set-maintenance and rule inference are also involved for successful performance. Disentanglement of executive processes involved has been achieved by comparing between error types. These traditionally include comparison between perseverance errors (PE) and non-perseverance errors. Lange et al. 2016 (among others), argue that simply comparing between these types of errors is not enough since there are a number of cognitive processes that could be responsible for non-perseverance errors. To further disentangle these, they specify two other types of errors within non-perseverance errors, namely set-loss errors (SE) dependent on set-maintenance abilities and integration-errors (IE) dependent on successful working memory (WM) maintenance and updating abilities. To further probe at IE Lange et al. developed an experimental paradigm enabling comparison between WCST-like tasks sensible to different WM loads. We will use an adapted version of their experimental protocol in our three series of testing. We will administer a computerized version of the WCST using our customized software developed in Task 2. For each session subjects will be given instructions and training how to do the task.

In this example, 50 healthy subjects will be recruited by two research coordinators with the support of GU administrative resources. All subjects will be right-handed and will provide informed consent prior to first session. Stimulation will be administered in a double-blind fashion. Half of the participants will receive tVNS and the other half will receive sham stimulation.

For all sessions, subjects will provide information about previous night sleep, affect, mood etc. using questionnaires and visual analogue scales. Heart rate, body temperature, and pupil size will be monitored throughout task to help probe at predictive-inference capabilities and regulate for any possible cardiac side effects. P300 EEG response will also be noted for comparison and data analysis purposes. For each subject, we will try to conduct sessions at the same time/day of the week to reduce confounding effects. Each subject will attend a 1 hour session each week. All training will take place in a dedicated space at the GU Medical Center.

Series 1. Participants will switch between three card-sorting rules identical to computerized WCST. We adapted the protocol to see the effect of predictive-inference on performance. More specifically we altered the predictability of onset of rule-change (length of repetition runs) using three subtask protocols (Altmann, 2004 and Lange et al 2016).

High Predictive Switch Condition→Rule changed after subject had correctly implemented in for 10 consecutive trials (like traditional WCST). Low Predictive Switch Condition→Length of repetition runs was determined by adding two to a sample from an exponential distribution with a rate parameter of lambda=1.5 which accumulates to a mean run length of 3.5. This kept valid rule from changing prior to correct identification and implementation of valid rule on 2 trials (minimum run length=2) but ensured that participants could not anticipate the occurrence of rule shift (Altmann, 2004).

Series 2. The number of viable-task rules was manipulated in three conditions: two-rule condition, three-rule condition and four-rule condition. The two-rule condition will be identical to traditional WCST. For the three and four rule conditions, the traditional WCST paradigm will be altered to include rules across four domains rather than three, specifically: color, shape, number and shading. In these conditions, one of the four rules will be inactive for the participant (participants will be told that there are only three viable rules and the fourth rule will never give positive feedback). The inactive rule will be counterbalanced across participants. The sequence of conditions will also be counterbalanced to avoid any possible confounding ordering effects (Lange et al. 2016).

Figure 17:
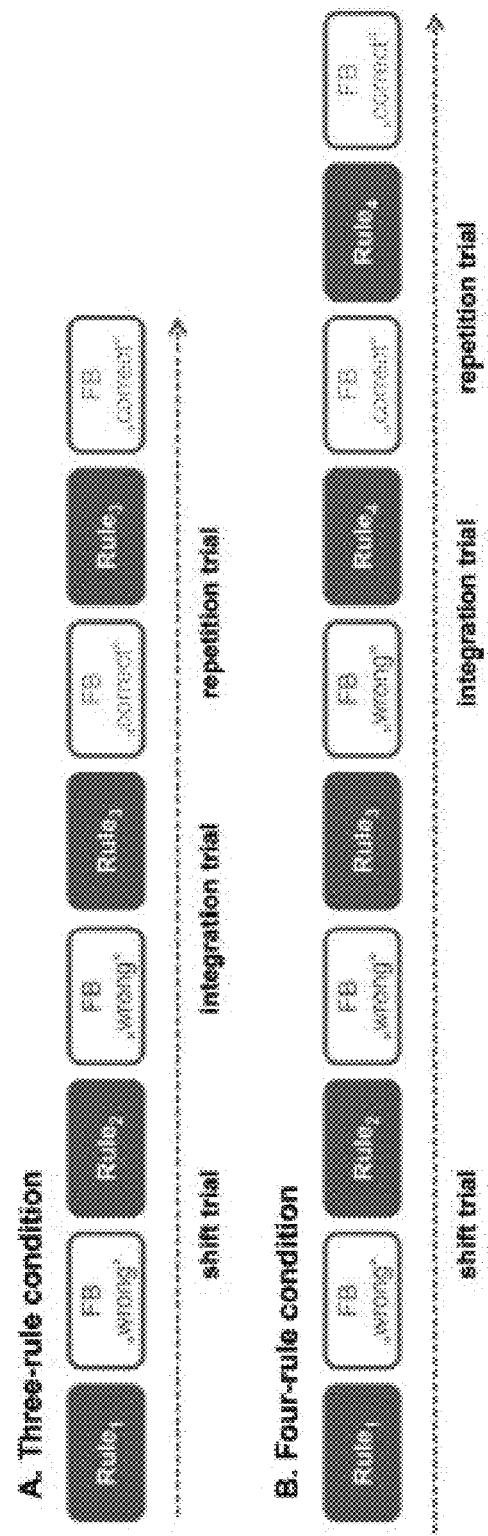
FIG. 17 is an exemplary illustration of Viable Task Rules according to embodiments of the present systems and methods.

The two-rule, three-rule and four rule-conditions will differ in their WM demand. For the two-rule condition (low WM load) subjects have to combine information from the previous trial (1 back) to infer the valid task rule. For the three-rule condition (medium WM load) subjects have to combine information from 2 previous trials (2 back) to infer the valid task rule. For the four-rule condition (high WM load) subjects have to combine information from 3 previous trials (3-back) to infer the valid task rule. Examples of Viable Task Rules are shown in FIG. 17.

Series 3. It is possible that results from Session 1 could be due to differences in extent of habituation, and not necessarily predictive inference. To further dissect this, series 3 will use a more direct measure of predictive inference. Similar to WCST, subjects will have to infer and directly apply, maintain or update a rule to optimize performance. Subjects will receive feedback after each trial. Unlike the WCST, subjects will be told that the optimal rule is not perfectly associated with reward and that some rules will more reliably predict reward. Half the subjects will perform an explicit task first, the other half will perform the implicit task version first to avoid possible conflicting ordering effects. Subjects will have a break between tasks. The explicit and implicit tasks differ in that participants will be told which rule is more likely associated with reward in the former, but will not be told in the latter. Feedback will be given after each trial on both tasks. Within each of these tasks, there will be three conditions, altering the probability of a particular rule (how likely the rule predicted reward). The conditions are: high-probability condition (80-90% reliable), low-probability condition (45-60%) and indiscernible-probability condition (10-20%). Tasks will have two blocks with a rule associated throughout the duration of that block with only 1 switch.

With neural and behavioral data we will analyze the structural and functional systems using graph theory. Closed-loop neurostimulation will be correlated with EEG recording, behavioral measures and cognitive skill training performance to automatically adjust level of peripheral neurostimulation while the training is underway for real time optimization. Closed-loop control could guide perturbations of neural systems (neurons and circuits) to achieve sophisticated, real-time control over neural dynamics and desired cognitive skill, and thus to refine and confirm circuit-based models of the underlying system in the process. The goal of this task is to 1) elucidate (in humans) the anatomical and functional maps of the peripheral and central nervous system circuitry that regulates synaptic plasticity in the brain; 2) Demonstrate (in humans) the effects of peripheral neurostimulation on cognitive skills and the brain activity supporting those skills; 3) Optimize noninvasive stimulation methods and training protocols for long-term retention without negative side effects.

---

Structural and functional mapping from peripheral stimulation to brain activity

1. Brain mapping and plasticity analysis with only VNS
   a. VNS stimulation parameter test and settings
   b. Brain mapping and plasticity analysis with EEG: Run pilots to test experiments; Apply filters to select epochs; Baseline correct and average;
   Evaluate attenuation and reject artifacts; Event-related potentials analysis; Frequency domain analysis; Statistics analysis

| Structural and functional mapping from peripheral stimulation to brain activity |
|---|
| c. Brain mapping and plasticity analysis with ECG: Measurements; Rhythm Analysis; Conduction Analysis; Waveform Description; ECG Interpretation; Comparison with other types of data
2. Brain mapping and plasticity analysis with only TENS
   a. TENS stimulation parameter test and settings
   b. Brain mapping and plasticity analysis with EEG: Run pilots to test experiments; Apply filters to select epochs; Baseline correct and average;
   Evaluate attenuation and reject artifacts; Event-related potentials analysis; Frequency domain analysis; Statistics analysis
   c. Brain mapping and plasticity analysis with ECG: Measurements; Rhythm Analysis; Conduction Analysis; Waveform Description; ECG Interpretation; Comparison with other types of data
3. Brain mapping and plasticity analysis with VNS and TENS
   a. VPS and TENS stimulation parameter test and settings
   b. Brain mapping and plasticity analysis with EEG
   c. Brain mapping and plasticity analysis with ECG |

Big behavioral data evaluation. Behavior is the macroscopic expression of neural activity, implemented by muscular and glandular contractions acting on the body, and resulting in egocentric and allocentric changes in an organized temporal sequence. It is usually high dimensional, making it complex and variable (unpredictable). In this way, behavior is a unifying organismal process which genes, neural function, anatomy and environment converge and interrelate. Thus it's important to link the way of neural systems working to behavior in a systematic way. In our experiments, with the recording from earbuds containing a microphone and speaker, along with various biosensors to track heart rate, breathing rate, movement, posture, pulse oximetry and true body temperature, we aim to use designed experiments and theoretical frameworks to project quantitative, contextual and low-level peripheral stimulation, to high-dimensional and multi-modal neural activity in central nerve system, and then into high-level, universal and comprehensive explanations of animal/human behavior.

Graph theoretical analysis with peripheral stimulation, brain activity, and behavioral output. Graph theoretical analysis of structural and functional systems: with multi-modal brain activity and big behavioral data, we will focus on graph theoretical approaches to the analysis of complex networks that could provide a powerful new way of quantifying the brain's structural and functional systems, thus to enhance cognitive skill learning in healthy adults by using noninvasive peripheral neurostimulation to promote synaptic plasticity in the brain. We will demonstrate this from these aspects: Structural brain networks, which include mapping structural networks in animal models and mapping structural networks in the human brain; Functional brain networks, which include Mapping functional networks using fMRI and Mapping functional networks using electrophysiological techniques; and also Structure-Function relations in brain networks.

Closed-loop neurostimulation optimization. Closed-loop neurostimulation system: in closed-loop neurostimulation application, an understanding of the relationship between human behavioral performance and physiological signals under the influence of external neurostimulation is fundamental to any utilization of the signal as a surrogate marker for cognitive enhancement.

Figure 18:
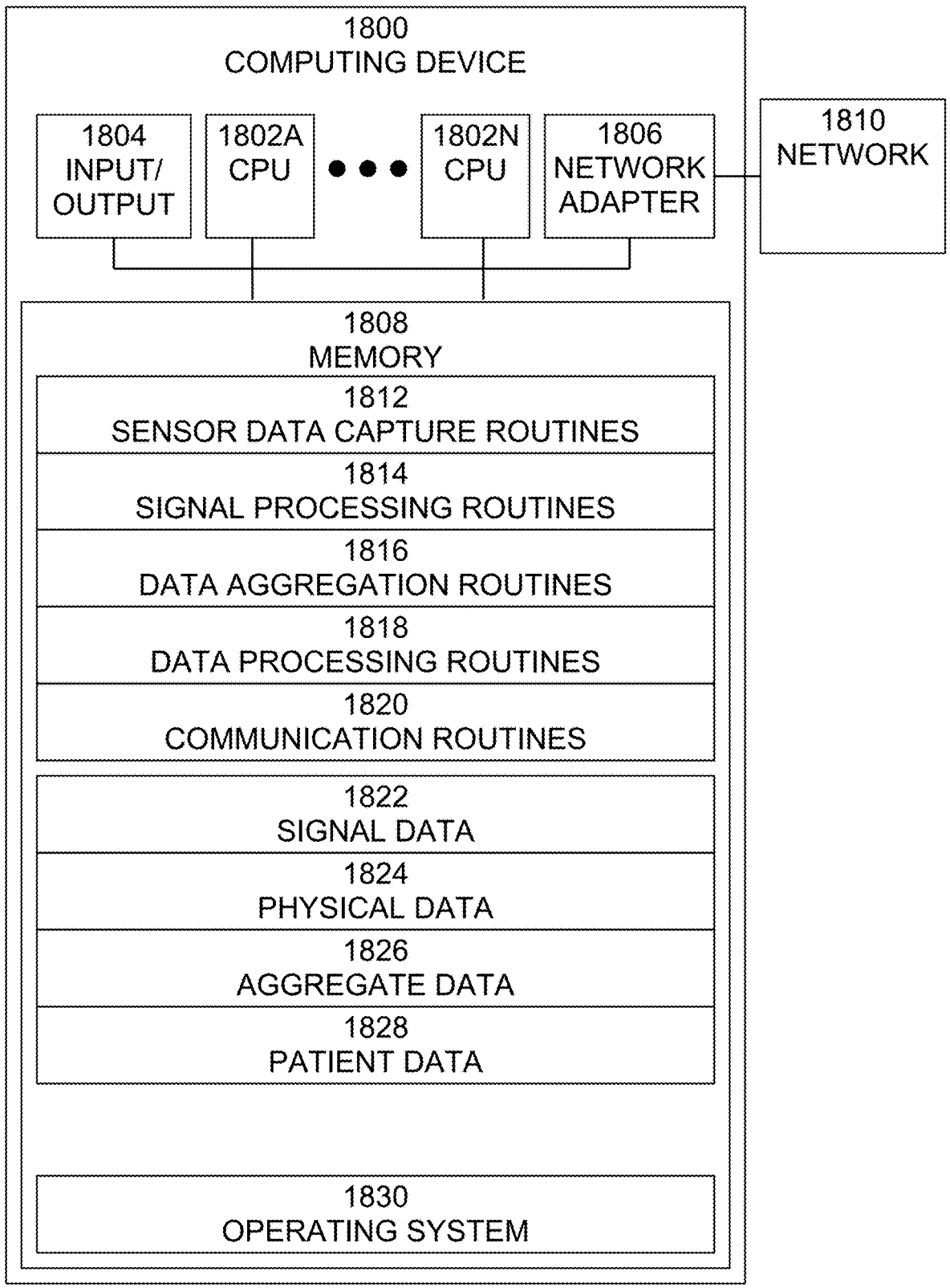
FIG. 18 is an exemplary block diagram of a computer system in which processes involved in the embodiments described herein may be implemented.

An exemplary block diagram of a computer system 1800, in which processes involved in the embodiments described herein may be implemented, is shown in FIG. 18. Computer system 1800 is typically a programmed general-purpose computer system, such as an embedded processor, system on a chip, personal computer, workstation, server system, and minicomputer or mainframe computer. Computer system 1800 may include one or more processors (CPUs) 1802A-1802N, input/output circuitry 1804, network adapter 1806, and memory 1808. CPUs 1802A-1802N execute program instructions in order to carry out the functions of the present invention. Typically, CPUs 1802A-1802N are one or more microprocessors, microcontrollers, processor in a System-on-chip, etc. FIG. 18 illustrates an embodiment in which computer system 1800 is implemented as a single multi-processor computer system, in which multiple processors 1802A-1802N share system resources, such as memory 1808, input/output circuitry 1804, and network adapter 1806. However, the present invention also contemplates embodiments in which computer system 1800 is implemented as a plurality of networked computer systems, which may be single-processor computer systems, multi-processor computer systems, or a mix thereof.

Input/output circuitry 1804 provides the capability to input data to, or output data from, computer system 1800. For example, input/output circuitry may include input devices, such as sensors, microphones, keyboards, mice, touchpads, trackballs, scanners, etc., output devices, such as speakers, video adapters, monitors, printers, etc., and input/output devices, such as, modems, etc. Network adapter 1806 interfaces device 1800 with a network 1810. Network 1810 may be any public or proprietary LAN or WAN, including, but not limited to the Internet.

Memory 1808 stores program instructions that are executed by, and data that are used and processed by, CPU 1802 to perform the functions of computer system 1800. Memory 1808 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 1808 may vary depending upon the function that computer system 1800 is programmed to perform. One of skill in the art would recognize that routines, along with the memory contents related to those routines, may not typically be included on one system or device, but rather are typically distributed among a plurality of systems or devices, based on well-known engineering considerations. The present invention contemplates any and all such arrangements.

In the example shown in FIG. 18, memory 1808 may include sensor data capture routines 1812, signal processing routines 1814, data aggregation routines 1816, data processing routines 1818, communication routines 1820, signal generation routines 1821, signal data 1822, physical data 1824, aggregate data 1826, patient data 1828, and operating system 1830. For example, sensor data capture routines 1812 may include software routines to receive and process signals from sensors, such as those described above, to form signal data 1822. Signal processing routines 1814 may include software routines to process signal data 1820, as described above, to form physical data 1824. Data aggregation routines 1816 may include software routines to process physical data 1824, as described above, to generate aggregate data 1826. Data processing routines 1818 may include software routines to process physical data 1824, aggregate data 1826, and/or patient data 1828. Communications routines 1820 may include software routines to provide communication functionality. Signal generation routines 1822 may include software routines to generate stimulus signals to be applied to subjects. Operating system 1820 provides overall system functionality.

As shown in FIG. 18, the present invention contemplates implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multitasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A system for monitoring and stimulating human body activity and conditions comprising:
    at least one transcutaneous electrical nerve stimulation (TENS) unit adapted to generate an electrical nerve stimulation signal and adapted to apply the nerve stimulation signal to a nerve of a human through a skin of the human using at least one electrode or contact;
    at least one transcutaneous vagal nerve stimulation (tVNS) unit adapted to generate a vagal nerve stimulation signal and adapted to apply the vagal nerve stimulation signal to a vagal nerve of a human through the skin of the human using at least one electrode or contact; and
    at least one transcutaneous electrical nerve stimulation (TENS) unit adapted to generate a nerve stimulation signal and adapted to apply the nerve stimulation signal to at least one nerve of a human through the skin of the human using at least one electrode or contact; and
    transcutaneous electrical nerve monitoring circuitry comprising a processor, storage, an analog to digital converter, at least one sensor adapted to obtain at least one nerve signal from a human through the skin of the human, and a wireless communication unit, wherein the processor is operably connected to the storage to store and retrieve data, the analog to digital converter is operably connected to the at least one sensor to receive an analog nerve signal and output a digital signal to the processor, the wireless communication unit is operably connected to the processor to provide wireless communications, and the power supply is operably connected to the processor, storage, analog to digital converter, and wireless communication unit;
    wherein the processor is further adapted to control signal generation and signal application of the TENS unit and the tVNS unit.

2. The system of claim 1, wherein there are a plurality of transcutaneous electrical nerve stimulation units.

3. The system of claim 2, wherein the at least one electrode or contact adapted to apply the vagal nerve stimulation signal to a vagal nerve of a human is adapted to apply the vagal nerve stimulation signal to an auricular branch of a vagus nerve in a cymba conchae of an ear of the human.

4. The system of claim 3, wherein at least the transcutaneous vagal nerve stimulation (tVNS) unit and the at least one vagal nerve stimulation electrode or contact are included in an ear-mounted device adapted to be at least partially inserted in the ear of the human.

5. The system of claim 1, wherein the transcutaneous electrical nerve stimulation (TENS) unit and the transcutaneous electrical nerve stimulation electrode or contact are included in a device adapted to be attached to a body of the human and the transcutaneous electrical nerve stimulation (TENS) unit is adapted to communicate with the processor using the wireless communication unit.

6. The system of claim 1, wherein the transcutaneous electrical nerve monitoring circuitry sensor comprises at least one of: audio sensors, video sensors, EEG sensors, ECG sensors, heart rate sensors, breathing rate sensors, blood pressure sensors, body temperature sensors, head movement sensors, body posture sensors, and blood oxygenation levels sensors.

7. The system of claim 1, further comprising a computing device adapted to wirelessly communicate with the processor via the wireless communication unit.

8. The system of claim 7, further comprising at least one server computer system adapted to communicate with the computing device.

9. The system of claim 1, further comprising a helmet adapted to be worn on a head of the human, the helmet comprising:
    at least one sensor selected from a group comprising: audio sensors, video sensors, EEG sensors, ECG sensors, heart rate sensors, breathing rate sensors, blood pressure sensors, body temperature sensors, head movement sensors, body posture sensors, and blood oxygenation levels sensors; and
    a wireless communications unit adapted to provide communications with at least one ear-mounted device and at least one computing device.

10. The system of claim 1, wherein the sensor comprises an electrode or contact comprising at least one of a carbon nanotube or graphene.

11. A method for monitoring and stimulating human body activity and conditions comprising:
    generating, at control circuitry comprising a processor, storage, a power supply, and a wireless communication unit, wherein the processor is operably connected to the storage to store and retrieve data, the wireless communication unit is operably connected to the processor to provide wireless communications, and the power supply is operably connected to the processor, storage, and wireless communication unit, control signals to control signal generation and signal application of at least one transcutaneous electrical nerve stimulation (TENS) signal, control signals to control signal generation and signal application of at least one transcutaneous vagal nerve stimulation (tVNS) signal and control signals to control monitoring of at least one nerve signal;

generating, at at least one transcutaneous nerve electrical stimulation (TENS) unit, under control of the controls signals, at least one nerve stimulation signal and transmitting the generated at least one nerve stimulation signal to at least one electrode or contact adapted to apply the nerve stimulation signal to a nerve of a human through the skin of the human;

generating, at at least one transcutaneous vagal nerve stimulation (tVNS) unit, under control of the controls signals, at least one vagal nerve stimulation signal and transmitting the generated at least one vagal nerve stimulation signal to at least one electrode or contact adapted to apply the vagal nerve stimulation signal to a vagal nerve of a human through the skin of the human; and monitoring, at transcutaneous electrical nerve monitoring circuitry comprising the processor, the storage, the power supply, and the wireless communication unit, and further comprises an analog to digital converter and at least one sensor adapted to obtain at least one nerve signal from a human through the skin of the human, wherein the analog to digital converter is operably connected to the at least one sensor to receive an analog nerve signal and output a digital signal to the processor, under control of the controls signals, at least one nerve signal received from the at least one sensor.

12. The method of claim 11, wherein there are a plurality of transcutaneous nerve stimulation units.

13. The method of claim 12, wherein the at least one electrode or contact adapted to apply the vagal nerve stimulation signal to a vagal nerve of a human is adapted to apply the vagal nerve stimulation signal to an auricular branch of a vagus nerve in a cymba conchae of an ear of the human.

14. The method of claim 13, wherein at least the transcutaneous vagal nerve stimulation (tVNS) unit and the at least one vagal nerve stimulation electrode or contact are included in an ear-mounted device adapted to be at least partially inserted in the ear of the human.

15. The method of claim 12, further comprising:
monitoring at least one physical or physiological condition of the human using a helmet adapted to be worn on a head of the human, the helmet comprising at least one sensor selected from a group comprising: audio sensors, video sensors, EEG sensors, ECG sensors, heart rate sensors, breathing rate sensors, blood pressure sensors, body temperature sensors, head movement sensors, body posture sensors, and blood oxygenation levels sensors; and
communicating with at least one ear-mounted device and at least one computing device using a wireless communications unit included in the helmet.

16. The method of claim 11, wherein the transcutaneous electrical nerve stimulation (TENS) unit and the transcutaneous electrical nerve stimulation electrode or contact are included in a device adapted to be attached to a body of the human and the transcutaneous electrical nerve stimulation circuitry is adapted to communicate with the processor using the wireless communication unit.

17. The method of claim 11, further comprising monitoring, using the transcutaneous electrical nerve monitoring circuitry, at least one physical or physiological condition of the human using at least one sensor selected from a group comprising: audio sensors, video sensors, EEG sensors, ECG sensors, heart rate sensors, breathing rate sensors, blood pressure sensors, body temperature sensors, head movement sensors, body posture sensors, and blood oxygenation levels sensors.

18. The method of claim 11, further comprising communicating with a computing device via the wireless communication unit.

19. The method of claim 11, further comprising communicating with at least one server computer system adapted to communicate with the computing device.

20. The system of claim 11, wherein the electrode or contact comprises at least one of a carbon nanotube or graphene.

* * * * *